US006087096A

United States Patent [19]
Dau et al.

[11] Patent Number: 6,087,096
[45] Date of Patent: Jul. 11, 2000

[54] METHOD OF INTRAFAMILY FRAGMENT ANALYSIS OF THE T CELL RECEPTOR α AND β CHAIN CDR3 REGIONS

[76] Inventors: Peter C. Dau, 907 Green Bay, Winnetka, Ill. 60093; Debang Liu, 2439 S. Scoville, Berwyn, Ill. 60402

[21] Appl. No.: 08/559,205

[22] Filed: Nov. 13, 1995

[51] Int. Cl.[7] ........................................... C12Q 1/68
[52] U.S. Cl. ..................... 435/6; 435/91.1; 435/91.2; 435/91.21
[58] Field of Search .............. 435/6, 91.1, 91.2, 435/91.21; 436/94

[56] References Cited

U.S. PATENT DOCUMENTS

| | | | |
|---|---|---|---|
| 4,873,190 | 10/1989 | Saito et al. | 435/172.3 |
| 4,874,845 | 10/1989 | Saito et al. | 530/395 |
| 5,296,351 | 3/1994 | Morley et al. | 435/6 |
| 5,298,396 | 3/1994 | Kotzin et al. | 435/7.24 |
| 5,316,925 | 5/1994 | Davis et al. | 435/91.2 |
| 5,336,598 | 8/1994 | Kotzin et al. | 435/7.24 |
| 5,418,134 | 5/1995 | Morley et al. | 435/6 |
| 5,445,940 | 8/1995 | Brenner et al. | 435/7.24 |
| 5,635,354 | 6/1997 | Kourilsky et al. | 435/6 |
| 5,700,907 | 12/1997 | Hercend et al. | 530/324 |
| 5,837,447 | 11/1998 | Gorski | 435/6 |

FOREIGN PATENT DOCUMENTS

| | | |
|---|---|---|
| 660660 | 7/1995 | Australia . |
| 0 653 493 A1 | 5/1995 | European Pat. Off. . |
| WO 90/04648 | 5/1990 | WIPO . |
| WO 91/09623 | 7/1991 | WIPO . |
| WO 91/19816 | 12/1991 | WIPO . |
| WO 92/12260 | 7/1992 | WIPO . |
| WO 92/13950 | 8/1992 | WIPO . |
| WO 94/01581 | 1/1994 | WIPO . |

OTHER PUBLICATIONS

PCT Written Opinion, International application No. PCT/US96/18134, dated Oct. 15, 1997.
Currier, et al., "Mitogens, Superantigens, and Nominal Antigens Elicit Distinctive Patterns of TCRB CDR3 Diversity," *Human Immunology*, 48:39–51 (Jun. 1996).
Desravines, et al., "Measuring CDR3 Length Variability in Individuals During Ontogeny," *J. Immun. Methods*, 168:219–225 (1994).
Panzara, et al., "Analysis of the T Cell Repertoire Using the PCR and Specific Oligonucleotide Primers," *Biotechniques*, 12(5):728–735 (1992).
Bjorkman et al., "The foreign antigen binding site and T cell recognition regions of class I histocompatibility antigens," *Nature*, 329:512–518 (Oct. 8, 1987).
Blumberg et al., Human Intestinal Intraepithelial Lympocytes Are Derived from a Limited Number of T Cell Clones that Utilize Multiple Vβ T Cell Receptor Genes, *The Journal of Immunology*, 150(11):5144–5153 (Jun. 1, 1993).
Boehncke et al., "T–Cell–Receptor Repertoire in Chronic Plaque–Stage Psoriasis Is Restricted and Lacks Enrichment of Superantigen–Associated Vβ Regions," *The Journal of Investigative Dermatology*, 104:725–728 (1995).

Bordignon et al., "Gene Therapy in Peripheral Blood Lymphocytes and Bone Marrow for ADA Immunodeficient Patients," *Science*, 270:470–475 (Oct. 20, 1995).
Brown et al., "Three–dimensional structure of the human class II histocompatibility antigen HLA–DR1," *Nature*, 364:33–39 (Jul. 1, 1993).
Choi et al., "Interaction of *Staphylococcus aureus* toxin 'superantigens' with human T Cells," *Proc. Natl. Acad. Sci. USA*, 86:8941–8945 (Nov., 1989).
Chothia, et al., "The outline of structure of the T–cell αβ receptor," *The EMBO Journal*, 7(12):3745–3755 (1988).
Cochet et al., "Molecular detection and in vivo analysis of the specific T Cell response to a protein antigen," *Eur. J. Immunol.*, 22:2639–2647 (1992).
Cottrez et al., "Analysis of the Vβ specificity of superantigen activation with a rapid and sensitive method using RT PCR and an automatic DNA analyser," *Journal of Immunological Methods*, 172:85–94 (1994).
Davis et al., "T–cell antigen receptor genes and T–cell recognition," *Nature*, 334:395–402 (Aug. 4, 1988).
Delfau et al., "Restricted diversity of $V_\gamma 9$–JP rearrangements in unstimulated human γ/δ T lymphocytes," *Eur. J. Immunol.* 22:2437–2443 (1992).
DePalma et al., "Restricted and conserved T–cell repertoires involved in allorecognition of class II major histocompatibility complex," *Proc. Natl Acad Sci. USA* 92:8836–8840 (Sep., 1995).
Dietrich et al., "Analysis of T–Cell Receptor Variability in Transplanted Patients With Acute Graft–Versus–Host Disease," *Blood*, 80(9):2419–2424 (Nov. 1, 1992).
Dietrich et al., "In Vivo T–Cell Clonal Amplification at Time of Acute Graft–Versus–Host Disease," *Blood*, 84(8):2815–2820 (Oct. 15, 1994).
Diu et al., "Limited T–cell Receptor Diversity in Liver–infiltrating Lymphocytes from Patients with Primary Biliary Cirrhosis," *Journal of Autoimmunity* 6:611–619 (1993).
Farace et al., "T Cell Repertoire in Patients with B Chronic Lympocytic Leukemia," *The Journal of Immunology*, 153:4281–4290 (1994).
Gaudin et al., "In vivo Local Expansion of Clonal T Cell Subpopulations in Renal Cell Carcinoma," *Cancer Research* 55:685–690 (Feb. 1, 1995).
Genevée et al., "An experimentally validated panel of subfamily–specific oligonucleotide primers ($V_\alpha 1$–w29/$V_\beta 1$–w24) for the study of human T cell receptor variable V gene segment usage by polymerase chain reaction," *Eur. J. Immunol.* 22:1261–1269 (1992).

(List continued on next page.)

*Primary Examiner*—David Saunder
*Attorney, Agent, or Firm*—Marshall, O'Toole, Gerstein, Murray & Borun

[57] ABSTRACT

A method and kit are provided for quantitatively determining the length distributions of the third complementarity determining region (CDR3) of the T cell receptor (TCR) α and β chains from human lymphocytes in a tissue sample or in the peripheral blood.

47 Claims, 17 Drawing Sheets s

OTHER PUBLICATIONS

Gorski et al., "Circulating T Cell Repertoire Complexity in Normal Indivuduals and Bone Marrow Recipients Analyzed by CDR3 Size Spectratyping," *Journal of Immunology*, 152:5109–5119 (1994).

Hall et al., "PCR–Based Analysis of the T–Cell Receptor Vβ Multigene Family: Experimental Parameters Affecting Its Validity," *BioTechniques*, 13(2):248–257 (1992).

Hall et al., "Healthy Human T–Cell Receptor β–Chain Repertoire Quantitative Analysis and Evidence for Jβ–Related Effects on CDR3 Structure and Diversity," *Human Immunology 43*:207–218 (1995).

Hingorani et al., "Clonal Predominance of T Cell Receptors Within the CD8+ CD45RO+ Subset in Normal Human Subjects," *The Journal of Immunology*, 151(10):5762–5769 (Nov. 15, 1993).

Jores et al., "Few V Gene Segments Dominate the T Cell Receptor β–Chain Repertoire of the Human Thymus," *The Journal of Immunology*, 151(11):6110–6122 (Dec. 1, 1993).

Kabat et al., *Sequences of Proteins of Immunological Interest*, Fifth edition, U.S. Dept. of Health and Human Services, NIH publication 91–3242 (1991), p. 2164.

Kimura et al., "Sequences and repertoire of the human T cell receptor α and β chain variable region genes in thymocytes," *Eur. J. Immunol.* 17:375–383 (1987).

Klein et al., "Diversity and structure of human T–cell receptor α–chain variable region genes," *Proc. Natl. Acad. Sci. USA*, 84:6884–6888 (Oct., 1987).

Liu et al., "Intrafamily fragment anlaysis of the T cell receptor β chain CDR3 region," *Journal of Immunological Methods*, 187:139–150 (1995).

Lynas et al., "A rapid and reliable PCR method for detecting clonal T cell populations," *J. Clin. Pathol. Mol. Pathol.* 48:M101–M104 (1995).

Moss et al., "Sequence analysis of the human αβ T–cell receptor CDR3 region," *Immunogenetics 42*:10–18 (1995).

Oaks et al., "T–Cell Receptor α and β Chain Gene Expression in Cells Infiltating Human Cardiac Allografts," *Am. J. Med. Sci.*, 390(1):26–34 (Jan., 1995).

Offermans et al., "Denaturing and non–denaturing gel electrophoresis as methods for the detection of junctional diversity in rearranged T cell receptor sequences," *Journal of Immunological Methods*, 181:101–114 (1995).

Okubo et al., "Clonotype Analysis of Peripheral Blood T Cells and Autoantigen–Reactive T Cells from Patients with Mixed Connective Tissue Disease," *The Journal of Immunology*, 153:3784–3790 (1994).

Pannetier et al., "The sizes of the CDR3 hypervariable regions of the murine T–cell receptor β chains vary as a funtion of the recombined germ–line segments," *Proc. Natl. Acad. Sci. USA*, 90:4319–4323 (May, 1993).

Pannetier, et al., "T–cell repertoire diversity and clonal expansions in normal and clinical samples," *Immunology Today*, 16(4):176–181 (1995).

Prevost–Blondel et al., "CDR3 size analysis of T cell receptor V beta transcripts: follow–up study in a patient with T cell acute lymphoblastic leukemia," *Leukemia* 9:1711–1717 (1995).

Product literature for Applied Biosystems Gene Scanner™ 362 Fluorescent Fragment Analyzer.

Puisieux et al., "Oligoclonality of Tumor–Infiltrating Lymphocytes from Human Melanomas," *The Journal of Immunology*, 153:2807–2818 (1994).

Robinson, "The Human T–Cell Receptor β–Chain Gene Complex Contains at Least 57 Variable Gene Segments," *The Journal of Immunology*, 146(12):4392–4397 (Jun. 15, 1991).

Rock et al., "CDR3 Length in Antigen–specific Immune Receptors," *J. Exp. Med.*, 179:323–328 (Jan., 1994).

Roman–Roman et al., "Studies on the human T cell Receptor α/β variable region genes I. Identification of 7 additional $V_\alpha$ subfamilies and 14 $J_\alpha$ gene segments," *Eur. J. Immunol.* 21:927–933 (1991).

Rosenberg et al., "Variation in human T cell receptor Vβ and Jβ repertoire: analysis using anchor polymerase chain reaction," *Eur. J. Immunol.* 22:541–549 (1992).

Smith et al., "T cell receptor repertoire of CD4+ and CD8+ T cell subsets in the allogeneic bone marrow transplant recipient," *Cancer Immunol. Immuother.* 41:104–110 (1995).

Wei et al., "The extent of the human germline T–cell receptor V beta gene segment repertoire," *Immunogenetics* 40:27–36 (1994).

Yoshikai et al., "Sequences and Repertoire of Human T Cell Receptor α Chain Variable Region Genes in Mature T Lymphocytes," *J. Exp. Med.*, 164:90–103 (Jul., 1986).

Yurovsky et al., "Analysis of diversity of T cell antigen receptor genes using polymerase chain reaction and sequencing gel electrophoresis," *J. Immunol. Methods* 175:227–236 (1994).

FIG. 3B

BETA CHAIN FREQUENCY DISTRIBUTION OF CDR3 LENGTH (%)

| CDR3 | 0 | 1 | 2 | 3 | 4 | 5 | 6 | 7 | 8 | 9 | 10 | 11 | 12 | 13 | 14 | 15 | 16 | 17 | 18 | 19 | 20 | 21 |
|---|---|---|---|---|---|---|---|---|---|---|---|---|---|---|---|---|---|---|---|---|---|---|
| V Beta 1 | | | | 0.1 | 0.1 | 0.5 | 2.8 | 10.2 | 14.3 | 19.6 | 20.5 | 14.9 | 6.3 | 3.1 | 2.1 | 1.6 | 1.5 | 1.2 | 0.9 | 0.3 | | |
| V Beta 2 | | | 0.9 | | 0.6 | 2.6 | 7.2 | 13.6 | 20.8 | 21.4 | 14.8 | 8.4 | 4.5 | 1.8 | 1.7 | 1.5 | 0.7 | 0.3 | 0.1 | | | |
| V Beta 3 | | 0.3 | | 1.4 | 1.9 | 4.7 | 6.9 | 10.4 | 13.4 | 17.9 | 16.0 | 9.7 | 8.2 | 2.3 | 2.0 | 1.7 | 0.9 | 0.5 | 0.5 | 0.2 | 0.1 | |
| V Beta 4 | | | 0.1 | 0.4 | 1.0 | 3.3 | 9.5 | 16.2 | 18.2 | 17.6 | 12.6 | 6.7 | 3.5 | 3.2 | 2.8 | 2.3 | 1.3 | 0.6 | 0.2 | 0.3 | | |
| V Beta 5.1 | | | 0.4 | 0.5 | 0.6 | 0.7 | 2.2 | 5.5 | 14.1 | 19.7 | 21.4 | 14.9 | 8.3 | 4.2 | 2.5 | 2.0 | 1.8 | 1.0 | 0.2 | | | |
| V Beta 5.2 | | | | | 0.3 | 1.6 | 4.5 | 10.7 | 16.7 | 20.5 | 19.7 | 11.0 | 6.0 | 3.1 | 2.0 | 1.9 | 1.4 | 0.5 | 0.1 | | | |
| V Beta 6 | | | | 0.1 | | 1.0 | 2.6 | 8.5 | 13.7 | 20.6 | 17.1 | 12.8 | 11.0 | 5.2 | 3.2 | 2.0 | 1.1 | 0.6 | 0.3 | 0.1 | | |
| V Beta 7 | 0.1 | | 0.1 | 0.1 | 0.1 | 0.2 | 1.7 | 4.2 | 11.3 | 17.2 | 23.0 | 18.2 | 12.6 | 5.3 | 2.3 | 1.4 | 1.2 | 0.7 | 0.3 | 0.1 | | |
| V Beta 8 | | | 0.1 | 0.2 | 0.4 | 0.7 | 5.2 | 8.4 | 15.9 | 20.0 | 18.8 | 11.8 | 6.8 | 3.3 | 2.8 | 2.3 | 1.9 | 0.9 | 0.4 | 0.1 | | |
| V Beta 9 | | | | | 0.3 | 1.7 | 5.7 | 10.8 | 15.5 | 20.5 | 18.9 | 14.2 | 5.5 | 2.9 | 1.5 | 1.2 | 0.8 | 0.5 | | | | |
| V Beta 10 | | | | 0.1 | 0.4 | 0.9 | 1.9 | 4.1 | 7.6 | 11.4 | 20.1 | 14.6 | 12.8 | 9.3 | 7.0 | 4.8 | 2.4 | 1.4 | 0.9 | | | |
| V Beta 11 | 0.1 | | 0.2 | 0.4 | 0.7 | 3.5 | 6.2 | 11.0 | 14.5 | 19.0 | 19.8 | 13.1 | 5.9 | 2.5 | 1.1 | 0.9 | 0.7 | 0.2 | 0.1 | 0.1 | | |
| V Beta 12 | | | | 0.1 | 0.1 | 1.6 | 4.3 | 10.2 | 18.1 | 19.4 | 18.8 | 11.6 | 6.0 | 2.9 | 2.5 | 1.9 | 1.5 | 0.6 | 0.2 | 0.1 | | |
| Beta 13.1 | | | | | 0.1 | 1.5 | 3.9 | 10.1 | 18.3 | 21.4 | 21.1 | 11.4 | 4.6 | 2.6 | 2.0 | 1.6 | 1.2 | 0.3 | | | | |
| Beta 13.2 | 0.1 | | 0.1 | 0.1 | 0.6 | 0.4 | 4.1 | 7.3 | 14.4 | 18.3 | 21.3 | 13.4 | 7.5 | 4.6 | 2.6 | 2.1 | 1.9 | 0.9 | 0.4 | 0.1 | | 0.1 |
| V Beta 14 | 0.1 | | 0.1 | 0.2 | 0.5 | 2.0 | 4.7 | 12.8 | 18.2 | 20.2 | 17.0 | 10.5 | 4.8 | 3.0 | 2.1 | 1.6 | 1.2 | 0.6 | 0.3 | 0.1 | | |
| V Beta 15 | | | | | 0.1 | 0.3 | 2.6 | 7.8 | 14.6 | 16.1 | 18.2 | 16.1 | 9.9 | 4.9 | 2.2 | 2.3 | 2.0 | 1.5 | 0.9 | 0.3 | 0.1 | |
| V Beta 16 | | | | | 0.2 | 0.9 | 3.2 | 8.3 | 15.1 | 17.3 | 19.6 | 15.3 | 9.0 | 6.4 | 2.0 | 1.0 | 0.8 | 0.5 | 0.2 | 0.1 | | |
| V Beta 17 | | | | 0.1 | 0.4 | 1.0 | 3.4 | 11.0 | 17.8 | 24.4 | 22.7 | 9.6 | 4.1 | 2.0 | 1.4 | 1.1 | 0.7 | 0.2 | | | | |
| V Beta 18 | | | | | 0.2 | 0.5 | 2.4 | 8.3 | 16.1 | 19.6 | 19.2 | 15.0 | 6.6 | 3.9 | 2.9 | 2.5 | 1.6 | 1.0 | 0.3 | | | |
| V Beta 20 | | | | | 0.4 | 3.5 | 7.9 | 14.8 | 22.9 | 21.7 | 12.5 | 5.9 | 4.7 | 1.9 | 1.8 | 1.4 | 0.5 | 0.1 | 0.1 | | | |
| V Beta 21 | | | | | 0.1 | 1.9 | 6.0 | 11.3 | 19.0 | 23.4 | 18.6 | 8.7 | 4.5 | 2.0 | 1.2 | 1.7 | 0.8 | 0.3 | 0.2 | 0.1 | | |
| V Beta 22 | | | | | | | 0.7 | 3.5 | 9.5 | 17.7 | 20.8 | 19.9 | 13.7 | 8.3 | 3.4 | 1.3 | 0.7 | 0.4 | 0.1 | | | |
| V Beta 23 | 0.1 | | 0.1 | 0.2 | 0.6 | 0.8 | 1.6 | 5.5 | 10.9 | 13.6 | 23.6 | 15.0 | 11.3 | 6.1 | 3.5 | 2.4 | 2.4 | 1.2 | 0.6 | 0.4 | | |
| V Beta 24 | | | | | | | 1.6 | 4.4 | 9.1 | 16.1 | 22.4 | 21.2 | 11.8 | 6.2 | 2.9 | 1.3 | | | | | | |
| Average | | | 0.1 | 0.2 | 0.4 | 1.4 | 4.1 | 9.2 | 15.2 | 19.0 | 19.1 | 13.0 | 7.6 | 4.0 | 2.5 | 1.8 | 1.2 | 0.6 | 0.3 | 0.1 | 0.1 | |
| Std. Dev. | 0.1 | | 0.2 | 0.3 | 0.4 | 1.2 | 2.3 | 3.4 | 3.7 | 2.8 | 2.9 | 3.8 | 3.1 | 2.0 | 1.1 | 0.8 | 0.6 | 0.4 | 0.3 | 0.1 | | |
| Std Error | | | 0.1 | 0.1 | 0.1 | 0.2 | 0.5 | 0.7 | 0.7 | 0.6 | 0.6 | 0.8 | 0.6 | 0.4 | 0.2 | 0.2 | 0.1 | 0.1 | 0.1 | | | |
| CDR3 | 0 | 1 | 2 | 3 | 4 | 5 | 6 | 7 | 8 | 9 | 10 | 11 | 12 | 13 | 14 | 15 | 16 | 17 | 18 | 19 | 20 | 21 |

FIG. 9B

ALPHA CHAIN FREQUENCY DISTRIBUTION OF CDR3 LENGTH(%)

| CDR3 aa | 0 | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|---|
| V ALPHA 1 | | | 0.02 | 0.14 | 0.56 | 1.28 | 4.04 | 9.95 | 19.35 | 26.12 | 21.50 | 10.82 | 4.34 | 1.51 | 0.34 | 0.02 | | |
| V ALPHA 2 | | 0.02 | 0.02 | 0.19 | 0.43 | 1.92 | 4.69 | 9.96 | 18.69 | 24.41 | 19.67 | 11.36 | 6.05 | 1.97 | 0.55 | 0.08 | | |
| V ALPHA 3 | | | 0.34 | 0.54 | 1.07 | 2.92 | 9.02 | 14.98 | 21.31 | 20.93 | 15.60 | 9.43 | 2.82 | 0.68 | 0.06 | 0.02 | | |
| V ALPHA 4 | | | | | 0.04 | 0.68 | 1.81 | 5.70 | 10.68 | 14.80 | 22.16 | 19.68 | 13.44 | 8.05 | 2.70 | 0.49 | 0.14 | |
| V ALPHA 5 | | | | 0.05 | 0.03 | 0.09 | 0.90 | 4.55 | 12.50 | 22.45 | 26.40 | 17.16 | 10.24 | 4.66 | 0.89 | 0.07 | | |
| V ALPHA 6 | | | | 0.13 | 0.36 | 0.65 | 1.26 | 5.39 | 11.11 | 17.79 | 22.44 | 17.81 | 13.08 | 6.87 | 2.59 | 0.36 | 0.04 | |
| V ALPHA 7 | | | | | 0.51 | 0.80 | 1.80 | 9.87 | 37.00 | 17.97 | 15.09 | 10.04 | 5.03 | 1.39 | 0.42 | 0.05 | | |
| V ALPHA 8 | | | 0.01 | 0.05 | 0.43 | 1.01 | 3.69 | 8.45 | 16.92 | 25.74 | 21.25 | 13.55 | 6.42 | 1.81 | 0.55 | 0.11 | | |
| V ALPHA 9 | | | | 0.13 | 0.34 | 0.60 | 0.70 | 5.01 | 12.63 | 21.61 | 24.28 | 17.71 | 9.73 | 4.38 | 1.86 | 0.90 | 0.12 | |
| V ALPHA 10 | 0.04 | 0.16 | 0.27 | 1.05 | 1.64 | 5.95 | 11.04 | 15.14 | 19.26 | 17.12 | 15.69 | 8.89 | 2.86 | 0.67 | 0.20 | 0.03 | | |
| V ALPHA 11 | | | 0.03 | 0.17 | 0.86 | 2.20 | 8.17 | 13.36 | 21.84 | 23.77 | 18.87 | 7.49 | 2.74 | 0.46 | | | | |
| V ALPHA 12 | | | | 0.04 | 0.05 | 0.22 | 1.21 | 6.01 | 14.57 | 21.31 | 24.47 | 16.93 | 9.41 | 4.47 | 1.09 | 0.23 | | |
| V ALPHA 13 | | | | 0.13 | 0.35 | 1.12 | 3.56 | 6.42 | 15.19 | 22.03 | 23.34 | 16.85 | 6.95 | 2.53 | 1.23 | 0.26 | 0.04 | |
| V ALPHA 14 | | | | 0.04 | 0.14 | 0.18 | 2.42 | 7.50 | 11.06 | 14.26 | 19.89 | 18.48 | 13.08 | 6.87 | 3.50 | 0.70 | 0.19 | |
| V ALPHA 15 | | | 0.03 | 0.63 | 1.20 | 3.68 | 8.38 | 16.90 | 25.53 | 22.53 | 14.31 | 5.06 | 1.31 | 0.39 | 0.05 | | | |
| V ALPHA 16 | | | | | 0.13 | 1.30 | 2.94 | 7.55 | 16.29 | 25.15 | 23.93 | 13.84 | 6.64 | 1.77 | 0.42 | 0.03 | | |
| V ALPHA 17 | | | | | 0.24 | 1.91 | 4.54 | 12.93 | 21.73 | 27.32 | 17.23 | 9.18 | 3.68 | 0.97 | 0.24 | | | |
| V ALPHA 18 | | | | 0.02 | 0.19 | 4.68 | 7.48 | 18.94 | 24.70 | 21.04 | 13.75 | 6.64 | 2.32 | 0.57 | | | | |
| V ALPHA 19 | | | | | 0.07 | 0.15 | 0.54 | 3.01 | 8.65 | 13.82 | 22.14 | 20.49 | 13.09 | 11.04 | 4.94 | 1.58 | 0.41 | 0.06 |
| V ALPHA 20 | | | 0.06 | 0.28 | 1.55 | 3.58 | 10.69 | 19.57 | 23.59 | 20.87 | 13.34 | 5.03 | 1.24 | 0.18 | 0.02 | | | |
| V ALPHA 21 | | | | 0.37 | 1.96 | 6.42 | 11.44 | 18.22 | 22.61 | 17.89 | 10.13 | 7.05 | 3.08 | 0.69 | 0.03 | | | |
| V ALPHA 22 | | | | 0.07 | 0.50 | 2.30 | 6.34 | 11.41 | 18.22 | 22.44 | 25.48 | 16.18 | 8.62 | 3.65 | 1.00 | 0.16 | | |
| V ALPHA 23 | | | 0.16 | 0.19 | 0.59 | 3.36 | 13.00 | 16.40 | 22.81 | 25.67 | 12.96 | 2.67 | 0.47 | 0.02 | 0.02 | | | |
| V ALPHA 24 | | | | | 0.27 | 1.62 | 3.46 | 8.78 | 17.08 | 24.78 | 25.67 | 12.11 | 4.68 | 1.44 | 0.11 | | | |
| V ALPHA 25 | | | | | 0.18 | 5.08 | 6.51 | 10.38 | 22.00 | 21.93 | 14.89 | 17.13 | 10.55 | 6.80 | 4.14 | 1.68 | 0.48 | |
| V ALPHA 26 | | | | 1.38 | 2.73 | 6.03 | 4.19 | 12.45 | 15.69 | 20.54 | 14.89 | 9.84 | 8.99 | 1.38 | 0.22 | | | |
| V ALPHA 27 | | 0.02 | 0.12 | 0.33 | 1.02 | 6.70 | 14.02 | 11.41 | 14.21 | 23.09 | 19.11 | 9.01 | 5.32 | 1.15 | 0.46 | 0.19 | | |
| V ALPHA 28 | | | | | 0.66 | 1.82 | 3.71 | 12.45 | 15.69 | 20.74 | 20.38 | 15.23 | 6.97 | 2.57 | 0.61 | 0.12 | | |
| AVERAGE | 0.00 | 0.01 | 0.04 | 0.15 | 0.45 | 1.54 | 4.23 | 8.98 | 16.57 | 20.74 | 19.55 | 13.90 | 7.75 | 3.54 | 1.32 | 0.36 | 0.07 | 0.01 |
| STDEV | 0.01 | 0.03 | 0.09 | 0.24 | 0.46 | 1.64 | 3.26 | 4.26 | 6.33 | 3.86 | 4.08 | 4.79 | 4.25 | 3.27 | 1.83 | 0.64 | 0.15 | 0.03 |
| STDERR | 0.00 | 0.01 | 0.02 | 0.05 | 0.09 | 0.31 | 0.62 | 0.81 | 1.20 | 0.73 | 0.77 | 0.90 | 0.80 | 0.62 | 0.35 | 0.12 | 0.03 | 0.01 |
| CDR3 aa | 0 | 1 | 2 | 3 | 4 | 5 | 6 | 7 | 8 | 9 | 10 | 11 | 12 | 13 | 14 | 15 | 16 | 17 |

METHOD OF INTRAFAMILY FRAGMENT ANALYSIS OF THE T CELL RECEPTOR α AND β CHAIN CDR3 REGIONS

BACKGROUND OF THE INVENTION

A. Field of the Invention

The present invention relates in general to a method and to a kit of materials for performing T cell repertoire analysis and clinical applications therefore, and more particularly to a method and a kit of materials for determining intrafamily gene fragment length profiles of the T cell receptor α and β chain CDR3 regions.

B. Background

The T lymphocytes are the primary mediators of cellular immunity in humans, occupying an essential role in immune responses to infectious agents (e.g., viruses and bacteria) and in the body's natural defenses against neoplastic diseases. Likewise, T lymphocytes play a central role in acute graft-versus host disease, wherein the immune system of a host attacks (rejects) implanted tissue from a foreign host, in autoimmune disorders, in hypersensitivity, in degenerative nervous system diseases, and many other conditions. A T cell immune response is characterized by one (or more) particular T cell(s) recognizing a particular antigen, secreting growth-promoting cytokines, and undergoing a monoclonal (or oligoclonal) expansion to provide additional T cells to recognize and eliminate the foreign antigen.

Each T cell and its progeny are unique by virtue of a structurally unique T cell receptor (TCR) expressed thereby, which recognizes a complimetary, structurally unique antigen. In the vast majority of T cells (αβ T cells), the T cell receptor is a heterodimer comprised of an alpha- (α-) and beta- (β-) polypeptide chain covalently linked to each other by disulfide bonds. Alpha- and beta-chains both are comprised of an amino-terminal variable (V) region joined to a constant (C) region by an intermediate joining (J) region (and in the case of the β-chain, by a diverstity (D) region as well). The diversity of TCRs is thought to be as large as that of antibodies, arising from the many different combinations of Vα, Jα, Cα gene segments and Vβ, Jβ, Dβ, and Cβ gene segments produced by genetic recombination events.

Within the T cell receptor α and β chain variable regions are hypervariable regions similar to those found in immunoglobulins, where they form the principal points of contact with antigen and thus are referred to as complementarity determining regions (CDR). Based on the analogy with immunoglobulins, these TCR hypervariable regions are thought to loop out from connecting β-sheet TCR framework sequences. Two CDRs (CDR1 and CDR2) are postulated to contact predominantly major histocompatability complex (MHC) peptide sequences, whereas a third, centrally-located CDR (CDR3) is believed to contact antigen bound in a groove between 2 MHC α-helical) peptides. See Bjorkman et al., *Nature,* 329: 512 (1987); Chothia et al., *EMBO J.,* 7: 3745 (1988); Davis et al., *Nature,* 334: 395 (1988); and Brown et al., *Nature,* 364: 33 (1993). Since both α and β chain CDR3 lengths are consistent with directly contacting peptide antigens, they have been postulated to be constrained in size because of their evolutionary selection for binding to peptide-MHC complexes. Rock et al., *J. Exp. Med.,* 179: 323 (1994). Maximum sequence diversity of the TCR β chain is reported to be in the CDR3 region at amino acid positions 96 through 105. Kabat et al., *Sequences of Proteins of Immunologic Interest,* Fifth edition, U.S. Dept. of Health and Human Services, NIH publication 91,3242 (1991). This diversity presumably is used in antigen recognition.

In addition to sequence diversity, TCR α and β chains exhibit length diversity in their CDR3 regions due to nucleotide deletions and additions which occur during genetic recombination. Davis et al., (1988). Sequence data has shown the median CDR3 length in humans for both the α and β chain to be 9 amino acids (a.a.) with a range of 6–12 a.a. Rock et al., (1994). Qualitative studies have suggested a 5–16 a.a. range of CDR3 lengths. Hingorani et al., *J. Immunol.,* 151: 5762 (1993); Gorski et al., *J. Immunol.,* 152: 5109 (1994).

Because of the integral role of T lymphocytes in the immune response, the analysis of the T cell repertoires involved in local and systemic immune responses is beginning to play an important role in many clinical situations, including auto-immunity, response to infectious antigens, alloimmunity, and tumor immunity. Gorski et al., (1994). Intensive investigative efforts have been directed to developing improved methods for monitoring the T cell repertoire to better understand, monitor, and modulate the immune system. Many of the more successful advances in T cell repertoire analysis have involved polymerase chain reaction (PCR) methodologies directed to measuring T cell receptor repertoires. See generally Cottrez et al., *J. Immunol. Methods,* 172: 85–94 (1994).

For example, Oaks et al., *Am. J. Med. Sci.,* 309(1): 26–34 (1995) reported a PCR-based method of T cell repertoire analysis comprising extracting RNA from a cell sample, synthesizing cDNA from the RNA, and amplifying aliquots of the cDNA via PCR (around 40 cycles) using family-specific Vα and Vβ oligonucleotide primers. The PCR products were analyzed by electrophoresis on a 2% agarose gel followed by Southern blotting using α-chain or β-chain constant region gene probes, wherein expression of a specific TCR Vα or Vβ family was considered positive if a distinct band was detected. The method was useful for distinguishing tissue rejection lesions versus non-rejection lesions in cardiac allograft patients. However, the Southern blot analysis provides suboptimal information about the T cell repertoire within a particular Vα or Vβ gene family. See also Dietrich et al., *Blood,* 80(9): 2419–24 (1992).

In European Patent Application No. 0 653 493 A1, filed Apr. 30, 1993, the inventors reported a PCR-based method of T cell repertoire analysis comprising extracting RNA from a cell sample, synthesizing cDNA from the RNA, and amplifying aliquots of the cDNA via PCR using family-specific Vβ oligonucleotide primers. The PCR products were then analyzed using a "single strand conformation polymorphism" (SSCP) technique wherein the PCR-amplified cDNA is separated into single strands and electrophoresed on a non-denaturing (urea-free) polyacrylamide gel, whereby DNA fragments having the same length are made further seprarable by differences in "higher order structure." Using this method, the amplified DNA from peripheral blood lymphocytes reportedly is observed generally as a "smear" whereas the detection of a single band amidst a smear is indicative of a T cell clonal expansion.

Cottrez et al., supra, reported a PCR-based method of T cell repertoire analysis comprising extracting RNA from a cell sample, synthesizing cDNA from the RNA using oligo-dT primers, and amplifying aliquots of the cDNA via PCR (around 25 cycles) using family-specific Vβ oligonucleotide primers. The PCR products were analyzed on a DNA sequencer and reportedly contained 6–11 discrete fragment peaks spaced by 3 base pairs in length, representing "all" various sizes of the CDR3 region. See also Gorski et al., *J. Immunol.,* 152: 5109–5119 (1994).

Puisieux et al., *J. Immunol.,* 153: 2807–18 (1994), reported a PCR-based method of T cell repertoire analysis comprising determining VDJ junction size patterns in twenty-four human TCR Vβ subfamilies. The TCR Vα subfamilies were not characterized. These investigators employed the method to analyze T cells infiltrating sequential malignant melanoma biopsies for the presence of clonal expansions, and detected such expansions over a more or less complex polyclonal background. Their study highlights the utility of T cell repertoire analysis methods for monitoring neoplastic conditions and treatments for such conditions.

The method of T cell repertoire analysis of Puisieux et al. reportedly includes the steps of extracting RNA from cells, synthesizing cDNA from the RNA using oligo-(dT) primers, and amplifying aliquots of the cDNA via PCR using family-specific Vβ oligonucleotide primers. Potential clonal expansions in the PCR products were tentatively identified in families where a single fluorescence peak (on a sequencing gel) corresponded to 40% of the total fluorescence intensity of all of the peaks in the family. To "refine" the T cell repertoire analysis, a second set of Vβ family-specific PCR reactions were conducted and then aliquots from each of the PCR reactions of interest were further subjected to primer extension "run off" reactions using a fluorophore labelled Cβ primer and/or using thirteen Jβ-family-specific, fluorophore-labelled Jβ primers. The run-off reaction products were then analyzed on additional sequencing gels.

The same investigative group has more recently elaborated on their T cell repertoire analysis methods. See Pannetier et al., *Immunol. Today,* 16: 176–181 (1995). The group reports that the Vβ families are easier to analyze by PCR than Vα families. Nonetheless, their Vβ analysis methods involve twenty-five Vβ family-specific PCR amplifications (each of which yields an average of eight peaks), twenty-five Cβ "run-off" reactions, and 325 Jβ "run-off" reactions (25 Vβ×13 Jβ=325). Each "run-off" reaction is analyzed by electrophoresing an aliquot on a polyacrylamide gel. See also Cochet et al., *Eur. J. Immunol.,* 22: 2639–2647 (1992) (wherein the same investigative group reports the earlier use of a similar method to analyze the T cell repertoire in mice); and Dietrich et al., *Blood,* 84(8): 2815–20 (1994) (demonstrating the utility of T cell repertoire analysis methods for monitoring tissue transplant patients for graft-versus-host disease). A long felt need exists for more rapid methods of T cell repertoire analysis, e.g., methods wherein fewer PCR reactions and electrophoresis reactions are required, wherein putative peaks representing clonal expansion events are more rapidly identified, and wherein the need to optimize interfamily PCR conditions is reduced or eliminated. Moreover, a long felt need exists for methods of T cell repertoire analysis which provide an analysis of TCR Vα chains. Preferably, the more rapid methods provide sensitivity greater than or equal to existing methods in their ability to detect clonal expansion events, including clonal expansions of T cells whose T cell receptor comprises an alpha-chain and/or beta-chain having a low-prevalence CDR3 length.

SUMMARY OF THE INVENTION

The present invention solves one or more of the aforementioned needs by providing a novel method of analyzing the T cell repertoire in a mammal, and more particularly in a human. The method may be practiced alone or combined with prior art techniques (e.g., "run-off" reaction techniques, DNA cloning and sequencing techniques, and the like). In a related aspect, the invention provides a kit of materials useful for performing the method of the invention.

For example, in one aspect, the invention provides a method of assaying for a T cell immunoproliferative condition in a human individual comprising the steps of: (a) obtaining cells from the individual; (b) generating an assay intrafamily gene fragment length profile from the cells for a T cell receptor (TCR) α-chain variable region gene family (Vα); and (c) comparing the assay profile of step (b) to a control intrafamily gene fragment length profile derived from blood cells of a healthy human subject, to determine a presence or an absence of a gene fragment length that is more prevalent in the assay profile than the control profile, wherein the control profile is for the same variable region gene family as the assay profile, and wherein the presence of a gene fragment length that is more prevalent in the assay profile than the control profile is correlated to a T cell immunoproliferative condition.

By "a T cell immunoproliferative condition" is meant a biological state wherein T lymphocytes of an individual proliferate in response to an antigenic stimulus, or a neoplastic state wherein T cells proliferate autonomously. Thus, immunoproliferative conditions include: a bacterial infection, a viral infection, or other parasitic infection, wherein T lymphocytes proliferate as an immune response to the infection; a vaccination, wherein T cells proliferate in response to an intentionally-introduced antigen; neoplastic conditions (e.g., cancerous tumors wherein tumor-infiltrating lymphocytes proliferate); auto-immune disorders; allograft rejection of transplanted cells; and autonomous T cell profliferation in T cell neoplasia. In preferred embodiments, the method is for assaying for T cell immunoproliferative conditions that are autoimmune, alloimmune, infectious conditions, or neoplastic conditions.

The method includes the step (a) of obtaining cells from the individual. These cells may be derived in any manner from any source, so long as the cell sample contains T lymphocytes. Thus, irrespective of the immunoproliferative condition, the peripheral blood is a preferred source for obtaining cells from the individual. In another preferred embodiment, the cells are derived from a fluid from the individual, the fluid selected from the group consisting of synovial fluid, cerebrospinal fluid, lymph, bronchioalveolar lavage fluid, gastrointestinal secretions, saliva, urine, and tears. In another preferred embodiment, the cells are derived from a tissue from the individual, e.g., by performing a tissue biopsy. When assaying for a particular T cell immunoproliferative condition the selection of appropriate cell sources will be apparent to those of ordinary skill. For example, to assay for autoimmune disorders affecting the joints (e.g., rheumatoid arthritis), synovial fluid is a preferred fluid from which to derive cells. To assay for disorders affecting the liver (e.g., hepatitis, primary biliary cirrhosis), the liver is a preferred tissue from which to derive cells.

The method further includes the step (b) of generating an assay intrafamily gene fragment length profile from the cells for a T cell receptor (TCR) α-chain variable region gene family (Vα). As described below in greater detail, an "intrafamily gene fragment length profile" for a particular variable region gene family contains at least two types of information: information identifying gene fragments by their length (e.g., nucleotide length and/or a CDR3 amino acid length deduced from the nucleotide length), and information about the prevalence of each identified fragment (e.g., relative to the prevalence of other identified fragments). Preferred techniques for generating an intrafamily gene fragment length profile are set forth herein in detail. For example, in a preferred embodiment, this step in the method comprises the steps of: (i) isolating RNA from the cells; (ii) synthesizing cDNA from the RNA; (iii) subjecting the cDNA to a first polymerase chain reaction using a family-specific Vα oligonucleotide primer and a first Cα oligonucleotide primer to amplify DNA encoding T cell receptor third-complemetarity-determining-regions (TCR-CDR3) of a single Vα family; (iv) subjecting the amplified DNA of step (iii) to a second polymerase chain reaction using the family specific Vα oligonucleotide primer and a second Cα oligonucleotide primer; (v) separating DNA fragments from the second polymerase chain reaction by length; and (vi) determining a prevalence of each fragment length to provide an assay intrafamily gene fragment length profile. Preferably, completely degenerate random oligonucleotide primers are employed in the cDNA synthesis step. In both polymerase reactions, a preferred annealing temperature range (for primer annealing in each PCR cycle) is 58° to 65° C. More preferably, the annealing temperature is 60° C. The second Cα oligonucleotide primer preferably is a nested primer.

Additionally, the method of the invention includes the step (c) of comparing the assay profile of step (b) to a control intrafamily gene fragment length profile derived from blood cells of a healthy human subject, to determine a presence or an absence of a gene fragment length that is more prevalent in the assay profile than the control profile, wherein the control profile is for the same variable region gene family as the assay profile, and wherein the presence of a gene fragment length that is more prevalent in the assay profile than the control profile is correlated to a T cell immunoproliferative condition. By a "healthy human subject" is meant a human subject that is free of any apparent infectious conditions, neoplastic conditions, autoimmune conditions, or other conditions that would potentiate or suppress a T cell immune response in the subject. As set forth herein in detail, the inventors have discovered that healthy human subjects have characteristic, gaussian-like intrafamily gene fragment length profiles for substantially all Vα and Vβ gene families. Therefore, the determination of whether human subjects are healthy human subjects for the purposes of serving as a control subject in the present method preferably includes the following measures: (a) routine physical examination and investigation into a subject's medical history, to screen for infectious conditions, neoplastic conditions, autoimmune conditions, or other conditions that would potentiate or suppress a T cell immune response in the subject; and (b) determination of intrafamily gene fragment length profiles for Vα and Vβ gene families, to verify that the profiles derived from the subject have the characteristic, gaussian-like appearance (or in the case of Vβ19 and Vα29, the typical profile appearance characteristic of those families).

In a preferred embodiment, the control profile is an averaged profile derived from a plurality of single intrafamily gene fragment length profiles, wherein each of the single profiles is derived from blood cells of a healthy human subject. Exemplary averaged profiles (derived from eight healthy human subjects) are presented herein for 29 Vα gene families, which are suitable for use as control profiles for the present method. Averaged profiles derived from larger numbers of healthy subjects also are contemplated. Moreover, if the human individual being assayed is from an identifiable subpopulation (e.g. a particular race or ethnicity), then the use of an average profile derived from individuals of that subpopulation also is contemplated. In an alternative embodiment, the control profile is a profile derived from the human individual being assayed for the immunoproliferative condition, where the control profile is derived from cells obtained at a time when the human individual was known to be healthy.

By "more prevalent" is meant significantly more prevalent in a statistical sense. In other words, a fragment peak in an assay intrafamily gene fragment length profile is more prevalent than the corresponding peak in a control profile for the same variable region gene family if the peak in the assay profile is significantly more prevalent in a statistical sense, e.g., more prevalent by two or more standard deviations, and preferably by three or more standard deviations, than the corresponding peak in the control profile. For example, if a particular peak in the Vα1 control profile has an average prevalence of 15% with a standard deviation of 1.25%, then the same peak in an assay profile is classified as more prevalent according to the present method at a prevalence greater than or equal to 18.75% in the assay profile (three or more standard deviations greater than 15%). The same peak is not classified as more prevalent according to the present method at a prevalence of, e.g., 16% in the assay profile.

Where the control profile is an averaged profile derived from a plurality of single intrafamily gene fragment length profiles, then a standard deviation of the mean prevalence of each fragment length is determined using standard statistical formulas. In an alternative embodiment where the control profile is derived from the human individual being assayed for the immunoproliferative condition, the same standard formulas may be used to determine standard deviation where multiple profiles were obtained from the individual at times when the individual was healthy. If only one such profile was obtained, then the standard deviations from an averaged profile derived from healthy human subjects may be adopted for the control profile derived from the human individual being assayed for the immunoproliferative condition.

At least about 29 distinct alpha-chain variable region gene families have been identified to date in the human genome. In preferred embodiments, the method is practiced by repeating steps (b) and (c) for a plurality of Vα gene families (e.g., preferably at least 10 TCR α-chain variable region gene families; and more preferably at least 20 TCR α-chain variable region gene families. Still more preferable is a method wherein steps (b) and (c) are repeated for at least 28 or 29 TCR α-chain variable region gene families (e.g., Vα1, Vα2, Vα3, Vα4, Vα5, Vα6, Vα7, Vα8, Vα9, Vα10, Vα11, Vα12, Vα13, Vα14, Vα15, Vα16, Vα17, Vα18, Vα19, Vα20, Vα21, Vα22, Vα23, Vα24, Vα25, Vα26, Vα27, Vα28, Vα29), wherein the presence of a T cell immunoproliferative condition is correlated to a gene fragment length that is more prevalent in at least one assay profile than the corresponding control profile.

The preferred techniques described herein for generating intrafamily gene fragment length profiles provide profiles having a greater number of discreet fragment lengths than have been described in the art. Each discreet fragment length in each profile provides additional T cell repertoire information. Therefore, preferred embodiments of the method are embodiments wherein the assay profile of step (b) and the control profile of step (c) contain greater numbers of fragment lengths. More particularly, in one preferred embodiment the control profile contains at least 8 fragment lengths. In a more preferred embodiment, the control profile contains at least 10 fragment lengths. For selected Vα families, control profiles of even greater numbers of fragment lengths (e.g., 11, 12, 13, 14, 15, 16, 17, or more) are preferred.

Optionally, the method further includes DNA cloning and/or sequencing procedures for verifying that an immunoproliferative condition identified in an individual is a monoclonal or oligoclonal T cell expansion.

The T cell receptor of αβ T cells contains a β-chain as well as an α-chain, and analysis of intrafamily gene fragment lengths for TCR β-chain variable region gene families also provides useful indicia of T cell immunoproliferative conditions. Thus, in a related aspect, the invention provides a method of assaying for a T cell immunoproliferative condition in a human individual comprising the steps of: (a) obtaining cells from the individual; (b) generating an assay intrafamily gene fragment length profile from the cells for a T cell receptor (TCR) β-chain variable region gene family (Vβ); and (c) comparing the assay profile of step (b) to a control intrafamily gene fragment length profile of at least 12 fragment lengths derived from blood cells of a healthy human subject, to determine a presence or an absence of a gene fragment length that is more prevalent in the assay profile than the control profile, wherein the control profile is for the same variable region gene family as the assay profile, and wherein the presence of a gene fragment length that is more prevalent in the assay profile than the control profile is correlated to a T cell immunoproliferative condition.

By "a T cell immunoproliferative condition" is meant a biological state wherein T lymphocytes of an individual proliferate in response to an antigenic stimulus, as described more fully above. The cells obtained according to step (a) may be derived in any manner from any source (e.g., bodily tissues or fluids), as described above, so long as the cell sample contains T lymphocytes.

The method includes the step (b) of generating an assay intrafamily gene fragment length profile from the cells for a T cell receptor (TCR) β-chain variable region gene family (Vβ). Preferred techniques for generating an intrafamily gene fragment length profile are set forth herein in detail. For example, in a preferred embodiment, this step in the method comprises the steps of: (i) isolating RNA from the cells; (ii) synthesizing cDNA from the RNA; (iii) subjecting the cDNA to a polymerase chain reaction using a family-specific Vβ oligonucleotide primer to amplify DNA encoding TCR-CDR3 of a single Vβ gene family; (iv) separating DNA fragments from the polymerase chain reaction by length; and (v) determining a prevalence of each fragment length to provide an assay intrafamily gene fragment length profile. In a preferred embodiment, a labelled Cβ oligonucleotide primer is employed in the PCR reaction.

The term "β-chain variable region gene family (Vβ)" is meant to include distinct Vβ"subfamilies" (e.g., Vβ13.1 and Vβ13.2; Vβ5.1 and Vβ5.2; and the like). At least about 26 distinct beta-chain variable region gene families (including subfamilies) have been identified to date in the human genome. In preferred embodiments, the method is practiced by repeating steps (b) and (c) for a plurality of Vβ gene families (e.g., preferably at least 10 TCR β-chain variable region gene families; and more preferably at least 20 TCR β-chain variable region gene families. Still more preferable is a method wherein steps (b) and (c) are repeated for at least 25 or 26 TCR β-chain variable region gene families (e.g., Vβ1, Vβ2, Vβ3, Vβ4, Vβ5.1, Vβ5.2-3, Vβ66.1-3, Vβ7, Vβ8, Vβ9, Vβ10, Vβ11, Vβ12, Vβ13.1, Vβ13.2, Vβ14, Vβ15, Vβ16, Vβ17, Vβ18, Vβ19, Vβ20, Vβ21, Vβ22, Vβ23, Vβ24), wherein the presence of a T cell immunoproliferative condition is correlated to a gene fragment length that is more prevalent in at least one assay profile than the corresponding control profile.

The preferred techniques described herein for generating intrafamily gene fragment length profiles for β-chain variable region gene families provide profiles having a greater number of discreet fragment lengths than have been described for other methods in the art, and preferred embodiments of the method are embodiments wherein the assay profile of step (b) and the control profile of step (c) contain greater numbers of fragment lengths. More particularly, in one preferred embodiment the control profile contains at least 13 or 14 fragment lengths. For selected Vβ families, control profiles of even greater numbers of fragment lengths (e.g., 15, 16, 17, 18, 19, 20, 21, 22, or more) are preferred.

In a preferred embodiment, the control profile is an averaged profile derived from a plurality of single intrafamily gene fragment length profiles, wherein each of the single profiles is derived from blood cells of a healthy human subject. Exemplary averaged profiles (derived from eight healthy human subjects) are presented herein for 25 Vβ gene families, which are suitable for use as control profiles for the present method.

In yet another aspect, the invention provides a method of assaying for a T cell immunoproliferative condition in a human individual wherein both Vα and Vβ gene families are analyzed. For example, the invention includes a method of assaying for a T cell immunoproliferative condition in a human individual comprising the steps of: (a) obtaining cells from the individual; (b) generating an assay intrafamily gene fragment length profile from the cells for a T cell receptor (TCR) β-chain variable region gene family (Vβ); (c) comparing the assay profile of step (b) to a control intrafamily Vβ gene fragment length profile of at least 12 fragment lengths derived from blood cells of a healthy human subject, to determine a presence or an absence of a gene fragment length that is more prevalent in the assay profile than the control Vβ profile, wherein the control Vβ profile is for the same variable region gene family as the assay profile; (d) generating an assay intrafamily gene fragment length profile from the cells for a TCR α-chain variable region gene family (Vα); (e) comparing the assay profile of step (d) to a control intrafamily Vα gene fragment length profile derived from blood cells of a healthy human subject, to determine a presence or an absence of a gene fragment length that is more prevalent in the assay profile of step (d) than the control Vβ profile, wherein the control Vα profile is for the same variable region gene family as the assay profile of step (d), and wherein a T cell immunoproliferative condition is correlated to (i) the presence of a gene fragment length that is more prevalent in the assay profile of step (b) than the control Vβ profile of step (c), and (ii) the presence of a gene fragment length that is more prevalent in the assay profile of step (d) than the control Vα profile. In a preferred embodiment, steps (b) and (c) are repeated for 25 or 26 TCR β-chain variable region gene families and steps (d) and (e) are repeated for 28 or 29 TCR α-chain variable region gene families, wherein a T cell immunoproliferative condition is correlated to (i) the presence of a gene fragment length that is more prevalent in at least one assay profile of step (b) than the corresponding control Vβ profile of step (c), and (ii) the presence of a gene fragment length that is more prevalent in at least one assay profile of step (d) than the corresponding control Vα profile. As described herein in greater detail, the invention facilitates significant savings in time and materials because, in a preferred embodiment, twenty-five Vβ intrafamily gene fragment length profiles and twenty-nine Vα intrafamily gene fragment length profiles can be derived from a single electrophoresis procedure using, e.g., twenty-nine lanes on a single polyacrylamide gel.

In a related aspect, the invention provides a method wherein intrafamily gene fragment length profiles are generated using cells obtained at at least two different times from the same individual, to monitor changes in the profiles for various purposes. For example, the invention includes a method for monitoring the therapeutic efficacy of an immunomodulatory treatment comprising the steps of: (a) obtaining cells from a human subject in need of an immunomodulatory treatment for a disorder; (b) generating a first intrafamily gene fragment length profile from the cells for a TCR variable region gene family selected from the group consisting of TCR beta-chain variable region gene families and TCR alpha-chain variable region gene families; (c) correlating a discreet gene fragment length within the first intrafamily gene fragment length profile to a T cell proliferative response to the disorder; (d) determining a pretreatment gene fragment length prevalence for the discreet gene fragment length relative to the prevalence of all gene fragment lengths in the first intrafamily gene fragment length profile; (e) treating the human individual with the immunomodulatory treatment for the disorder; (f) obtaining a cell sample from the human individual after initiating treatment of the human individual according to step (e); (g) generating a second intrafamily gene fragment length profile from the cell sample of step (f) for the TCR variable region gene family selected in step (b); (h) determining a treatment gene fragment length prevalence for the discreet gene fragment relative to the prevalence of all gene fragment lengths in the second profile; (i) comparing the treatment gene fragment length prevalence of step (h) with the pretreatment gene fragment length prevalence of step (d), wherein: (1) a treatment gene fragment length prevalence greater than a pre-treatment prevalence is correlated to an immunoproliferative response to the treatment of step (e), and (2) a treatment gene fragment length prevalence less than a pretreatment gene fragment length prevalence is correlated to an immunosuppressive response to the treatment of step (e). In a preferred embodiment, the method steps are repeated for a plurality of TCR variable region gene families (Vα and/or Vβ).

By "disorder" is meant a disease or other physical condition involving T cells (e.g., where T cells are implicated in the body's immune response to the disorder; where T cells and/or T cell proliferation have a causative role in the disorder; and/or wherein T cell anergy or immunodeficiency is associated with the disorder). Such disorders include but are not limited to autoimmune diseases, neoplastic diseases, infectious diseases, hypersensitivity, transplantation and graft-versus-host disease, and degenerative diseases. Autoimmune diseases include but are not limited to rheumatoid arthritis, type I diabetes, juvenile rheumatoid arthritis, multiple sclerosis, thyroiditis, myasthenia gravis, systemic lupus erythematosus, polymyositis, Sjogren's syndrome, Grave's disease, Addison's disease, Goodpasture's syndrome, scleroderma, dermatomyositis, pernicious anemia, autoimmune atrophic gastritis, primary biliary cirrhosis, and autoimmune hemolytic anemia. Neoplastic diseases include but are not limited to lymphoproliferative diseases such as leukemias, lymphomas, Non-Hodgkin's lymphoma, and Hodgkin's lymphoma, and cancers such as cancer of the breast, colon, lung, liver, pancreas, skin, etc. Infectious diseases include but are not limited to viral infections caused by viruses such as HIV, HSV, EBV, CMV, Influenza, Hepatitis A, B, or C; fungal infections such as those caused by the yeast genus Candida; parasitic infections such as those caused by schistosomes, filaria, nematodes, trichinosis or protozoa such as trypanosomes causing sleeping sickness, plasmodium causing malaria or leishmania causing leishmaniasis; and bacterial infections such as those caused by mycobacterium, corynebacterium, or staphylococcus. Hypersensitivity diseases include but are not limited to Type I hypersensitivities such as contact with allergens that lead to allergies, Type II hypersensitivities such as those present in Goodpasture's syndrome, myasthenia gravis, and autoimmune hemolytic anemia, and Type IV hypersensitivities such as those manifested in leprosy, tuberculosis, sarcoidosis and schistosomiasis. Degenerative diseases include but are not limited to Parkinson's disease, Alzheimer's disease, and atherosclerosis.

By "immunomodulatory treatment" is meant a treatment regimen that is to be applied/administered to a subject suffering from a disorder for the purpose of potentiating (e.g., for infectious diseases, cancer, or immunodeficiency) or suppressing (e.g., for hypersensitivity, autoimmune disorders, or alloimmune disorders) a T cell immune response to the disorder. In one preferred embodiment, the immunomodulatory treatment is an immunoproliferative treatment for a disorder selected from the group consisting of neoplasia and infection. In another preferred embodiment, the immunomodulatory treatment is an immunosuppressive treatment for a disorder selected from the group consisting of an autoimmune disorder and an allograft rejection disorder. In yet another embodiment, the immunomodulatory treatment is a vaccine for the prophylactic treatment of a disorder.

The method includes the step (c) of "correlating a discreet gene fragment length within the first intrafamily gene fragment length profile to a T cell proliferative response to the disorder." As explained in greater detail below, such a correlation is established by identifying a fragment peak whose prevalence in the intrafamily gene fragment length profile correlates with the intensity of a T cell proliferative response to the disorder.

In another aspect, the invention provides a method of assaying for a presence of an immunogenic condition in a tissue of a human individual comprising the steps of: (a) isolating a tissue sample from the individual; (b) generating an intrafamily gene fragment length profile from the tissue sample for one of: (i) a TCR beta-chain variable region gene family, or (ii) a TCR alpha-chain variable region gene family; (c) isolating peripheral blood lymphocytes from the individual; (d) generating an intrafamily gene fragment length profile from the peripheral blood lymphocytes for the same gene family as step (b); and (e) comparing the profile of step (b) and the profile of step (d) to determine a presence or an absence of a discreet gene fragment more prevalent in the profile of step (b) than the profile of step (d), wherein the presence of an immunogenic condition in the tissue correlates to the presence of the discreet gene fragment. In one preferred embodiment, the profile of step (d) is a profile of at least 11 fragment lengths for a TCR α-chain variable region gene family. In another preferred embodiment, the profile of step (d) is a profile of at least 14 fragment lengths for a TCR β-chain variable region gene family. In yet another embodiment, the method steps (b), (d), and (e) are repeated for a plurality of TCR variable region gene families (Vα and/or Vβ.

Yet another aspect of the invention is a kit useful for practicing a method described herein. For example, the invention includes a kit for performing intrafamily T Cell receptor (TCR) repertoire analysis comprising, in association: a family-specific oligonucleotide primer for PCR amplification of a single TCR variable-region gene family; and an intrafamily gene fragment length profile for the TCR variable-region gene family derived from blood cells of a healthy human subject. In one preferred embodiment, the intrafamily gene fragment length profile is an averaged profile derived from a plurality of intrafamily gene fragment length profiles derived from blood cells of healthy human subjects. The kit may further comprise additional materials to facilitate intrafamily T Cell receptor repertoire analysis, such as a PCR buffer, a solution containing dNTP's, a thermostable DNA polymerase enzyme, a T cell receptor constant region oligonucleotide primer, computer hardware and/or software to automate analysis of polyacrylamide gel electrophoresis data, and the like.

The single TCR variable region gene family recited in the kit is preferably a Vα gene family or a Vβ gene family. Where the variable region gene family is a Vα gene family, the intrafamily gene fragment length profile of the kit preferably contains at least 10, or more preferably at least 11, fragment lengths. A preferred kit comprises a plurality (preferably twenty-eight or twenty-nine or more) of family-specific oligonucleotide primers for PCR amplification of a plurality of TCR Vα gene families; and intrafamily gene fragment length profiles of at least 8 fragment lengths for each of the TCR Vα gene families, wherein each of the profiles is derived from blood cells of a healthy human subject.

Where the variable region gene family is a Vβ gene family, the intrafamily gene fragment length profile of the kit preferably contains at least 13 or 14 fragment lengths. A preferred kit comprises a plurality (preferably twenty-five or more) of family-specific oligonucleotide primers for PCR amplification of a plurality of TCR Vβ gene families; and intrafamily gene fragment length profiles of at least 12 fragment lengths for each of the TCR Vβ gene families, wherein each of the profiles is derived from blood cells of a healthy human subject.

Numerous other aspects and advantages of the present invention will be apparent upon the following detailed description thereof, reference being made to the drawing wherein:

BRIEF DESCRIPTION OF THE DRAWING

FIG. 3B is a tabulation of the CDR3 fragment length prevalences (expressed as percentages) depicted in the histograms of FIG. 3A for twenty-five Vβ families and subfamilies. The bottom rows of the tabulation depict the averaged prevalence of each CDR3 fragment length in all twenty-five Vβ gene families; the standard deviation; and standard error reflected in these averages.

FIG. 9B is a tabulation of the CDR3 fragment length prevalences (expressed as percentages) depicted in the histograms of FIG. 8A for twenty-eight Vα families and subfamilies. The bottom rows of the tabulation depict the averaged prevalence of each CDR3 fragment length in all twenty-eight Vα gene families; the standard deviation; and standard error reflected in these averages.

DETAILED DESCRIPTION

Figure 1:
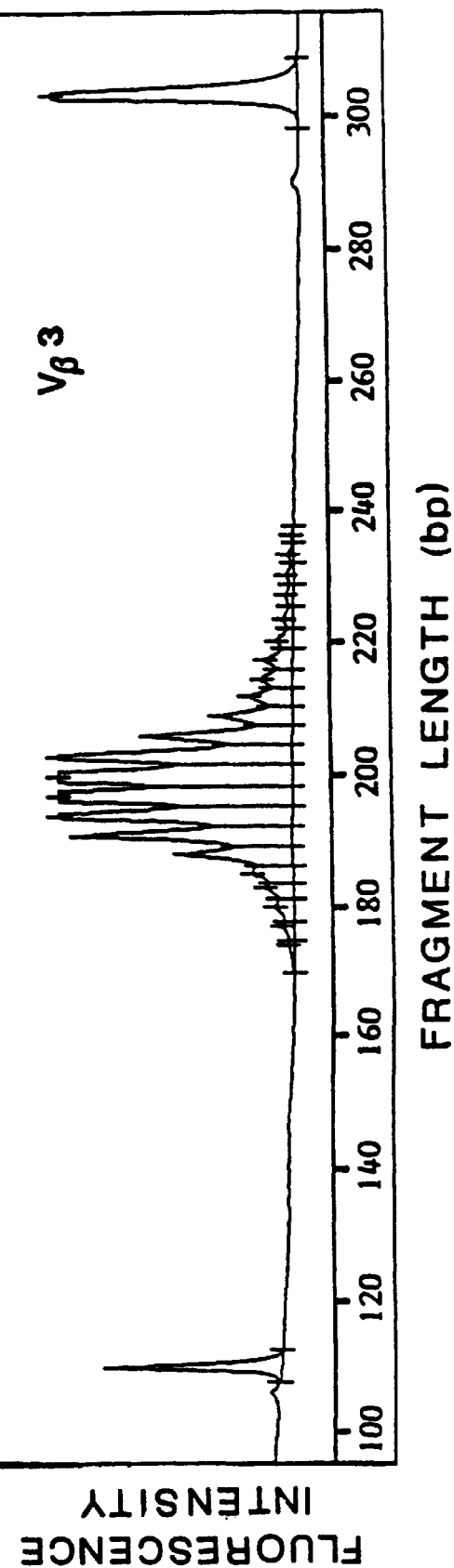
FIG. 1 depicts an intrafamily gene fragment length profile for the Vβ3 gene family, the profile having been derived according to procedures outlined herein from the blood of a single healthy individual. A one microliter aliquot from a thirty-cycle PCR expansion of Vβ3 fragments (expanded with Vβ3 and fluoresceinated-Cβ primers) was electrophoresed on a denaturing polyacrylamide gel. Peak areas (measured as fluorescence intensity) are depicted graphically as a function of fragment length (in base pairs). Peaks measured at 110 and 303 nucleotides are DNA size standards. Vertical markers within the profile were placed by the DNA Fragment Manager™ 1.1 software program in order to measure peak length and area.

The present invention provides a method and a kit of materials useful for characterizing the T cell repertoire in a mammal (e.g., murine, bovine, porcine, canine, feline, primate, etc.), especially in a human. Procedures which permit the characterization of a T cell repertoire have important clinical applications in numerous medical disciplines, since T cell immune responses manifest themselves in infectious conditions (viral, bacterial, fungal, microbial, etc.), allergies, autoimmune disorders, allograft rejection disorders, neoplastic disorders, etc.

By way of example, the ability to characterize an individual's T cell repertoire has innumerable diagnostic applications, because many medical disorders are detectable as T cell immunoproliferative conditions. For example, an infection by most pathogens generates an immune response wherein one or more T cells recognize the pathogen (by virtue of pathogen-T cell receptor complimentarity) and thereby are stimulated to undergo clonal expansion to fight the pathogen. Such a T cell clonal expansion is a T cell immunoproliferative condition. A method for characterizing an individual's T cell repertoire which detects a T cell clonal expansion (e.g., which detects a T cell immunoproliferative condition) is useful for diagnosing the presence of the immunoproliferative condition.

The ability to characterize an individual's T cell repertoire has diagnostic applications for medical disorders that are detectable as immunosuppressive conditions, too. For example, certain infections and other antigens are known to suppress normal T cell development and expansion. Such conditions are immunosuppressive conditions. A method for characterizing an individual's T cell repertoire which detects a T cell immunosuppressed state (e.g., detects a below-normal population of certain T cells) is useful for diagnosing the presence of the immunosuppressed condition.

The ability to characterize an individual's T cell repertoire has practical applications for monitoring treatments for innumerable disorders, because the efficacy of many treatments lies in their ability to modulate (to potentiate or to suppress) an immune response. For example, when an individual is afflicted with many disorders (e.g., neoplastic disorders, chronic infection), it is desirable to provide a treatment designed to potentiate the individual's own immune response to the disorder, to suppress or overcome the disorder (i.e., it is desirable to provide an immunoproliferative treatment). A method for characterizing an individual's T cell repertoire which detects a T cell immunoproliferative response to a treatment is useful for monitoring the efficacy of such a treatment. A first characterization of the T cell repertoire as it exists prior to the treatment is compared to a second characterization of the T cell repertoire during or after the treatment to detect the presence or absence of a T cell immunoproliferative response to the treatment. Characterizations may be repeated to continue to monitor the treatment and/or to monitor for a relapse of the disorder between treatments.

Vaccines are administered as prophylactic treatments to potentiate an immune response to an antigen. A method for characterizing an individual's T cell repertoire which detects a T cell immunoproliferative response to a treatment is useful for monitoring the efficacy of such a vaccine.

For many other disorders (e.g., autoimmune disorders, graft-versus-host rejection, and others), immunosuppressive treatments are administered to suppress a T cell immune response. A method for characterizing an individual's T cell repertoire which detects a T cell immunosuppressive response to a treatment is useful for monitoring the efficacy of such a treatment. A first characterization of the T cell repertoire as it exists prior to the treatment is compared to a second characterization of the T cell repertoire during or after the treatment to detect the presence or absence of T cell immunosuppression attributable to the treatment. Characterizations may be repeated to continue to monitor the treatment and/or to monitor for a relapse of the disorder between treatments.

For the foregoing reasons, a method for rapidly characterizing every unique T cell in an individual's T cell repertoire (to determine which T cells, if any, are undergoing antigen-stimulated clonal expansion) is highly desirable. However, humans are estimated to possess, on average, as many as $1 \times 10^9$ or $10^{10}$ unique T cells (having unique T cell receptors). The present invention provides a method for characterizing an individual's T cell repertoire wherein T cells are characterized in a quantitative manner by the T cell receptor variable region gene families expressed in the T cells.

More particularly, every αβ T cell has a receptor having polypeptide segments encoded by one α-chain variable region gene segment (Vα) and one β-chain variable region gene segment (Vβ). The entire repertoire of Vα and Vβ gene segments responsible for encoding the variable regions in a human individual's αβ T cell repertoire are classifiable within about twenty-nine Vα gene families and about 26 Vβ gene families. The present invention provides a method for characterizing an individual's T cell repertoire by providing a method for determining intrafamily gene fragment length profiles for substantially all Vα and Vβ gene families. The method may be performed quickly and provides a quantity of T cell repertoire data that is sufficiently small to analyze rapidly but sufficiently detailed to detect T cell oligoclonal and monoclonal expansions (immunoproliferative conditions) and to detect immunosuppression.

More particularly, a T cell clonal expansion results in an increased prevalence of that T cell in an individual's T cell repertoire. The method described herein detects this increased prevalence as a fragment length of increased prevalence in an intrafamily gene fragment length profile. Immunosuppressive therapy or anti-T cell-neoplastic therapy which results in decreased numbers of an expanded clone is detected as a decrease in the prevalence of a gene fragment length in an intrafamily gene fragment length profile.

The present invention is further illustrated by the following examples. More particularly, Example 1 describes a procedure for determining intrafamily gene fragment length profiles for T cell receptor Vβ gene families, and provides the results of the procedure (i.e., provides intrafamily gene fragment length profiles) for substantially all known Vβ gene families, for the T cell repertoire of eight healthy human subjects. Example 2 demonstrates that random primers were unexpectedly superior to oligo-dT primers and β-chain-constant-region-specific primers for generating cDNA for use as PCR template in intrafamily gene fragment analysis. Example 3 describes a related procedure for determining intrafamily gene fragment length profiles for T cell receptor Vβ gene families. The procedure in Example 3 is improved relative to the procedure in Example 1 to enhance the efficiency, rapidity, and repeatability with which intrafamily gene fragment analysis is performed.

Example 4 describes a procedure for determining intrafamily gene fragment length profiles for T cell receptor Vα gene families, and provides the results of the procedure (i.e., provides intrafamily gene fragment length profiles) for substantially all known Vα gene families, for the T cell repertoire of eight healthy human subjects. Example 5 describes a related procedure for determining intrafamily gene fragment length profiles for T cell receptor Vα gene families. The procedure in Example 5 is improved relative to the procedure in Example 4 to enhance the efficiency, rapidity, and repeatability with which intrafamily gene fragment analysis is performed.

Example 6 describes a procedure for determining intrafamily gene fragment length profiles for twenty-five T cell receptor Vβ gene families and twenty-nine T cell receptor Vα gene families using twenty-nine lanes on a single polyacrylamide gel. This procedure thus provides savings in terms of time and materials compared to T cell repertoire analysis procedures requiring multiple polyacrylamide gel loadings for each variable region gene family that is analyzed.

Example 7 demonstrates that intrafamily gene fragment analysis procedures described in preceding examples are useful for assaying for the presence of a T cell immunoproliferative condition in a human subject. More particularly, the intrafamily gene fragment length profiles derived from a patient suffering from primary biliary cirrhosis contained discrete fragment lengths that were significantly more prevalent than the corresponding fragment lengths in control profiles for the same gene families derived from peripheral blood of healthy human subjects.

Example 8 provides a procedure for correlating a particular fragment in a particular intrafamily gene fragment length profile to a particular disorder.

EXAMPLE 1

Determination of Normal Human Intrafamily Gene Fragment Length Profiles for T Cell Receptor Vβ Gene Families The following procedure demonstrated that the intrafamily gene fragment length profiles for human T cell receptor Vβ gene families demonstrate a characteristic, gaussian-like appearance in healthy human individuals who appeared to be free of diseases, infections and immune disorders upon routine physical examination. Moreover, the procedure unexpectedly revealed that the gaussian-like profile for any particular Vβ gene family is essentially the same in each healthy human individual. Further, the procedure unexpectedly revealed that the fragment profiles for each human Vβ gene family contains 14–23 fragments, more than previously reported for alternative methods of intrafamily gene fragment analysis.

Preparation of Cells, RNA, and cDNA

Blood samples were obtained from 8 healthy donors (mean age±standard deviation: 33±6.4 years; 5 females and 3 males; all Caucasians) free from any apparent infections, diseases, or immune disorders. A ninth, apparently healthy donor later was rejected because of anomalous results. Peripheral blood mononuclear cells (PBMC) were isolated from the blood samples by density sedimentation (LSM, Organon Teknika, Durham, N.C.) from 10 ml of whole blood.

Total RNA was extracted from 2 to 3 million of the isolated PBMC using RNAzol™ B (Tel-Test, Friendswood, Tex.) and re-suspended in 30 μl DEPC water. RNA concentration was determined by spectrophotometry (Spectronic 1201, Milton Roy, Rochester, N.Y.).

First strand cDNA (33 μl) from about 20 percent of the purified RNA (corresponding to RNA from about $2 \times 10^5$ T lymphocytes) was synthesized from 1.0 μg total RNA using the first strand cDNA Kit (Pharmacia, Piscataway, N.J.) and random hexamer primers, according to the manufacturer's instructions.

PCR Amplification of First Strand cDNA

Each cDNA sample was used to provide template for twenty-nine PCR reactions. More particularly, twenty-seven separate reactions were performed to amplify TCR Vβ gene families (Vβ1 through Vβ24, including the subfamilies, Vβ5.1, 5.2-3 and Vβ13.1, 13.2) from the cDNA. For these twenty-seven reactions, twenty-seven family-specific 5' Vβ oligonucleotide primers were employed, all of which have been described in the art and are set forth in Table I. A single, fluoresceinated 3' primer that binds to the Cβ region was employed in each of the twenty-six reactions (Table I (F=fluorescein label)). In the remaining two PCR reactions, the human β- actin locus and TCR Cβ locus were independently amplified as controls. To amplify the β-actin locus, β-actin 5' and 3' primers according to Clonetech (Palo Alto, Calif.) were employed; to amplify the TCR Cβ control, Cβ5'-FTCCCACACCCAAAAGGCCACACTG-3' (SEQ ID NO: 60), and 3' (TCβ2) 5'-TCGTCGACCCCACTGTGCACCTCCTTCCC-3' (SEQ ID NO: 61) according to Robinson, *J. Immunol.*, 146: 4392 (1991) were employed.

TABLE I

PCR OLIGONUCLEOTIDE PRIMERS FOR TCR-CDR3
INTRAFAMILY Vβ GENE FRAGMENT ANALYSIS

| Primer♦ | Primer Sequence (5' to 3')⌂ | 5' Binding Position✿ | Distance to Residue 96 (nucleotides) | SEQ ID NO: |
|---|---|---|---|---|
| B1. Vβ1 | GCA CAA CAG TTC CCT GAC TTG CAC | 253 | 87 | 1 |
| B2. Vβ2 | TCA TCA ACC ATG CAA GCC TGA CCT | 248 | 89 | 2 |
| B3. Vβ3 | GTC TCT AGA GAG AAG AAG GAG CGC | 253 | 87 | 3 |
| B4. Vβ4 | ACA TAT GAG AGT GGA TTT GTC ATT | 226 | 123 | 4 |
| B5. Vβ5.1 | ATA CTT CAG TGA GAC ACA GAG AAA C | 201 | 139 | 5 |
| B6. Vβ5.2-3 | TTC CCT AAC TAT AGC TCT GAG CTG | 158*† | 78 | 6 |
| B7. Vβ6.1-3 | AGG CCT GAG GGA TCC GTC TC | 206 | 81 | 7 |
| B8. Vβ7 | CCT GAA TGC CCC AAC AGC TCT C | 135*‡ | 87 | 8 |
| B9. Vβ8 | ATT TAC TTT AAC AAC AAC GTT CCG | 196 | 147 | 9 |
| B10. Vβ9 | CCT AAA TCT CCA GAC AAA GCT CAC | 114 | 87 | 10 |
| B11. Vβ10 | CTC CAA AAA CTC ATC CTG TAC CTT | 264 | 79 | 11 |
| B12. Vβ11 | TCA ACA GTC TCC AGA ATA AGG ACG | 247 | 93 | 12 |
| B13. Vβ12 | AAA GGA GAA GTC TCA GAT | 211* | 114 | 13 |
| B14. Vβ13.1 | CAA GGA GAA GTC CCC AAT | 226 | 114 | 14 |
| B15. Vβ13.2 | GGT GAG GGT ACA ACT GCC | 208 | 132 | 15 |
| B16. Vβ14 | GTC TCT CGA AAA GAG AAG AGG AAT | 253 | 87 | 16 |
| B17. Vβ15 | AGT GTC TCT CGA CAG GCA CAG GCT | 250 | 90 | 17 |
| B18. Vβ16 | AAA GAG TCT AAA CAG GAT GAG TCC | 103* | 135 | 18 |
| B19. Vβ17 | CAG ATA GTA AAT GAC TTT CAG | 204 | 135 | 19 |
| B20. Vβ18 | GAT GAG TCA GGA ATG CCA AAG GAA | 223 | 120 | 20 |
| B21. Vβ19a | CAA TGC CCC AAG AAC GCA CCC TGC | 274* | 84 | 21 |
| B22. Vβ19b | CTC AAT GCC CCA AGA ACG CAC | 272* | 86 | 22 |
| B23. Vβ20 | AGC TCT GAG GTG CCC CAG AAT CTC | 163*§ | 114 | 23 |
| B24. Vβ21 | TCC AAC CTG CAA GGC TTG ACG ACT | 318 | 50 | 24 |
| B25. Vβ22 | AAG TGA TCT TGC GCT GTG TCC CCA | 110 | 232 | 25 |
| B26. Vβ23 | GCA GGG TCC AGG TCA GGA CCC CCA | 115* | 175 | 26 |
| B27. Vβ24 | CCC AGT TTG GAA AGC CAG TGA CCC | 95 | 245 | 27 |
| B28. 3'Cβ | F-TTC TGA TGG CTC AAA CAC | 835 | | 28 |

♦Primers B1–B21, B23 and B28 were described previously in Choi et al., Proc. Natl. Acad. Sci. (USA), 86:8941 (1989). Primer B22 was described previously in Hall and Finn, BioTechniques 13:248 (1992). Primers B24–B27 were described previously in Genevée et al., Eur. J. Immunol., 22:1261 (1992).
⌂Undelined nucleotides are mismatches introduced to reduce cross-hybridization to other Vβ subfamilies.
✿Nucleotides are numbered beginning with the putative translation initiation site, ATG, as reported in Genevée, et at. (1992), except where otherwise noted.
*Numbering starts from the first nucleotide position in the sequence.
†Measured from Vβ5.2
‡Measured from Vβ7.1
§Measured from Vβ21.1

Each PCR reaction consisted of 1.0 µl 10× buffer (10× buffer was from Boehringer Mannhiem and included 100 mM Tris-HCl; 15 mM MgCl$_2$; 500 mM KCl; pH 8.3 (at 20° C.)); 0.1 µl (5 U/µl) Taq polymerase (Boehringer Mannheim, Indianapolis, Ind.); 0.15 µl of a solution containing 10 mM dNTPs (dATP, dCTP, dTTP, and dGTP) (Ultrapure, Pharmacia); a 0.85 µl aliquot from the 33 µl cDNA reaction; 1.0 µl (3.0 µM) 5' end primer; 1.0 µl (3.0 µM) 3' end primer; and water to bring the final volume to 10.0 µl. A Perkin-Elmer 480 DNA thermocycler was used for PCR amplification with at least 30 cycles of denaturation at 94° C. for 45 seconds, annealing at 55° C. for 45 seconds, extension at 70° C. for 45 seconds, and extension for 10 minutes at 70° C. after the last cycle. Five microliters of PCR products from the two controls were run on 2% agarose gels (Sigma, St. Louis, Mo.) with TBE Buffer, visualized with ethidium bromide and photographed. As set forth below in greater detail, it is believed that careful selection of the proper amount of PCR reaction product to load on polyacrylamide gels contributed to the resolution of previously undiscovered gene fragments in every Vβ gene family fragment profile analyzed.

CDR3 Length Measurement

To separate PCR products by fragment length, samples from each PCR reaction were electrophoresed in 0.5 mm thick, denaturing, 6% polyacrylamide gels with a fluorescent automated DNA sequencer (A.L.F., Pharmacia). At least two DNA size (length) standards were loaded in each sample-containing lane (approx. 100 µg of each standard). The fluorescent signal from PCR products was analyzed by Fragment Manager™ 1.1 software (Pharmacia) using the following settings: peak width 10, peak height 0.5, and cluster sensitivity 0. Using this equipment and software, the fluorescence peak area and baseline are calculated automatically, and DNA fragments of the same length are detected as a single peak. In certain analyses, the cluster sensitivity setting was insufficient to establish a baseline automatically, so the baseline was adjusted manually. With these software settings, true Vβ fragment peaks were delineated from artifact by fulfilling at least 2 of the following 3 criteria: 1) fragment length separated by a multiple of 3 base pairs (i.e., one codon length) from surrounding peaks; 2) peak in contiguity with the surrounding peaks; and 3) peak area (as measured by the aforementioned equipment) greater than 50 units.

For each Vβ gene family, at least two separate PCR samples were analyzed by electrophoresis as described above. For the first run, the amount of DNA loaded (0.5–2 µl samples from the PCR reaction, taken after 30 cycles PCR) was adjusted so that the most abundant DNA peaks did not exceed the measurement limit of the fluorescence detector. For the second run, DNA was intentionally overloaded (3–5 µl samples, 35–40 cycles PCR) so that the most abundant peaks exceeded the detection limit, thereby allowing detection of a maximum number of low abundance peaks.

As a result of the protocol employed, the quantity of PCR fragments of a particular length (relative to the quantity of other fragments of other lengths in a single PCR reaction) was reflected by the fluorescence peak area determined for that particular fragment length (relative to the other fragment length peak areas). More particularly, fluorescence intensity (i.e., peak area) was a quantitative measure of Vβ gene fragments because each Vβ gene fragment from the PCR reaction was accomplished by the same Vβ primer and was labeled exactly once with the same fluorescently-labelled 3' Cβ PCR primer. Thus, the prevalence of a particular fragment length was easily determined from peak areas. Specifically, the percent area for any individual peak was obtained by dividing the individual peak area by the total of all of the (non-artifact) peak areas for a single PCR reaction. For each fragment length, percent area is a direct measurement of the prevalence of the fragment length.

For each fragment detected using the foregoing protocol, fragment length (in nucleotides) was determined from the fragment's electrophoretic mobility in the gel compared to two fluoresceinated DNA markers, Cβ and actin, and/or compared to 100 to 350 base pair standards (Pharmacia) run in the same lane. Appropriate size standards were selected to migrate faster and slower than the expected family-specific PCR products of each sample. The Pharmacia hardware and software permitted such fragment length determination in an automated manner.

CDR3 amino acid measurements were deduced from the fragment length measurements for each intrafamily gene fragment length profile, employing the formula of Rock et al., *J. Exp. Med.*, 179: 323 (1994). In particular, from each fragment length measurement, the following nucleotide lengths were subtracted: 1) 30 nucleotides, representing the conserved length (3') of the Jβ segment through the constant phenylalanine residue (5'); 2) 54 nucleotides, representing the portion of the 5' end of the Cβ gene segment amplified as a result of the Cβ PCR primer employed; and 3) the number of nucleotides measured from the 5' end of the particular Vβ primer employed to position 96 of the β chain (for each Vβ primer employed, the corresponding number of nucleotides is set forth in Table I). The resultant fragment length was divided by three to provide a CDR3 length determination (in amino acid residues).

Skew was calculated for the CDR3 fragment length distribution within each family as a measure of its deviation from a true gaussian distribution.

T Cell Cloning and TCR β Chain Sequencing

T cell clones were established from peripheral blood mononuclear cells by primary culture in microtiter wells under limiting dilution conditions in the presence of PHA and IL-2. RNA was isolated from each clonal population and used to synthesize cDNA as described above. PCR was used to expand the cDNA using Vβ family specific and Cβ primers. Cycle sequencing was performed on the expanded DNA using a single Cβ fluoresceinated primer, and automated sequencing was carried out with the A.L.F. DNA sequencer.

Results

The procedure described above provided Vβ intrafamily gene fragment profiles having from 14 to 22 or more distinct CDR3 fragment peaks. For example, FIG. 1 graphically illustrates the profile of the Vβ3 β-chain gene family from a representative healthy donor. Twenty-two CDR3 fragments from 174 through 236 nucleotides in length were distinguished as single peaks present contiguously at intervals of 2.95±0.27 nucleotides. The individual fragment lengths, corresponding peak areas, and deduced CDR3 amino acid lengths encoded by the fragments in this profile are summarized in Table II.

TABLE II

DNA fragment length, fluorescence peak area, and deduced CDR3 length in the Vβ3 family depicted in FIG. 1

| Peak # | Fragment Length (base pairs) | Peak Area | CDR# length (amino acids) |
|---|---|---|---|
| 1 | 110 | 1935 | Marker |
| 2 | 174 | 62 | 1 |
| 3 | 176.9 | 190 | 2 |
| 4 | 179.9 | 457 | 3 |
| 5 | 182.9 | 484 | 4 |
| 6 | 185.1 | 891 | 5 |
| 7 | 187.9 | 2058 | 6 |
| 8 | 190.9 | 3852 | 7 |
| 9 | 193.8 | 4828 | 8 |
| 10 | 196.8 | 6089 | 9 |
| 11 | 199.7 | 6336 | 10 |
| 12 | 202.7 | 4833 | 11 |
| 13 | 205.7 | 2654 | 12 |
| 14 | 208.7 | 1400 | 13 |
| 15 | 211.7 | 918 | 14 |
| 16 | 214.2 | 707 | 15 |
| 17 | 217.1 | 620 | 16 |
| 18 | 220.0 | 357 | 17 |
| 19 | 223.3 | 255 | 18 |
| 20 | 226.9 | 192 | 19 |
| 21 | 230 | 170 | 20 |
| 22 | 233.1 | 106 | 21 |
| 23 | 236 | 37 | 22 |
| 24 | 303 | 6290 | Marker |

TABLE III

| Vβ Family | CDR3 length (amino acids) | | |
|---|---|---|---|
| | Mean ± SD* | Median* | Skew |
| 1 | 10.1 ± 2.9 | 9.7 | 1.14 |
| 2 | 9.0 ± 2.3 | 8.7 | 0.82 |
| 3 | 9.2 ± 3.1 | 9.1 | 0.55 |
| 4 | 9.0 ± 2.8 | 8.6 | 1.04 |
| 5.1 | 9.9 ± 2.5 | 9.8 | 0.18 |
| 5.2 | 9.4 ± 2.3 | 9.3 | 0.55 |
| 6 | 10.0 ± 2.5 | 9.7 | 0.73 |
| 7 | 10.2 ± 2.3 | 10.1 | 0.15 |
| 8 | 9.7 ± 2.6 | 9.5 | 0.72 |
| 9 | 9.3 ± 2.3 | 9.2 | 0.53 |
| 10 | 11.1 ± 3.0 | 10.8 | 0.10 |
| 11 | 9.2 ± 2.6 | 9.2 | 0.23 |
| 12 | 9.5 ± 2.4 | 9.3 | 0.59 |
| 13.1 | 9.4 ± 2.2 | 9.2 | 0.73 |
| 13.2 | 9.8 ± 2.6 | 9.7 | 0.37 |
| 14 | 9.2 ± 2.6 | 9.0 | 0.49 |
| 15 | 10.3 ± 2.7 | 10.0 | 1.03 |
| 16 | 9.9 ± 2.5 | 9.8 | 0.83 |
| 17 | 9.2 ± 2.0 | 9.2 | 0.60 |
| 18 | 9.9 ± 2.4 | 9.6 | 0.75 |
| 20 | 8.8 ± 2.3 | 8.5 | 1.01 |
| 21 | 9.2 ± 2.3 | 9.0 | 1.04 |
| 22 | 10.6 ± 2.1 | 10.5 | 0.42 |
| 23 | 10.3 ± 3.0 | 10.2 | 0.14 |
| 24 | 10.5 ± 2.4 | 10.3 | 0.51 |

*Calculated from peak length and relative abundance

Figure 2A:
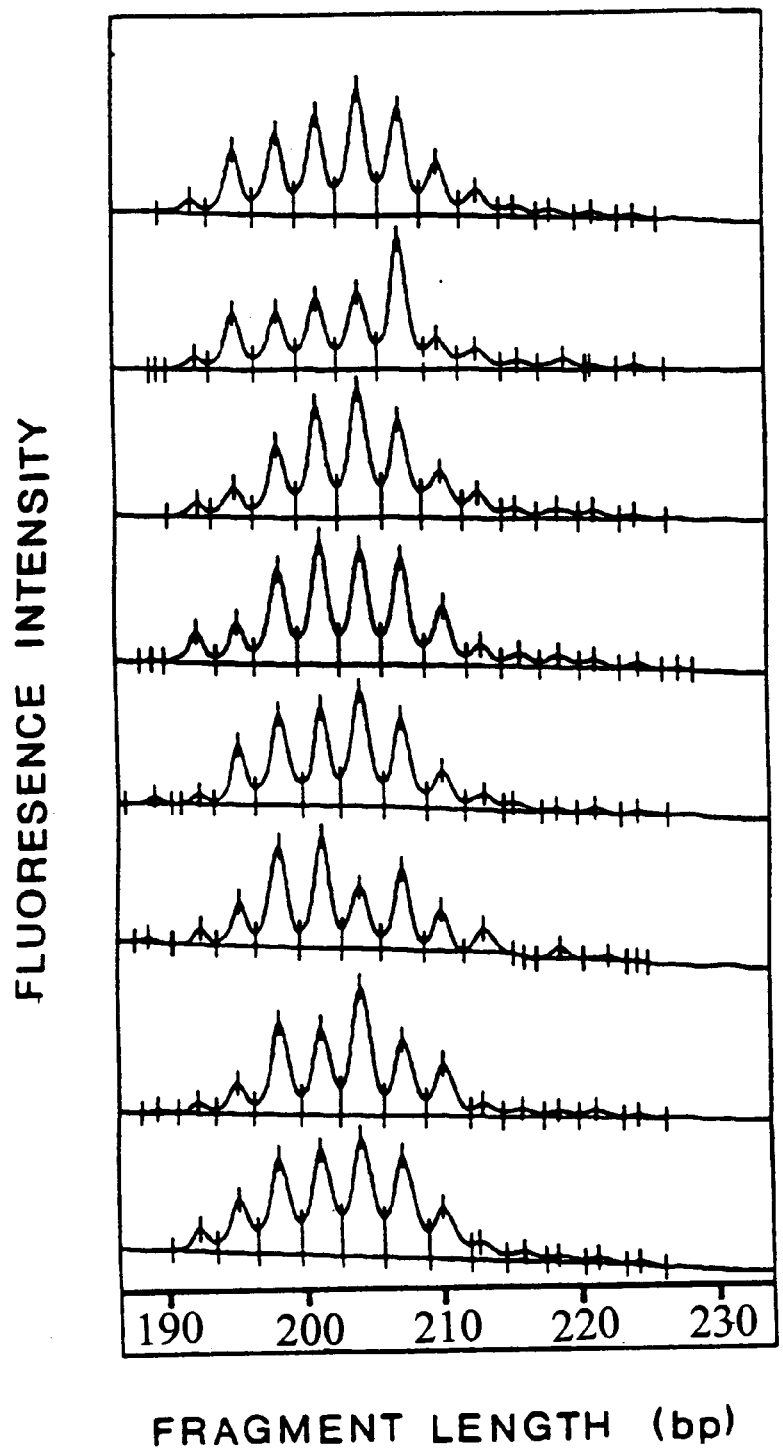
FIG. 2A depicts eight intrafamily gene fragment profiles for the Vβ15 gene family as in FIG. 1, derived from blood from eight healthy individuals. One microliter aliquots from thirty-cycle PCR expansions of Vβ15 fragments (expanded with Vβ15 and fluoresceinated-Cβ primers) were electrophoresed on denaturing polyacrylamide gels.
Figure 2B:
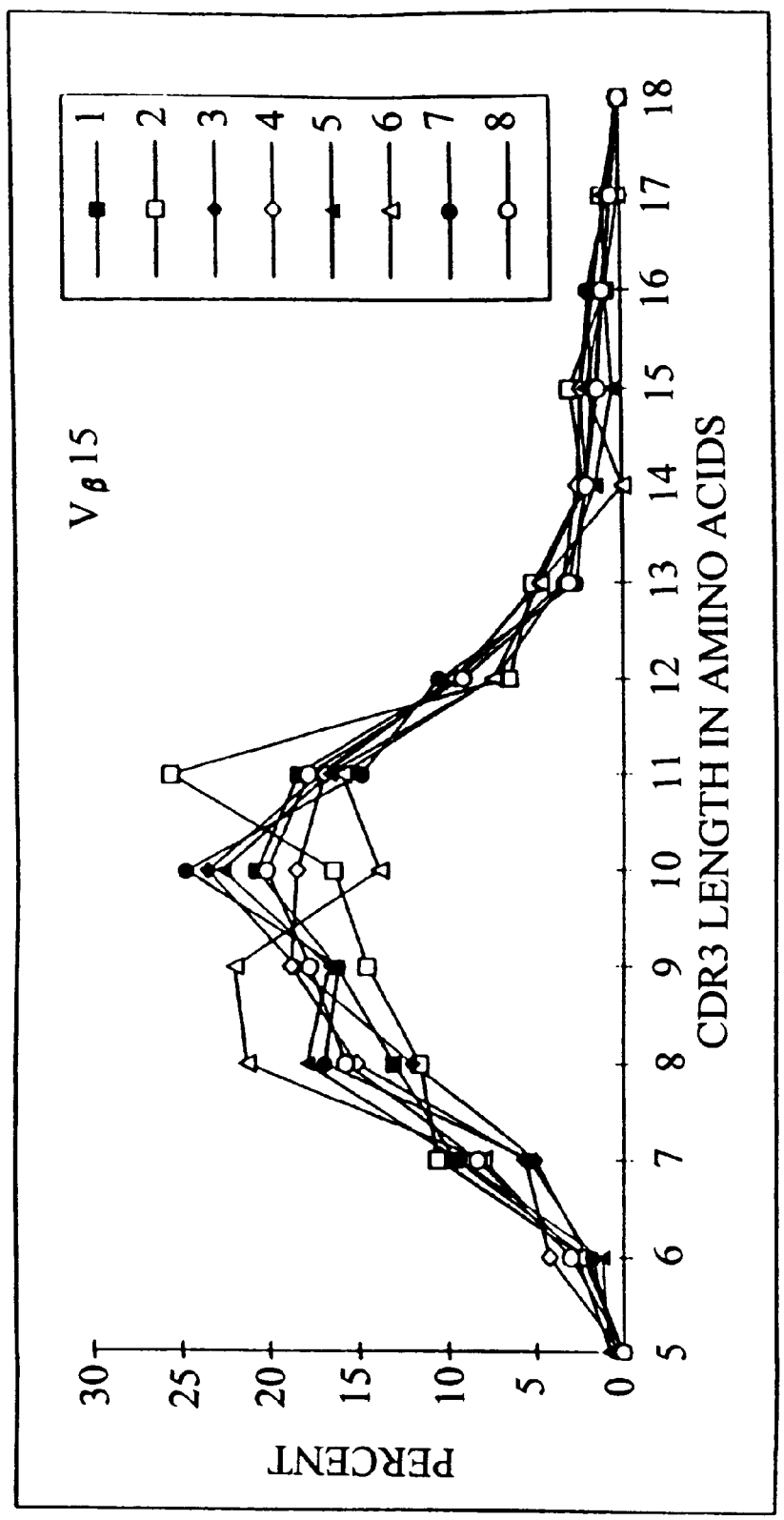
FIG. 2B depicts the frequency distribution (prevalence) of each deduced CDR3 length from the fragment peak area and length data depicted in FIG. 2A. Each symbol depicts the frequency distribution for a different donor (numbered 1–8). The percent area for any individual peak from each donor was obtained by dividing the individual peak area by the total peak area for that Vβ15 family.

Significantly, the intrafamily gene fragment length profiles were consistently gaussian-like in appearance for each of the eight healthy blood donors, irrespective of the Vβ gene family analyzed. Moreover, for any particular Vβ gene family, the gaussian-like distribution was strikingly similar for all 8 healthy donors, as illustrated in FIGS. 2A and 2B for the Vβ15 fragment profiles. In other words, not only were the profiles for a given Vβ gene family gaussian-like in general appearance for each individual, but the prevalences of each CDR3 peak within the profiles were remarkably similar from individual to individual.

Figure 3A:
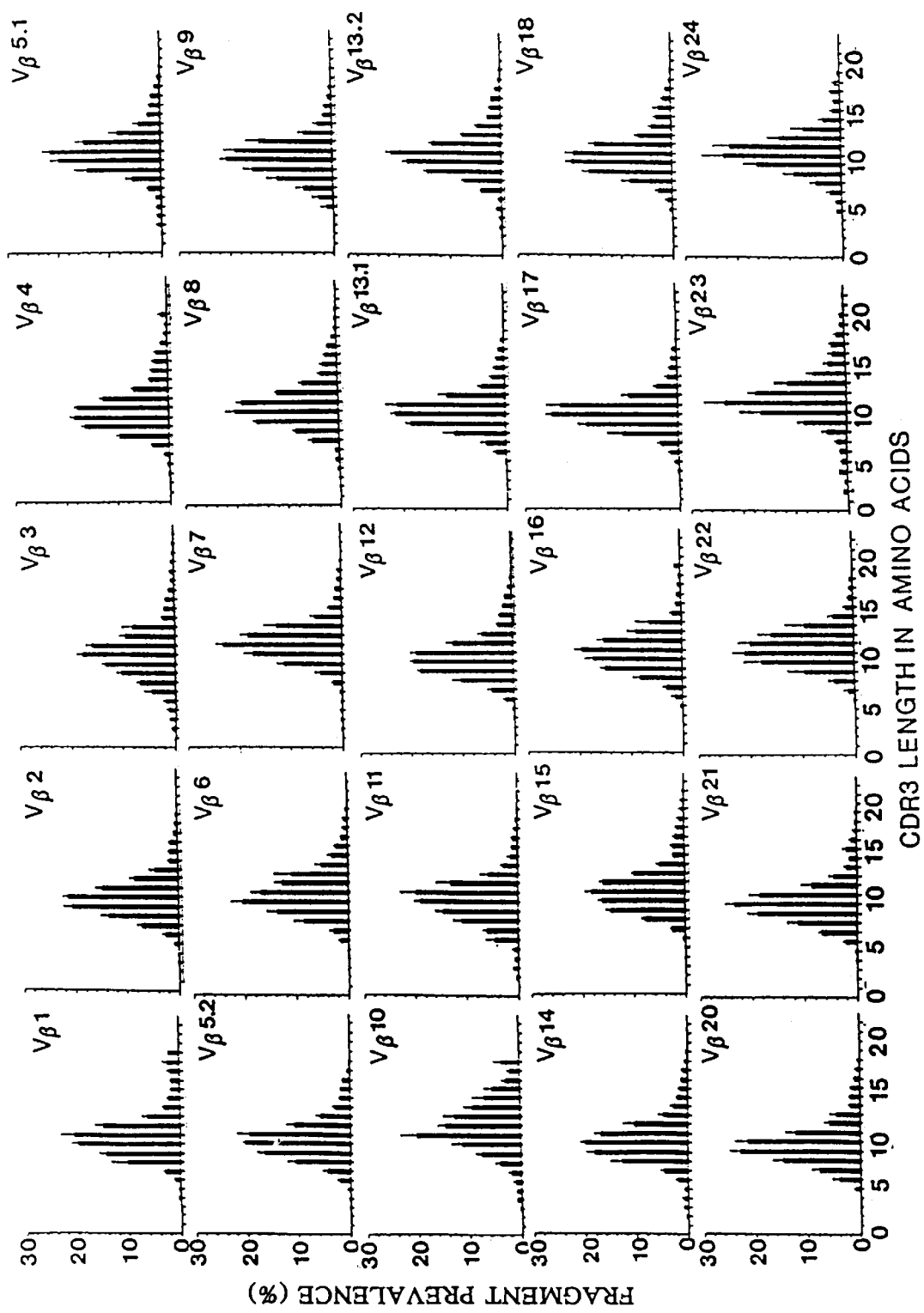
FIG. 3A depicts frequency distribution histograms of deduced CDR3 lengths for twenty-five Vβ families and subfamilies. Each histogram depicts an averaged frequency distribution of the CDR3 lengths in one Vβ gene family, derived by averaging the intrafamily gene fragment profiles obtained from eight healthy blood donors. The prevalence of each fragment in each donor's intrafamily gene fragment profile was calculated by dividing the fluorescence peak area for the fragment by the total peak area observed for the profile. CDR3 lengths (in amino acids) for each Vβ gene family were deduced from fragment lengths (in base pairs) measured from polyacrylamide gels. Standard error (SE) in the CDR3 fragment length prevalences are depicted with error bars in each histogram.

The striking similarity of intrafamily gene fragment length profiles for each Vβ gene family in all of the healthy individuals permitted the construction of an averaged T cell receptor CDR3 intrafamily gene fragment length profile for each Vβ gene family/subfamily. FIGS. 3A (histograms) and 3B (table) depict the gaussian-like frequency distribution of deduced CDR3 lengths (in amino acids) from each of twenty-five Vβ families.

Figure 4:
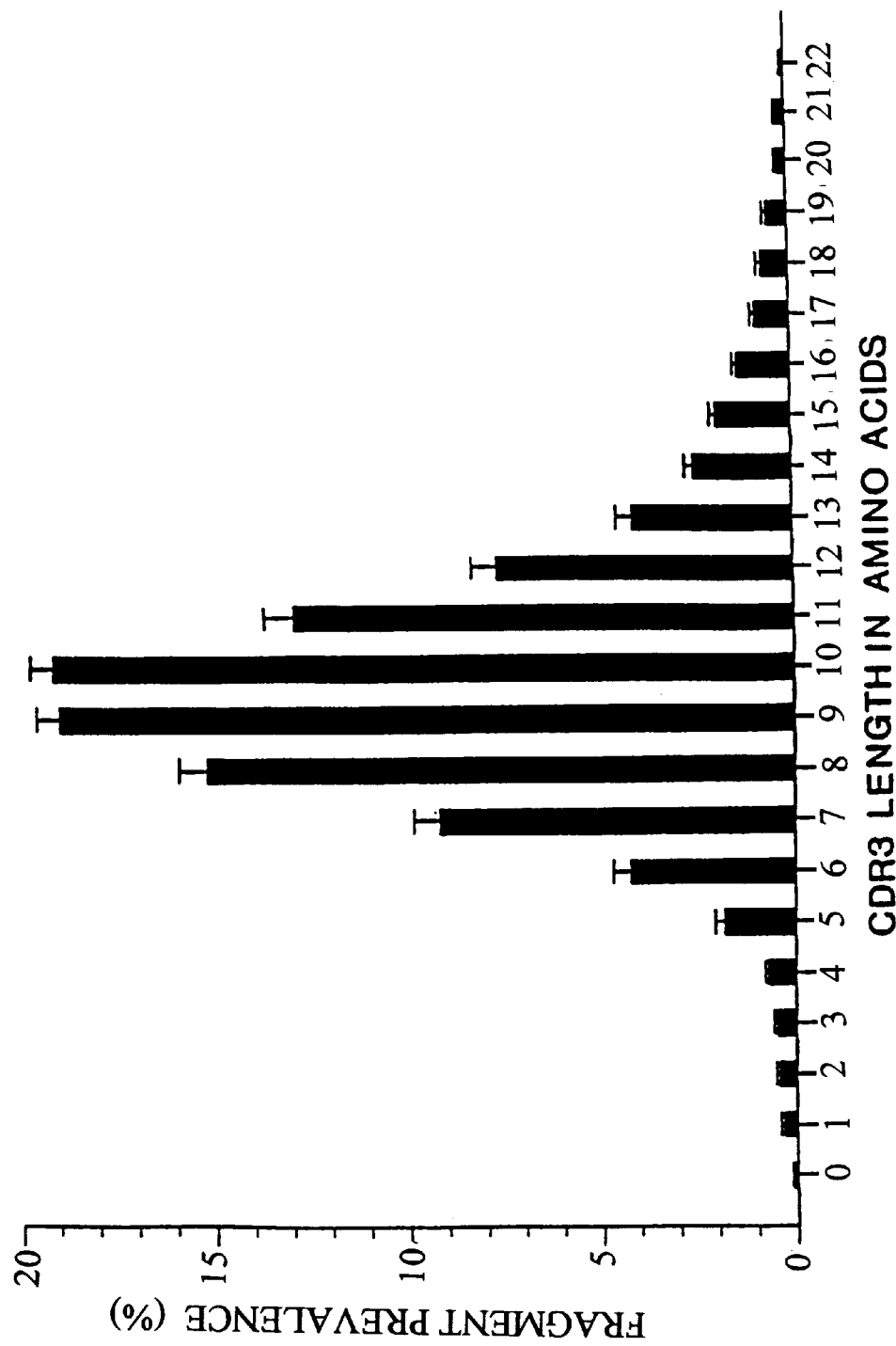
FIG. 4 is a frequency distribution histogram of CDR3 lengths (thick bars) and standard error (thin fines) derived from all Vβ family specific data depicted in FIGS. 3A and 3B and summarized in the bottom rows of FIG. 3B. The mean of the average percentage for each fragment length for all 25 Vβ families and subfamilies from all 8 donors is shown.

Analysis of the data from these eight patients for all 25 families reveals that the measured distance between contiguous nucleotide peaks was 2.96±0.04 nucleotides, in excellent agreement with the predicted distance of 3 nucleotides (i.e., one codon). The lengths of 2,794 measured fragments fell within 0.72±0.16 nucleotides of their calculated lengths based on the PCR primer binding sites. The mean number of CDR3 lengths identified per family was 13.97±1.50, and skew to the right was evident (Table III). In addition, Vβ families 15–18 showed a sharp drop-off in fragment lengths of less than seven amino acids. For all families, the median CDR3 length was 9.52 a.a., and the mean length was 9.71±0.58 a.a. as illustrated in FIG. 4. The most abundant lengths were contained in the range of 7–12 a.a., which cumulatively comprise 83.2% of the total peak area.

Figure 5:
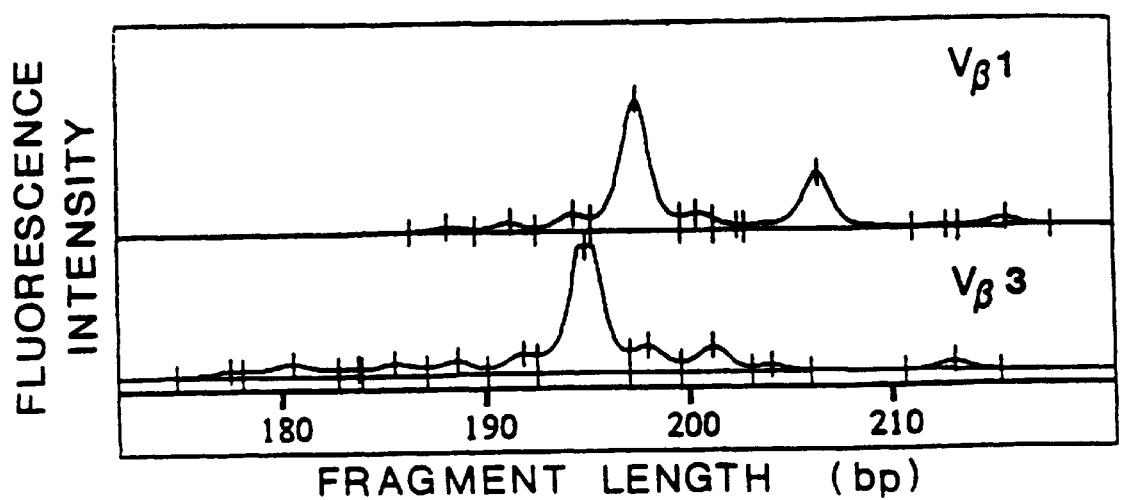
FIG. 5 depicts the unusual intrafamily gene fragment length profiles for the Vβ1 and Vβ3 gene families derived from a ninth donor. The profiles were derived as in FIG. 1 from polyacrylamide gel electrophoresis of 1 μl of 30 cycle family-specific PCR Vβ expansions.

Intrafamily gene fragment length profiles generated from a ninth apparently healthy donor deviated markedly from the gaussian-like pattern found in the other eight donors. Consequently, it was determined that the data from this ninth donor should be excluded from the averaged intrafamily gene fragment length profiles derived for healthy human subjects from the data from the other eight individuals. FIG. 5 depicts this ninth donor's Vβ1 and Vβ3 profiles, which are clearly non-gaussian distributions. Two predominant fragments were detected from Vβ1 with a CDR3 length of 9 and 12 a.a., comprising respectively 45 and 20% of the total peak area. One predominant fragment, corresponding to a CDR3 eight amino acids in length, comprised 80% of the total Vβ3 peak area. The several atypical, non-gaussian profiles with limited heterogeneity from this ninth donor were similar to those described in disease states (Delfau et al., Eur. J. Immunol., 22: 2437 (1992); Farace et al., J. Immunol., 153: 4281 (1994); Gorski et al., (1994), supra; Puisieux et al., (1994), supra) or after immunization (Cochet et al., (1992), supra; Hingorani et al., (1993), supra; Cottrez et al., (1994), supra).

Figure 6A:
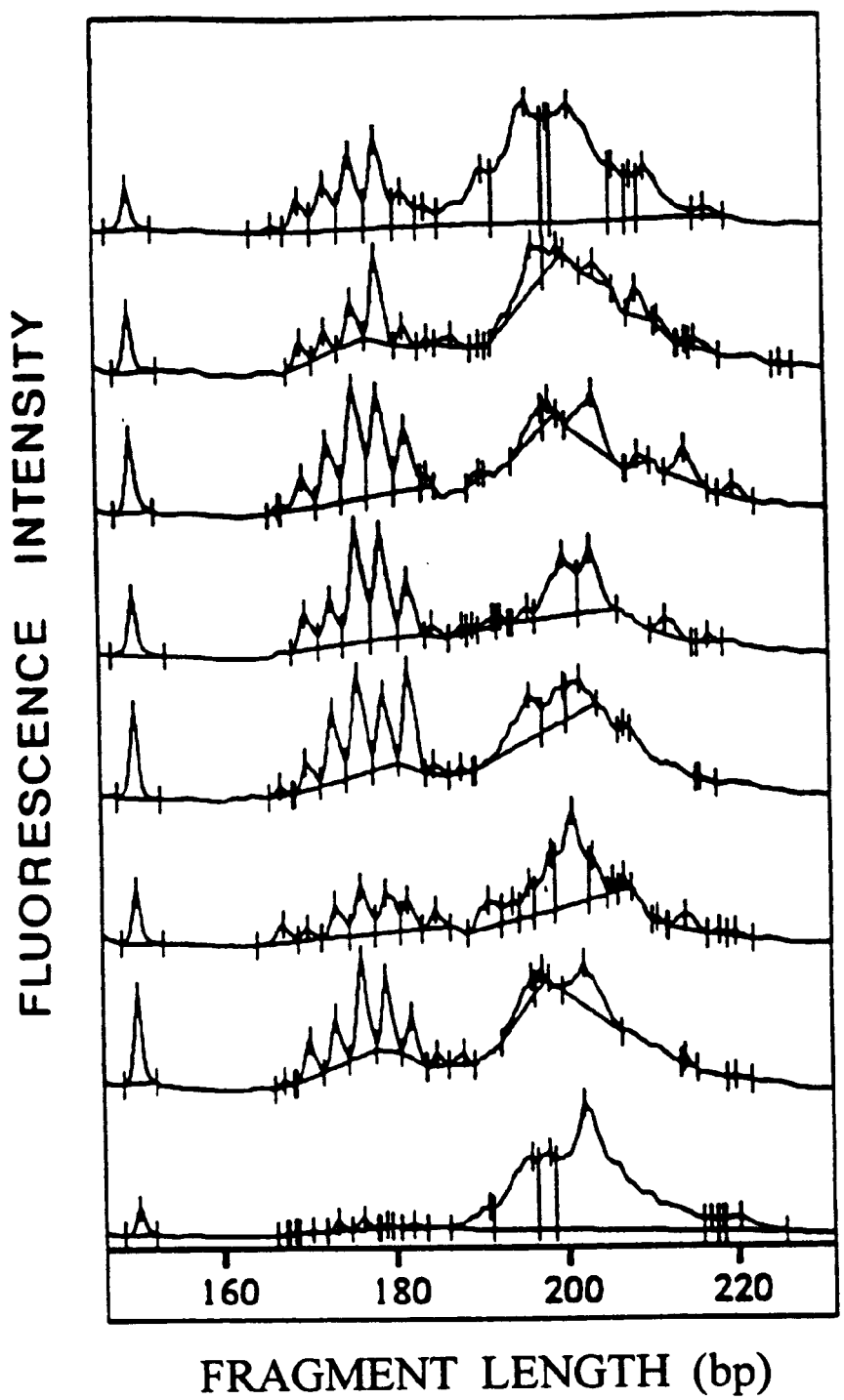
FIGS. 6A and 6B depict the intrafamily gene fragment length profiles for the Vβ19 gene family as in FIG. 2, derived from the blood of eight healthy donors, using the 5' PCR primers Vβ19a and Vβ19b, respectively. A peak corresponding to a 150 base pair size standard is visible in each profile.
Figure 6B:
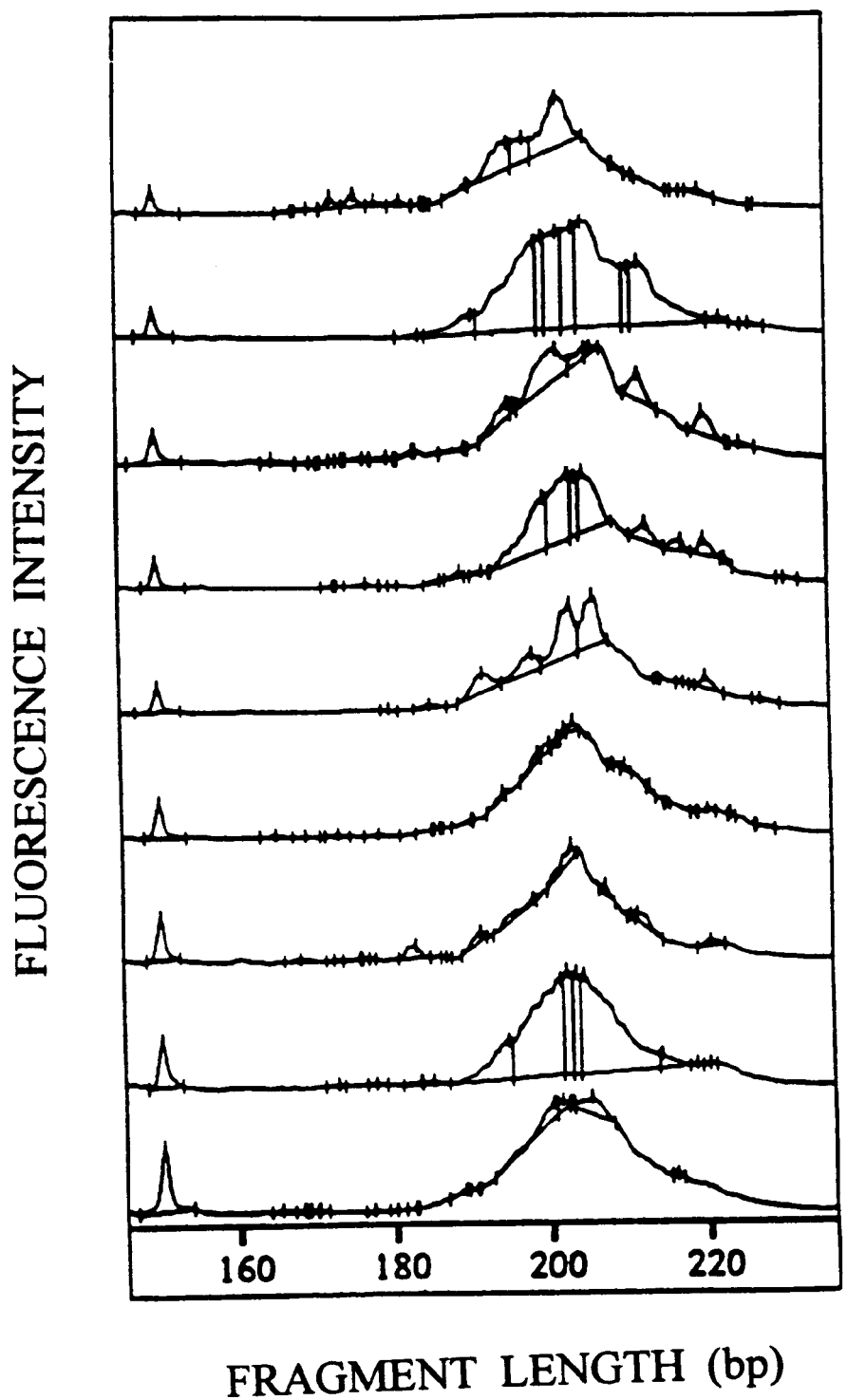

As shown in FIGS. 6A and 6B, the intrafamily Vβ19 gene fragment length profiles derived from the eight healthy donors showed similarity to each other but were characteristically different from the gaussian-like profiles obtained for all of the other Vβ gene families analyzed. The profiles in FIG. 6A and 6B were obtained using two different Vβ19 primers (Vβ19a and Vβ19b, respectively) which differ by (i) an additional 5' CT sequence in Vβ9b, and (ii) an additional 3' CCTGC sequence in Vβ19a (See Table I). The fragments shown in FIG. 6A, amplified by Vβ19a, appeared shifted to the left and right in a bimodal distribution. On the left side of FIG. 6A a gaussian-like profile with three-nucleotide spacing is observed. On the right side the fragment peaks are poorly resolved and do not show three-nucleotide spacing, similar to the pattern found with the Vβ19b primer (FIG. 6B). Based upon the PCR primer binding sites of the two Vβ19 primers and on the mean CDR3 length of 9.71 a.a. (determined from the other Vβ intrafamily gene fragment length profiles), the predicted mean fragment length generated by Vβ19a is 197 base pairs, and by Vβ9b is 199 base pairs. In both cases, this predicted mean fragment length falls within the poorly resolved peaks that do not exhibit three-nucleotide spacing. It is believed that the poor resolution of the Vβ19 profiles is attributable to the particular Vβ19 PCR primers employed. The selection of alternative primers, using known PCR primer-selection techniques (to maximize specificity, minimize intramolecular structures, optimize GC content, etc.), is expected to result in gaussian-like profiles similar to those observed for the other Vβ gene families.

Figure 7:
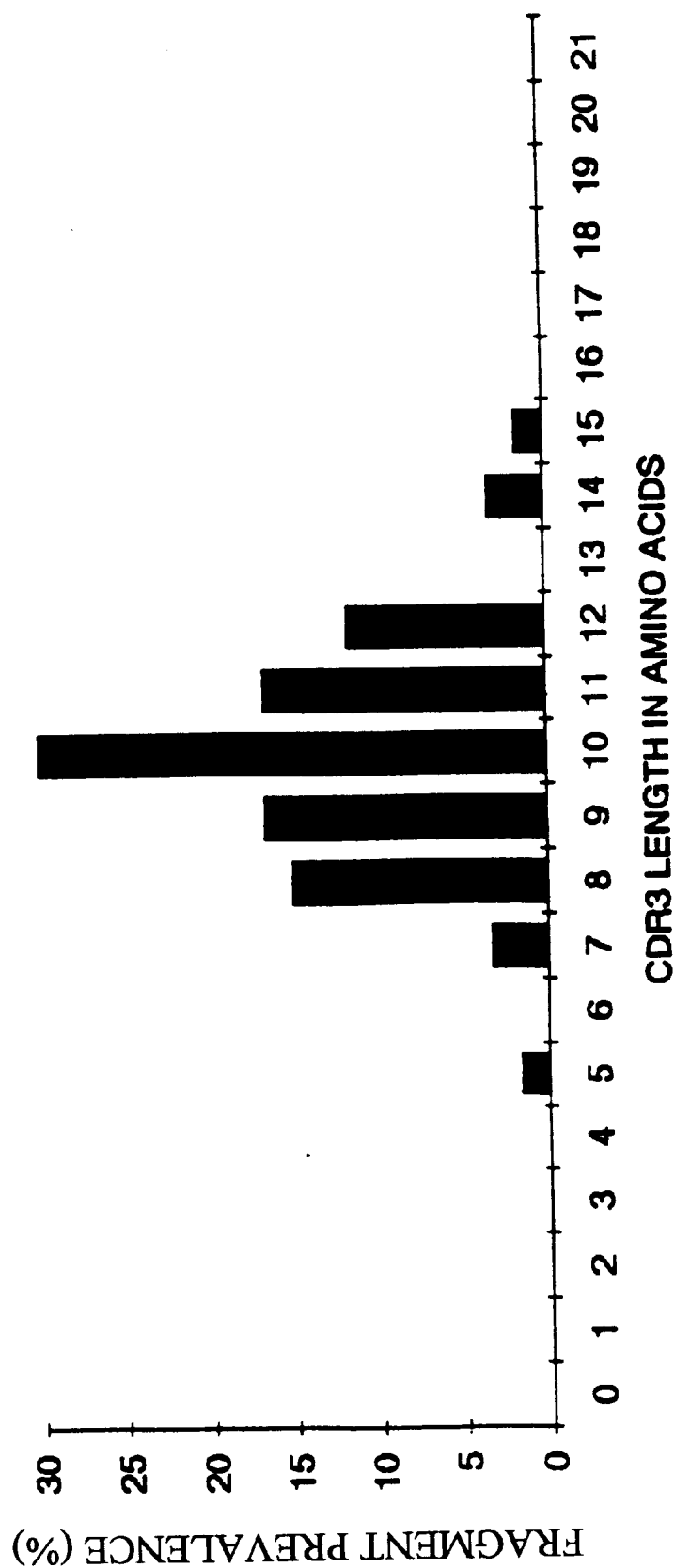
FIG. 7 depicts the frequency distribution of Vβ CDR3 lengths as measured by direct sequencing of 60 T cell clones. The CDR3 length frequencies were obtained by dividing the number of clones of each CDR3 length by the total 60 clones.

As an independent assessment of the accuracy of the intrafamily gene fragment analysis method of measuring CDR3 length prevalences, the TCR β-chain genes were sequenced from 60 T cell clones expressing Vβ families 2, 3, 5.1, 7, or 15. Each clone's CDR3 length was determined from the β-chain nucleotide sequence. The CDR3 length frequency distribution for all 60 clones is shown in FIG. 7. The mean length was 9.97±1.77 a.a. (5–15 a.a.), and lengths of 7–12 a.a. comprised 94.0% of the total. Other investigators (Rosenberg et al., *Eur. J. Immunol.*, 22: 541 (1992); Jores and Meo, *J. Immunol.*, 151: 6110 (1993); Rock et al., (1994), supra) have shown a similar mean length by sequencing. Fragment analysis of PCR expanded cDNA from 2 clones gave values within <1 base pair of their known lengths of 195 and 259 base pairs obtained by sequencing.

In order to identify fragments lengths which might have gone completely undetected due to low abundance in the overall fragment length profile, additional analysis was conducted using deliberately overloaded polyacrylamide gels. In particular, family-specific PCR reactions were performed as described above and run for 35–40 cycles of PCR to yield 3 to 4 times the optimal amount of DNA per 3–5 μl aliquot. When this quantity of DNA was electrophoresed as described above, the peaks in the central area of each profile (corresponding to the most prevalent peaks) could not be resolved individually. However, a mean of 2.7±1.8 additional peaks per family were detected in the low abundance areas (i.e., peaks corresponding to large and small CDR3 lengths), yielding a mean total of 17.2±1.9 CDR3 lengths per family. The mean lengths for the shortest and longest CDR3 regions for all families were 3.0±1.6 and 19.1±0.8 a.a. No peaks were detected corresponding to CDR3 lengths greater than 22 amino acids or less than −1 amino acid. Extreme CDR3 lengths (e.g., −1 amino acid or 22 amino acids) were observed only in few Vβ families, but lengths of 6 through 16 amino acids were observed in the intrafamily gene fragment length profiles of all 8 individuals within all Vβ families. Although the observance of a CDR3 length of −1 amino acid was unexpected, it appeared in the Vβ11 family of all 8 donors, and once elsewhere.

The effect of the number of PCR cycles on the threshold of detection and relative abundance of Vβ families is illustrated in Table IV for a high abundance family (Vβ2) and a low abundance family (Vβ10). For the Vβ2 family, the relative abundance of fragment peaks did not vary significantly with differences in the number of PCR cycles from 20–40 cycles, except for the prevalence of low abundance fragments (5, 11, and 12 a.a.) in the 20 cycle PCR expansion, which could not be seen on gels loaded with 1 or 3 μl of sample and therefore had to be extrapolated from gels loaded with 10 μl samples.

TABLE IV

Relative abundance of CDR3 lengths after varying numbers of PCR cycles

| Vβ Family | CDR3 Length in amino acids | Number of PCR Cycles | | | | |
|---|---|---|---|---|---|---|
| | | 20 | 25 | 30 | 35 | 40 |
| Vβ2 | 5 | 4.76* | 3.52 | 3.68 | 3.43 | 3.52 |
| | 6 | 11.29 | 9.54 | 9.08 | 9.27 | 9.04 |
| | 7 | 20.56 | 18.49 | 18.20 | 18.84 | 18.51 |
| | 8 | 25.18 | 24.79 | 24.28 | 24.93 | 25.03 |
| | 9 | 22.01 | 21.79 | 21.92 | 21.94 | 22.14 |
| | 10 | 10.79 | 12.00 | 12.55 | 12.43 | 12.42 |
| | 11 | 3.96 | 6.73 | 6.84 | 5.74 | 6.50 |
| | 12 | 1.45 | 3.13 | 3.45 | 3.42 | 2.84 |
| Vβ10 | 6 | | 3.66 | 2.62 | 4.03 | 4.05 |
| | 7 | | 9.90 | 9.07 | 9.83 | 10.08 |
| | 8 | | 13.14 | 13.85 | 14.29 | 14.67 |
| | 9 | | 19.17 | 19.59 | 19.57 | 19.33 |
| | 10 | | 25.72 | 24.56 | 23.29 | 22.92 |
| | 11 | | 14.37 | 16.58 | 14.46 | 16.39 |
| | 12 | | 8.37 | 9.04 | 8.98 | 7.00 |
| | 13 | | 5.66 | 4.69 | 5.56 | 5.55 |

*Percent of total fragments amplified

The superiority of a 25–40 cycle expansion compared to a 20 cycle PCR expansion was evident from the data obtained for the low-abundance Vβ10 family. After 20 cycles, ill defined, very low amplitude peaks could just be visualized for the most abundant CDR3 lengths only. For cycles 25–40 there was no significant change in abundance for fragments 7–12 a.a., although there was variability without systematic bias for the lowest abundance fragments (6 and 13 a.a.). This comparison demonstrates that performing PCR for every family to saturation phase or near saturation is preferred, to reduce or eliminate variations. The comparison further illustrates that, especially for low abundance fragments, it is preferable to use control groups with standard deviation as a measure of variance for the purposes of identifying expanded assay fragments, as described in Example 7 and elsewhere herein. The quantity of DNA polymerase employed in the PCR reactions is considered important to minimize non-specific products, and preferably is in the range of 0.5–1.0 units per 10 μl PCR reaction, and more preferably is limited to 0.5 U/reaction.

EXAMPLE 2

Demonstration of the Superiority of Random Primers for Generating cDNA PCR Template for Intrafamily Gene Fragment Analysis In the course of developing the intrafamily gene fragment analysis procedures described in Example 1, the following experiment was conducted to determine an optimum cDNA synthesis procedure, the cDNA being used as template for family-specific PCR expansion of Vβ regions. In the experiment, three types of primers (random hexamers, oligo-dT, and specific Cβ) were used for cDNA synthesis from a total RNA sample extracted from PBMC as described in Example 1. The cDNA was then amplified via PCR using a Vβ2 and nested Cβ primer pair. The PCR products were analyzed on a 2% agarose gel to determine the relative amount of Vβ2 PCR product amplified from each cDNA preparation.

The cDNA synthesis reactions were performed using GIBCO BRL's SuperScript first strand cDNA kit. A 57 μl reaction cocktail was prepared containing 6.0 μl 10× buffer (200 mM Tris-HCl, pH 8.4; 500 mM KCl, 25 mM MgCl$_2$, 1 mg/ml BSA), 3.0 μl of 10 mM dNTPs, 6.0 μl of 0.1 M DTT, 3.0 μl SuperScript reverse transcriptase (200 U/μl), and 3.0 μg total RNA in 39 μl DEPC H$_2$O. The cocktail was divided into three tubes, each containing 1.0 μl of different primer at the concentrations: 50 ng random primer, 500 ng oligo-dT primer, and 200 ng Cβ-specific primer. The three reactions were incubated at 37° C. for one hour. The concentrations of random and oligo-dT primers were selected according to the manufacturer's recommendation.

A plurality of PCR reactions were conducted using cDNA from each cDNA reaction as template. More particularly, 20 μl PCR reactions were set up containing 1.0 μl cDNA, 2.0 μl 10× buffer, 0.3 μl 10 mM dNTPs, 0.2 μl Taq DNA polymerase (5 U/μl), 2.0 μl of 3.0 μM Vβ2 primer (Table I), 2.0 μl of 3.0 μM nested Cβ primer (Table I), and 11.5 μl water. The reactions were heated at 94° C. for 4 minutes, subjected to 30 cycles of PCR (denaturation at 94° C. for 45 seconds, annealing at 55° C. for 45 seconds, and extension at 70° C. for 45 seconds), and extended a final 10 minutes at 70° C. Thereafter, 5.0 μl was removed from each reaction for analysis and the remainder was subjected to 15 additional cycles of PCR. A second 5.0 μl aliquot was removed from each reaction and the remainder was subjected to 5 additional cycles of PCR.

Each 5.0 μl PCR product was electrophoresed on a 2% agarose gel, and the gel was stained with ethidium bromide and observed under UV light. After 30 cycles of PCR, the random primer cDNA showed a clear band of DNA of about 200 nucleotides, the oligo-dT showed a faint band of the same size, and the Cβ cDNA showed nothing. After 45 cycles, the random primer cDNA showed a sharp, high density band, the oligo-dT cDNA showed a clear band, and the Cβ cDNA showed a very weak band. After 50 cycles, all three cDNAs showed a strong band but the band corresponding to the Cβ primer was smeared in appearance.

From the foregoing experiment, it was concluded that cDNAs made from random primers yielded the most abundant Vβ gene-specific PCR products with few non-specific products produced (even at excessive cycles). Therefore, random-primed cDNA is preferred for use as PCR template in the intrafamily gene fragment analysis procedures described herein.

EXAMPLE 3

Improved T Cell Receptor Intrafamily Vβ Gene Fragment Analysis

The intrafamily Vβ gene fragment analysis procedure described in Example 1 is further improved to enhance efficiency, rapidity, and repeatability. The data reported in Example 1 demonstrates the importance of conducting cDNA and PCR reactions such that all CDR3 fragments within a given family have a maximum opportunity to be amplified, without conducting excessive PCR (which can generate non-specific products). The ideal PCR reaction (a reaction cycled until saturation stage) is different for different Vβ gene families because more abundant families (and/or families wherein a more efficient Vβ forward PCR primer has been employed) reach saturation stage in fewer cycles than less abundant families. Also illustrated in Example 1 is the importance of loading an optimum quantity of PCR reaction product on a gel: loading too little PCR product results in the inability to detect low-abundance CDR3 fragment lengths, whereas loading too much results in the overloading of high-abundance CDR3 fragment lengths and the inability to resolve the high-abundance peaks individually. The following procedures permit intrafamily Vβ gene fragment analysis for twenty-five Vβ families in a manner wherein only a single set of twenty-five PCR reactions (plus controls) is conducted and wherein intrafamily gene fragment length profiles for all twenty-five families are determined from analysis of a single polyacrylamide gel (wherein a sample from each of the PCR reactions has been electrophoresed).

cDNA Synthesis and PCR Expansion

A single, 33 μl cDNA synthesis reaction is conducted essentially as described in Example 1 using 1.0 μg total RNA and Pharmacia's cDNA kit. Family-specific and control PCR reactions are set up and performed as described in Example 1, except thirty-five PCR cycles are performed with 45 seconds of denaturation at 94° C., 45 seconds of annealing at 55° C., and 45 seconds of primer extension at 70° C. A final 10 minute, 70° C. extension is performed after the last PCR cycle.

Polyacrylamide Gel Sample Loading

It was experimentally determined that the amount of family-specific PCR product loaded on the gel for any given family should be such that low-abundance peaks are detected at a minimum level of 50 peak area units while high-abundance peaks are detected at a maximum of about 8000 units (using Pharmacia's A.L.F sequencer and Fragment Manager™ 1.1 software). If a high-abundance fragment is present at greater concentrations than about 8000–8500 absorbance units, then it becomes difficult to resolve that fragment peak from neighboring fragment peaks during polyacrylamide gel electrophoresis analysis. Procedures were developed to achieve these parameters rapidly for each independent set of intrafamily gene fragment analyses conducted.

First, the averaged intrafamily gene fragment length profiles derived from healthy individuals and described in Example 1 (FIGS. 3A and 3B) were used to determine a theoretical maximum total peak area that would be preferred for each family, consistent with the limitation of having a maximum 8000 peak units of area for the most prevalent fragment in that family. For example, if the most prevalent fragment length in a particular profile has an average prevalence of 25% (i.e., comprises 25% of the entire fluorescence peak area measured for the family), then a theoretical preferred maximum total peak area for the family is 32,000 peak area units (i.e., 8000/0.25=32,000).

Proper sample volumes for all Vβ family-specific PCR reactions are determined by performing an initial polyacrylamide gel analysis of each family-specific PCR reaction. For example, the initial analysis is conducted by electrophoresing an aliquot from the Cβ control PCR reaction and an aliquot from each Vβ family-specific PCR reaction of a healthy individual on a polyacrylamide gel and analyzing peak areas as described in Example 1. From the peak area measurements, a calculation is made to determine the proper subsequent aliquot from each Vβ family-specific PCR reaction required to produce a profile having the theoretical preferred maximum total peak area for that family. For example, if a 1 μl aliquot from the Vβ1 PCR reaction produced 8000 units of total Vβ1 peak area (after summing all of the peaks in the Vβ1 profile), then about 4.1 μl would constitute an aliquot to produce a profile having the theoretical preferred maximum total peak area of 32,747.

A second polyacrylamide gel electrophoresis then is performed to generate intrafamily gene fragment length profiles for all 25 Vβ families. A sample from each Vβ family-specific PCR reaction is loaded on the second gel, each sample size being selected such that (1) the total family peak area will be about 50–75% of the theoretical preferred maximum total peak area for that family; and (2) the total family peak area will be at least about 15,000 units, so that low-abundance peaks are observed. The sample volume is limited to 50–75% of the theoretical preferred maximum to insure against overloading the most abundant peaks.

This systematic procedure for determining the proper sample size for gel loading will result in intrafamily Vβ gene fragment length profiles wherein both high- and low-abundance fragment peaks are detected in each Vβ profile without concomitant overloading of high-abundance fragments. Thus, using twenty-five lanes on a single polyacrylamide gel, intrafamily Vβ gene fragment length profiles are determined rapidly for all twenty-five Vβ families characterized in FIG. 3A.

Alternatively, acceptable Vβ family-specific sample volumes are determined more rapidly by analyzing only one of the 25 families on the initial polyacrylamide gel. For example, an initial analysis is conducted by electrophoresing three different aliquots from the Vβ1 family-specific PCR reaction on a polyacrylamide gel and analyzing peak areas as described in Example 1. From the peak area measurements of each lane, a calculation is made to determine the proper subsequent aliquot from the Vβ1 reaction required to produce a profile having 50–75% of the theoretical preferred maximum total peak area for that family. For example, if a 4.1 μl of the Vβ1 PCR reaction will produce a profile having the theoretical preferred maximum total peak area for Vβ1, then an aliquot of about 2–3.1 μl is selected as a proper subsequent aliquot for generating a Vβ1 intrafamily gene fragment length profile.

Acceptable aliquots for the remaining families are estimated using ratios provided in Table V. Table V presents the average prevalence of the largest peak in each Vβ intrafamily gene fragment length profile, the standard deviation observed for this prevalence, and the theoretical preferred maximum total peak area for each family. Table V also provides two ratios (right columns) for calculating acceptable sample volumes for the remaining families. Ratio A reflects the theoretical preferred maximum peak areas of each family, relative the theoretical preferred maximum peak area of Vβ1. Ratio B reflects the total peak area observed in the indicated intrafamily gene fragment length profile derived from the blood of a single healthy individual relative to the total peak area observed in that individual's Vβ1 profile, where an equal volume of PCR reaction product (e.g., 1.5 μl) was analyzed from each family-specific PCR reaction. For example, the calculated Vβ16 family maximum peak area is about 105% of that of Vβ1 (ratio A of 1.05); the Vβ16 gene family was observed to have about 90% of the total peak area of the Vβ1 gene family for the selected healthy individual (Ratio B of 0.90).

TABLE V

POLYACRYLAMIDE GEL LOADING RATIOS FOR Vβ FAMILIES

| Vβ Family | Average largest peak | SD largest peak | Max. Total peak area for family | Ratio A (to Vβ1) | Ratio B (to Bβ1) |
|---|---|---|---|---|---|
| 1 | 24.43% | 5.40% | 32747 | 1.00 | 1.00 |
| 2 | 22.65% | 3.51% | 35320 | 1.08 | 1.12 |
| 3 | 20.24% | 2.99% | 39526 | 1.21 | 1.21 |

TABLE V-continued

POLYACRYLAMIDE GEL LOADING RATIOS FOR Vβ FAMILIES

| Vβ Family | Average largest peak | SD largest peak | Max. Total peak area for family | Ratio A (to Vβ1) | Ratio B (to Bβ1) |
|---|---|---|---|---|---|
| 4 | 18.55% | 2.40% | 43127 | 1.32 | 1.67 |
| 5.1 | 23.60% | 3.90% | 33898 | 1.04 | 1.04 |
| 5.2 | 22.61% | 3.25% | 35383 | 1.08 | 1.32 |
| 6 | 24.39% | 5.34% | 32800 | 1.00 | 1.03 |
| 7 | 23.62% | 3.60% | 33870 | 1.03 | 1.00 |
| 8 | 20.35% | 4.60% | 39312 | 1.20 | 1.51 |
| 9 | 22.43% | 3.46% | 35667 | 1.09 | 1.09 |
| 10 | 33.34% | 16.36% | 23995 | 0.73 | 0.57 |
| 11 | 25.31% | 6.33% | 31608 | 0.97 | 1.12 |
| 12 | 20.32% | 1.46% | 39370 | 1.20 | 1.72 |
| 13.1 | 23.26% | 1.72% | 34394 | 1.05 | 1.22 |
| 13.2 | 20.48% | 3.56% | 39063 | 1.19 | 1.37 |
| 14 | 20.91% | 2.70% | 38259 | 1.17 | 1.18 |
| 15 | 19.05% | 2.82% | 41995 | 1.28 | 1.53 |
| 16 | 23.29% | 4.31% | 34350 | 1.05 | 0.90 |
| 17 | 26.67% | 4.21% | 29996 | 0.92 | 1.06 |
| 18 | 21.70% | 2.95% | 36866 | 1.13 | 0.99 |
| 20 | 25.76% | 5.84% | 31056 | 0.95 | 1.02 |
| 21 | 25.27% | 4.16% | 31658 | 0.97 | 0.88 |
| 22 | 32.30% | 8.33% | 24768 | 0.76 | 0.48 |
| 23 | 29.95% | 12.87% | 26711 | 0.82 | 1.04 |
| 24 | 33.86% | 9.19% | 23627 | 0.72 | 0.54 |

An acceptable aliquot for the other Vβ family-specific PCR reactions is calculated from the aliquot selected for the Vβ1 reaction and from the peak area ratios A and B of Table V, according to the following formula:

$$Volume_{V\beta N} = Volume_{V\beta 1} \times (Ratio\ A_{V\beta N}/Ratio\ B_{V\beta N})$$

For example, if 2.5 μl were a proper aliquot from the Vβ1 PCR reaction to load on a gel (to produce 50–75% of the theoretical preferred maximum total peak area), then 2.9 μl (i.e., 2.5×1.05/0.90) would be a proper aliquot for the Vβ16 family.

It is expected that derivation of the ratio B column of Table V by averaging total family peak area ratios determined from multiple healthy individuals will supply suitable ratio B values as well.

EXAMPLE 4

Figure 8A:
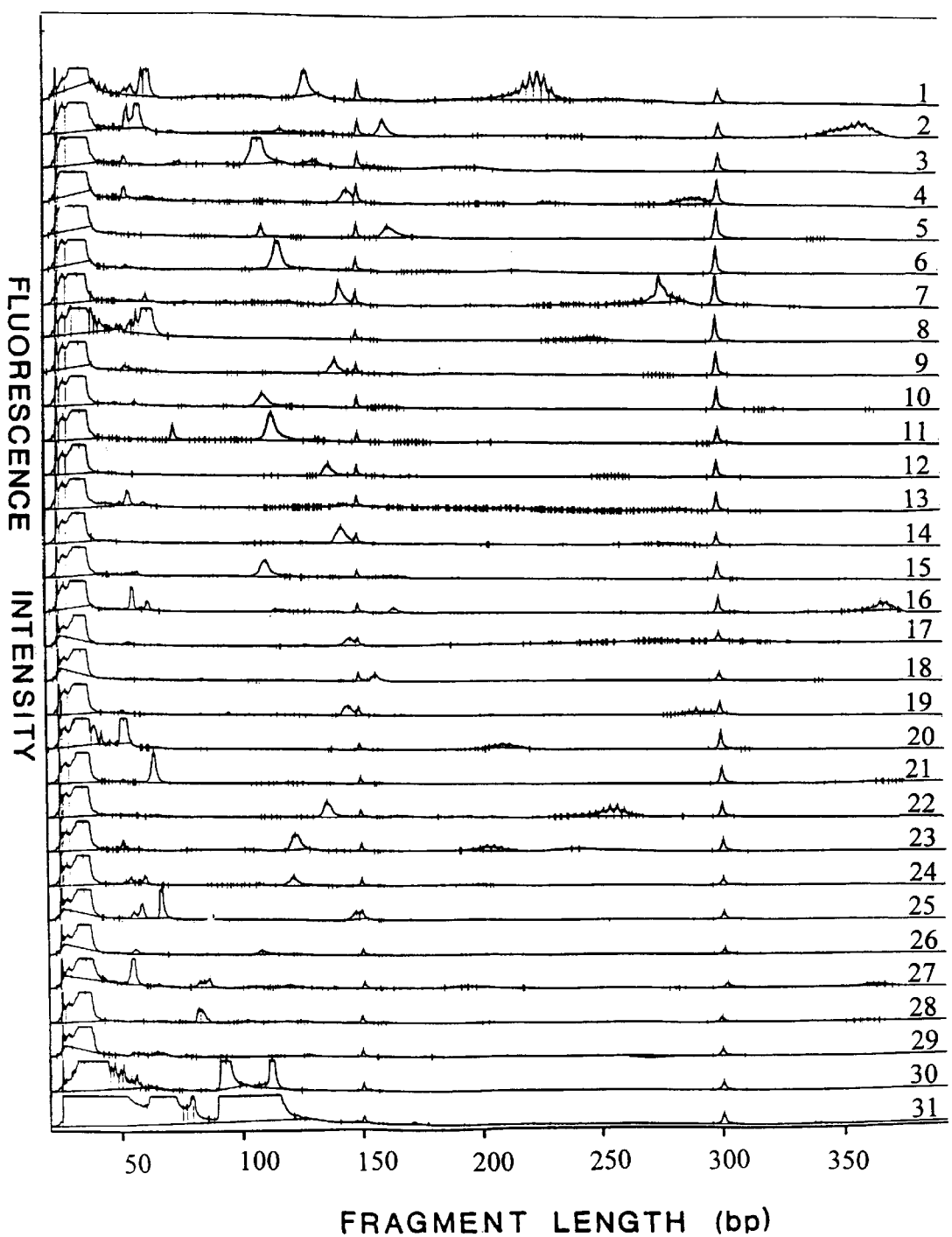
FIG. 8A graphically depicts intrafamily gene fragment length profiles generated and scaled automatically by the Fragment Manager™ 1.1 software used to analyze each profile after electrophoresis on a polyacrylamide gel. Fluorescence intensity is plotted as a function of fragment length (measured in base pairs). The single-PCR procedures described in Example 1 were used to generate the profiles, except that 5' Vα primers and a 3' fluoresceinated-Cα primer were substituted for the Vβ and Cβ primers described in Example 1. Lanes 1–29 depict the intrafamily gene fragment length profiles for gene families Vα1–Vα29, respectively. Lanes 30 and 31 depict the profiles of the PCR reactions wherein a Cβ control primer pair and a β-actin control primer pair were employed. Each lane contains size standards of 150 and 300 nucleotides.

Determination of Normal Human Intrafamily Gene Fragment Profiles for T Cell Receptor Vα Gene Families The procedure described in Example 1 was employed to generate intrafamily gene fragment length profiles for T cell receptor Vα gene families by substituting Vα family-specific 5' oligonucleotide PCR primers and a fluoresceinated-Cα 3' primer for the Vβ and Cβ primers of Example 1. However, in a majority of the intrafamily Vα gene fragment length profiles, an undesirably large number of non-specific PCR products were generated (FIG. 8A). The following variation of the procedure described in Example 1 was conducted to generate improved intrafamily gene fragment length profiles for human T cell receptor Vα gene families.

As described in Example 1, the same purified total RNA from PBMC obtained from blood samples from 8 healthy human subjects was used to synthesize cDNA using random primers. Each cDNA sample was used to provide template for PCR reactions to amplify twenty-nine TCR Vα gene families.

The conditions for a first round of PCR reactions were essentially identical to the PCR conditions described in Example 1, with the following variations. First, twenty-nine family-specific 5' Vα oligonucleotide primers (Table VI) were employed in twenty-nine separate PCR reactions (in place of the Vβ family-specific primers of Example 1). In place of the fluoresceinated 3' Cβ primer, a single, unlabelled Cα primer (Table VI) was employed in each of the twenty-nine reactions. For control PCR reactions, the β-actin primers and Cβ described in Example 1 were employed to amplify a portion of the β-actin locus and a portion of the Cβ locus. Twenty-five cycles of PCR were conducted as described in Example 1, except that the annealing temperature was increased from 55° C. to 60° C. to increase stringency and minimize non-specific PCR reaction products, and the primer extension temperature was increased from 70° C. to 72° C.

TABLE VI

PCR OLIGONUCLEOTIDE PRIMERS FOR TCR-CDR3 INTRAFAMILY Vα GENE FRAGMENT ANALYSIS

| Primer[1] | Primer Sequence (5' to 3')[2] | 5' Binding Position[3] | Distance to Residue 96 (nucleotides) | SEQ. ID NO: |
|---|---|---|---|---|
| A1. Vα1 | GGC ATT AAC GGT TTT GAG GCT GGA | 235 | 108 | 29 |
| A2. Vα2 | CAG TGT TCC AGA GGG AGC CAT TGT | 93* | 244 | 30 |
| A3. Vα3 | CCG GGC AGC AGA CAC TGC TTC TTA | 297 | 40 | 31 |
| A4. Vα4 | TTG GTA TCG ACA GCT TCA CTC CCA | 153 | 172 | 32 |
| A5. Vα5 | CGG CCA CCC TGA CCT GCA ACT ATA | 113 | 227 | 33 |
| A6. Vα6 | TCC GCC AAC CTT GTC ATC TCC GCT | 287 | 66 | 34 |
| A7. Vα7 | GCA ACA TGC TGG CGG AGC ACC CAC | 159 | 166 | 35 |
| A8. Vα8 | CAT TCG TTC AAA TGT GGG CAA AAG | 204 | 133 | 36 |
| A9. Vα9 | CCA GTA CTC CAG ACA ACG CCT GCA | 168 | 160 | 37 |
| A10. Vα10 | CAC TGC GGC CCA GCC TGG TGA TAC | 282 | 45 | 38 |
| A11. Vα11 | CGC TGC TCA TCC TCC AGG TGC GGG | 254* | 55 | 39 |
| A12. Vα12 | TCG TCG GAA CTC TTT TGA TGA GCA | 213 | 139 | 40 |
| A13. Vα13 | TTC ATC AAA ACC CTT GGG GAC AGC | 152* | 167 | 41 |
| A14. Vα14 | CCC AGC AGG CAG ATG ATT CTC GTT | 181 | 165 | 42 |
| A15. Vα15 | TTG CAG ACA CCG AGA CTG GGG ACT | 278 | 50 | 43 |
| A16. Vα16 | TCA ACG TTG CTG AAG GGA ATC CTC | 89 | 251 | 44 |
| A17. Vα17 | TGG GAA AGG CCG TGC ATT ATT GAT | 204 | 160 | 45 |
| A18. Vα18 | CAG CAC CAA TTT CAC CTG CAG CTT | 114 | 229 | 46 |
| A19. Vα19 | ACA CTG GCT GCA ACA GCA TCC AGG | 162 | 175 | 47 |
| A20. Vα20 | TCC CTG TTT ATC CCT GCC GAC AGA | 232 | 93 | 48 |
| A21. Vα21 | AGC AAA ATT CAC CAT CCC TGA GCG | 92 | 266 | 49 |
| A22. Vα22 | CCT GAA AGC CAC GAA GGC TGA TGA | 197 | 139 | 50 |
| A23. Vα23 | TGC CTC GCT GGA TAA ATC ATC AGG | 246 | 91 | 51 |
| A24. Vα24 | CTG GAT GCA GAC ACA AAG CAG AGC | 259 | 84 | 52 |
| A25. Vα25 | TGG CTA CGG TAC AAG CCG GAC CCT | 148 | 183 | 53 |
| A26. Vα26 | AGC GCA GCC ATG CAG GCA TGT ACC | 299 | 38 | 54 |
| A27. Vα27 | AAG CCC GTC TCA GCA CCC TCC ACA | 268* | 74 | 55 |
| A28. Vα28 | TGG TTG TGC ACG AGC GAG ACA CTG | 95 | 245 | 56 |
| A29. Vα29 | GAA GGG TGG AGA ACA GAT GCG TCG | 210 | 127 | 57 |

TABLE VI-continued

PCR OLIGONUCLEOTIDE PRIMERS FOR TCR-CDR3 INTRAFAMILY Vα GENE FRAGMENT ANALYSIS

| Primer[1] | Primer Sequence (5' to 3')[2] | 5' Binding Position[3] | Distance to Residue 96 (nucleotides) | SEQ. ID NO: |
|---|---|---|---|---|
| A30.Cα | ATA CAC ATC AGA AT<u>T</u> CTT ACT TTG | 129 | | 58 |
| A31.CαF | F-GTC ACT GGA TTT AGA GTC T | 57 | | 59 |

[1]Primers A1, A11, A12, and A17–A21 were described previously in Klein et al., Proc. Natl. Acad. Sci. (USA), 84:6884–6888 (1987). Primers A2, A5, A7 and A22–A29 were described previously in Roman-Roman et al., Eur. J. Immunol., 21:927–933 (1991). Primers A4–A5, A6, and A8–A10 were described previously in Yoshikai et al., J. Exp. Med., 164:90–103 (1986). Primers A13–A16 were described previously in Kimura et al., Eur. J. Immunol., 17:375–383 (1987). Primers A30 and A31 were previously described in Genevée et al. (1992), supra.
[2]Underlined nucleotides are mismatches introduced to reduce cross-hybridization to other Vα subfamilies.
[3]Nucleotides are numbered beginning with the putative translation initiation site, ATG (Genevée, et al. (1992)) except where otherwise noted.
*Numbering starts from the first nucleotide position in the sequence.

A second series of PCR reactions was then conducted to further minimize the amount of non-specific PCR products. The second series of PCR reactions were identical to the first series except for the following important variations. First, 0.1 µl aliquots from the first series of family-specific PCR reactions were used as the template for the corresponding family-specific reaction in the second series of PCR reactions (in place of the 0.85 µl cDNA aliquot). Second, a nested, fluoresceinated 3' Cα primer (Table VI: CαF) was substituted for the unlabelled Cα primer used in the first series of PCR reactions, the fluoresceinated primer selected to bind upstream from the binding site of the unlabelled Cα primer. Third, thirty cycles of PCR were performed in the second series of PCR reactions.

Aliquots of the PCR products generated in the second series of PCR reactions were separated by fragment length using polyacrylamide gel electrophoresis and analyzed using Pharmacia's Fragment Manager™ software as described in Example 1.

CDR3 amino acid measurements were deduced from the fragment length measurements for each intrafamily Vα gene fragment length profile, adapting the formula of Rock et al. (1994). In particular, from each fragment length measurement, the following nucleotide lengths were subtracted: (a) 30 nucleotides, representing the conserved length (3') of the Jα segment through the constant phenylalanine residue (5'); (b) 57 nucleotides, representing the portion of the 5' end of the Cα gene segment amplified as a result of the fluoresceinated Cα PCR primer employed; and (c) the number of nucleotides measured from the 5' end of the particular Vα primer employed to position 96 of the a chain (for each Vα primer employed, the corresponding number of nucleotides is set forth in Table VI). The resultant fragment length was divided by three to provide a CDR3 length determination (in amino acid residues).

Figure 8B:
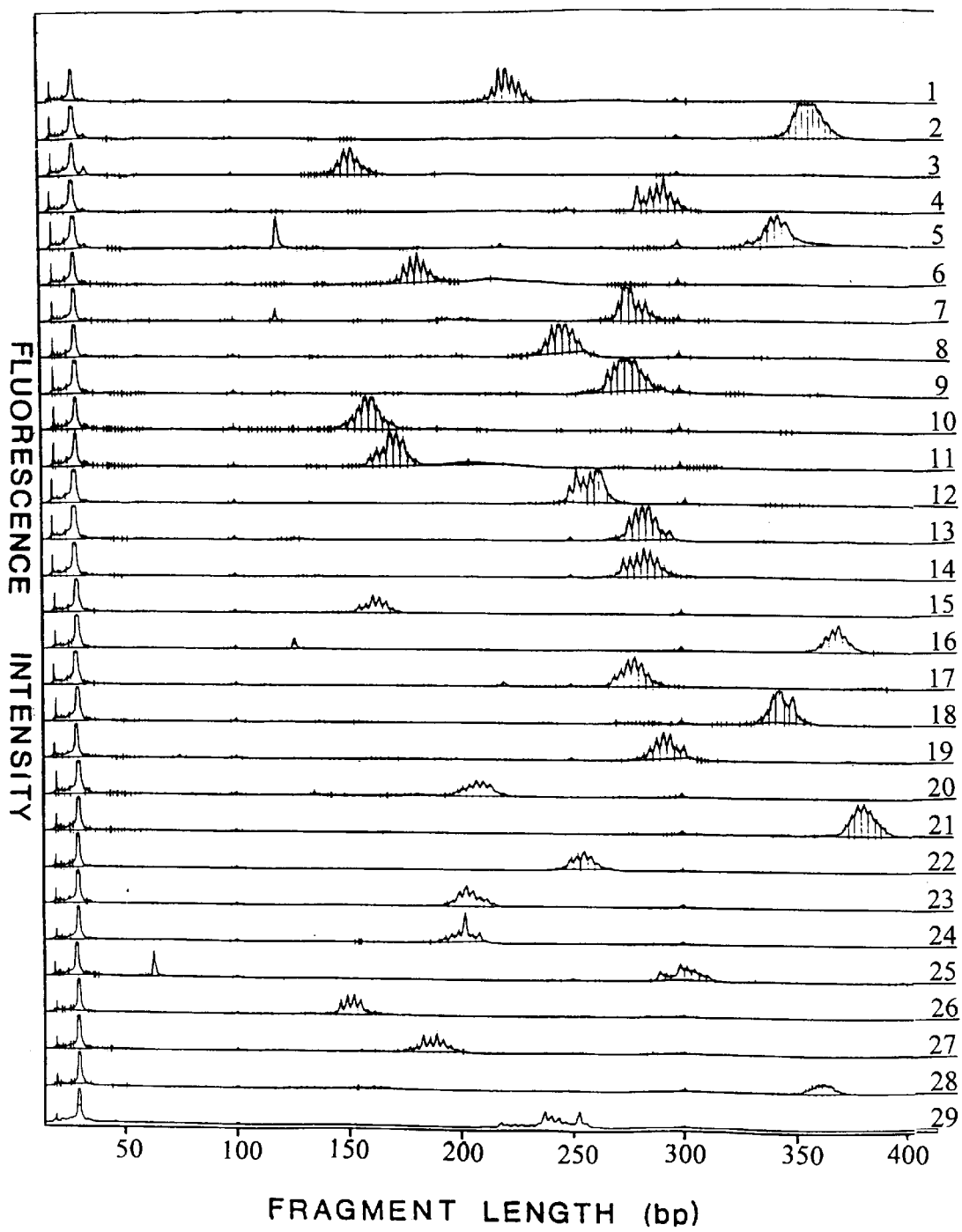
FIG. 8B graphically depicts intrafamily gene fragment length profiles generated and scaled automatically by the Fragment Manager™ 1.1 software used to analyze each profile after electrophoresis on a polyacrylamide gel. Fluorescence intensity is plotted as a function of fragment length (measured in base pairs). The double-PCR/elevated-annealing-temperature procedures described in Example 4 were used to generate the profiles. Lanes 1–29 depict the intrafamily gene fragment length profiles for gene families Vα1–Vα29, respectively. Each lane contains size standards of 100 and 300 nucleotides.
Figure 9A:
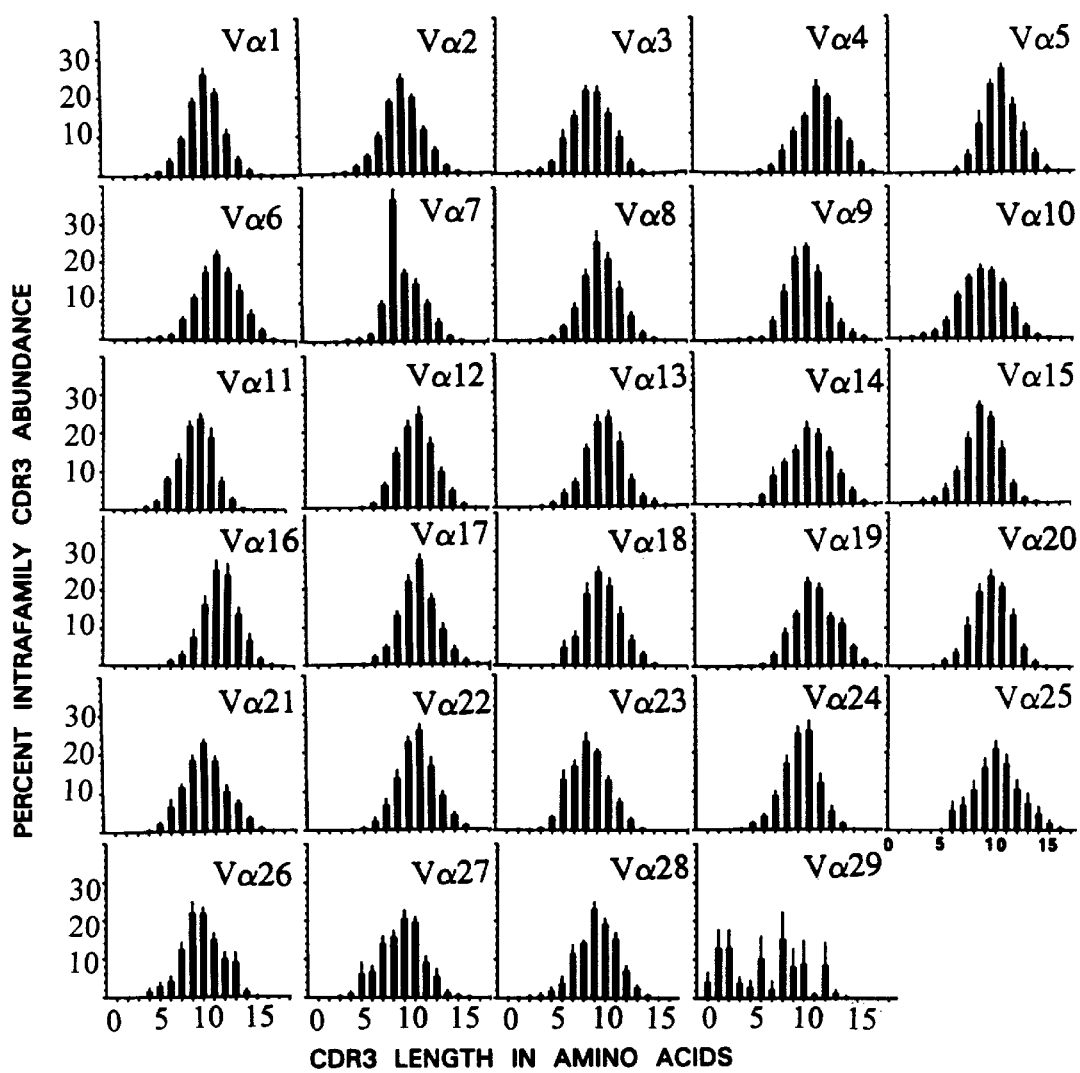
FIG. 9A depicts frequency distribution histograms of deduced CDR3 lengths for twenty-nine Vα families and subfamilies. Each histogram depicts an averaged frequency distribution of the CDR3 lengths in one Vα gene family, derived by averaging the intrafamily gene fragment length profiles obtained from eight healthy blood donors. The prevalence of each fragment in each donor's intrafamily gene fragment length profile was calculated by dividing the fluorescence peak area for the fragment by the total peak area observed for the profile. CDR3 lengths (in amino acids) for each Vα gene family were deduced from fragment lengths (in base pairs) measured from polyacrylamide gels. Standard error (SE) in the CDR3 fragment length prevalences are depicted with error bars in each histogram.
Figure 10:
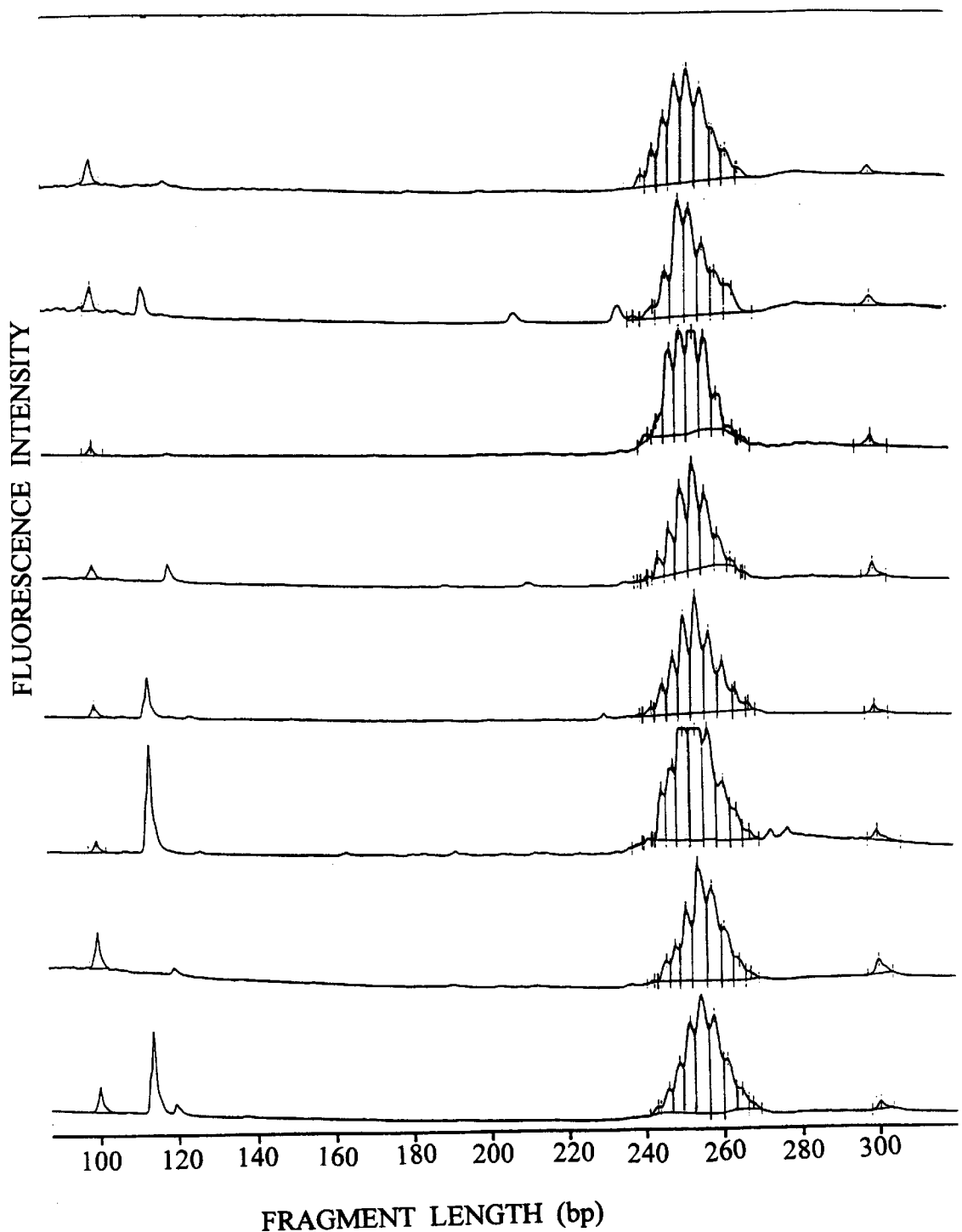
FIG. 10 depicts eight intrafamily gene fragment length profiles for the Vα14 gene family, derived from blood from eight healthy individuals. Peaks corresponding to 100 and 300 base pair size standards are visible in each profile.

The foregoing Vα intrafamily gene fragment analysis procedure provided Vα intrafamily gene fragment profiles having from 11 to 18 or more distinct CDR3 fragment peaks representing CDR3 lengths of 0 to 17 amino acids. As shown in FIG. 8B, the double-PCR/60° C.-annealing temperature procedure successfully eliminated most of the non-specific PCR products that were observed using a single PCR procedure. As shown in FIGS. 9A (histograms) and 9B (tabulation), the intrafamily gene fragment length profiles were consistently gaussian-like in appearance for each of the eight healthy blood donors for twenty-eight of the twenty-nine Vα families analyzed. For any particular Vα family, the gaussian-like distribution was strikingly similar for all eight healthy donors, as illustrated in FIG. 10 for the Vα14 family. The Vα29 profiles for all eight donors were not gaussion-like in appearance, but it is believed that selection of an alternative Vα29 primer will result in gaussian-like profiles.

Analysis of the data from these eight patients for families Vα1 to Vα28 reveals that the measured distance between contiguous nucleotide peaks was 2.92±0.34 nucleotides, in agreement with the predicted distance of 3 nucleotides. The lengths of 2,349 measured fragments fell within 0.84±0.04 nucleotides of their calculated lengths based on the PCR primer binding sites.

EXAMPLE 5

Improved T Cell Receptor Intrafamily Vα Gene Fragment Analysis

The intrafamily Vα gene fragment analysis procedure described in Example 4 is further improved to enhance efficiency, rapidity, and repeatability, in the same manner that the intrafamily Vβ gene fragment analysis procedure described in Example 1 is improved in Example 3. The following improved procedures permit intrafamily Vα gene fragment analysis for twenty-nine Vα families in a manner wherein only a single set of twenty-nine PCR reactions (plus controls) is conducted and wherein intrafamily gene fragment length profiles for all twenty-nine families are determined from analysis of a single polyacrylamide gel (wherein a sample from each of the PCR reactions has been electrophoresed).

cDNA Synthesis and PCR Expansion

A single, 33 µl cDNA synthesis reaction is conducted essentially as described in Example 4 using 1.0 µg total RNA and Pharmacia's cDNA kit. Family-specific and control PCR reactions also are set up and performed as described in Example 4.

Polyacrylamide Gel Sample Loading

As explained in detail in Example 3, the amount of family-specific PCR product loaded on the gel for any given family should be such that low-abundance peaks are detected at a minimum level of 50 peak area units while high-abundance peaks are detected at a maximum of about 8000 units (using Phamacia's A.L.F sequencer and Fragment Manager™ 1.1 software).

First, the averaged intrafamily gene fragment length profiles derived from healthy individuals and described in Example 4 (FIGS. 9A and 9B) were used to determine a theoretical maximum total peak area that would be preferred for each family, consistent with the limitation of having a maximum 8000 peak units of area for the most prevalent fragment in that family.

Proper sample volumes for all Vα family-specific PCR reactions are determined by performing an initial polyacrylamide gel analysis of each family-specific PCR reaction. For example, the initial analysis is conducted by electrophoresing an aliquot from the Cβ control PCR reaction and an aliquot from each Vα family-specific (second) PCR reaction of a healthy individual on a polyacrylamide gel and analyzing peak areas as described in Example 4. From the peak area measurements, a calculation is made to determine the proper subsequent aliquot from each Vα family-specific PCR reaction required to produce a profile having the theoretical preferred maximum total peak area for that family. For example, if a 1 µl aliquot from the Vα1 PCR reaction produced 8000 units of total Vα1 peak area (after summing all of the peaks in the Vα1 profile), then about 3.8 µl would constitute an aliquot to produce a profile having the theoretical preferred maximum total peak area of 30628 units.

A second polyacrylamide gel electrophoresis then is performed to generate intrafamily gene fragment length profiles for all twenty-nine Vα families. A sample from each Vα family-specific PCR reaction is loaded on the second gel, each sample size being selected such that (1) the total family peak area will be about 50–75% of the theoretical preferred maximum total peak area for that family; and (2) the total family peak area will be at least about 15,000 units, so that low-abundance peaks are observed. The sample volume is limited to 50–75% of the theoretical preferred maximum to insure against overloading of the most abundant peaks.

This systematic procedure for determining the proper sample size for gel loading will result in intrafamily Vα gene fragment length profiles wherein both high- and low-abundance fragment peaks are detected in each Vα profile without concomitant overloading of high-abundance fragments. Thus, using twenty-nine lanes on a single polyacrylamide gel, intrafamily Vα gene fragment length profiles are determined rapidly for all twenty-nine Vα families characterized in FIG. 9A.

Alternatively, acceptable Vα family-specific sample volumes are determined more rapidly by analyzing only one of the 29 families on the initial polyacrylamide gel. For example, an initial analysis is conducted by electrophoresing three different aliquots from the Vα1 family-specific PCR reaction on a polyacrylamide gel and analyzing peak areas as described in Example 4. From the peak area measurements of each lane, a calculation is made to determine the proper subsequent aliquot from the Vα1 reaction required to produce a profile having 50–75% of the theoretical preferred maximum total peak area for that family. For example, if a 3.8 µl aliquot of the Vα1 PCR reaction will produce a profile having the theoretical preferred maximum total peak area for Vα1, then an aliquot of about 1.9–2.9 µl is selected as a proper subsequent aliquot for generating a Vα1 intrafamily gene fragment length profile.

Acceptable aliquots for the remaining families are estimated using ratios provided in Table VII. Table VII presents the average prevalence of the largest peak in each Vα intrafamily gene fragment length profile, the standard deviation observed for this prevalence, and the theoretical preferred maximum total peak area for each family. Table VII also provides two ratios (right columns) for calculating acceptable sample volumes for the remaining families. Ratio A reflects the theoretical preferred maximum peak areas of each family, relative the theoretical preferred maximum peak area of Vα1. Ratio B reflects the total peak area observed in the indicated intrafamily gene fragment length profile derived from the blood of a single healthy individual relative to the total peak area observed in that individual's Vα1 profile, where an equal volume of PCR reaction product (e.g., 1.5 µl) was analyzed from each family-specific PCR reaction. For example, the calculated Vα7 family maximum peak area is about 70% of that of Vα1 (ratio A of 0.70); the Vα7 gene family was observed to have about 40% of the total peak are of the Vα1 gene family for the selected healthy individual (Ratio B of 0.40).

TABLE VII

POLYACRYLAMIDE GEL LOADING RATIOS FOR Vα FAMILIES

| Vα Family | Average largest peak | SD largest peak | Max. total peak area for family | Ratio A (to Vα1) | Ratio B (to Vα1) |
|---|---|---|---|---|---|
| 1 | 26.12% | 4.37% | 30628 | 1.00 | 1.00 |
| 2 | 24.66% | 3.21% | 32441 | 1.06 | 1.08 |
| 3 | 23.18% | 3.60% | 34513 | 1.13 | 1.52 |
| 4 | 22.96% | 3.18% | 34843 | 1.14 | 1.20 |
| 5 | 27.05% | 3.17% | 29575 | 0.97 | 0.29 |
| 6 | 23.09% | 3.02% | 34647 | 1.13 | 1.22 |
| 7 | 37.17% | 7.37% | 21523 | 0.70 | 0.40 |
| 8 | 24.13% | 3.19% | 33154 | 1.08 | 1.32 |
| 9 | 26.10% | 3.96% | 30651 | 1.00 | 0.29 |
| 10 | 19.50% | 3.31% | 41026 | 1.34 | 1.09 |
| 11 | 26.59% | 4.35% | 30086 | 0.98 | 0.84 |
| 12 | 26.14% | 3.78% | 30604 | 1.00 | 0.55 |
| 13 | 25.89% | 3.90% | 30900 | 1.01 | 0.35 |
| 14 | 21.87% | 3.23% | 36580 | 1.19 | 0.32 |
| 15 | 26.20% | 1.72% | 30534 | 1.00 | 0.36 |
| 16 | 30.17% | 4.07% | 26516 | 0.87 | 0.29 |
| 17 | 28.30% | 3.18% | 28269 | 0.92 | 0.43 |
| 18 | 27.39% | 3.95% | 29208 | 0.95 | 0.41 |
| 19 | 23.35% | 2.35% | 34261 | 1.12 | 0.45 |
| 20 | 26.11% | 3.50% | 30640 | 1.00 | 0.38 |
| 21 | 23.25% | 2.23% | 34409 | 1.12 | 0.05 |
| 22 | 26.86% | 2.53% | 29784 | 0.97 | 0.16 |
| 23 | 24.32% | 4.24% | 32895 | 1.07 | 0.32 |
| 24 | 29.12% | 4.63% | 27473 | 0.90 | 0.30 |
| 25 | 23.74% | 3.52% | 33698 | 1.10 | 0.16 |
| 26 | 24.77% | 5.68% | 32297 | 1.05 | 0.35 |
| 27 | 23.85% | 4.19% | 33543 | 1.10 | 0.15 |
| 28 | 25.33% | 3.54% | 31583 | 1.03 | 0.18 |
| 29 | 36.39% | 13.31% | 21984 | 0.72 | 0.15 |

An acceptable aliquot for the other Vα family-specific PCR reactions is calculated from the aliquot selected for the Vα1 reaction and from the peak area ratios A and B of Table VII, according to the following formula:

Volume$_{V\alpha N}$=Volume$_{V\alpha 1}$×(Ratio A$_{V\alpha N}$/ Ratio B$_{V\alpha N}$)

For example, if 2.5 µl were a proper aliquot from the Vα1 PCR reaction to load on a gel (to produce 50–75% of the theoretical preferred maximum total peak area), then 4.4 µl (i.e., 2.5×0.70/0.40) would be a proper aliquot for the Vα7 family.

It is expected that derivation of the ratio B column of Table VII by averaging total family peak area ratios determined from multiple healthy individuals will supply suitable ratio B values as well.

EXAMPLE 6

Determination of Complete Vα and Vβ Intrafamily Gene Fragment Profiles on a Single Polyacrylamide Gel From the foregoing examples it is apparent that twenty-nine Vα and twenty-five Vβ fragment profiles can be determined for an individual by conducting only 1–2 cDNA synthesis reactions, 54 family-specific (variable region) PCR expansions of the cDNA, 3 control PCR expansions, and electrophoretic analysis of the PCR reaction products on a polyacrylamide gel. It has been determined, moreover, that the 54 family-specific PCR expansion reactions can be analyzed effectively in a single polyacrylamide gel having as few as 29 lanes, by double- and triple-loading lanes.

More particularly, the various Vα and Vβ family-specific 5' PCR primers described herein bind to their respective Vα and Vβ genes at different positions relative to the location of the constant region 3' primer. These binding sites are identified in Tables I and VI. Therefore, in many instances the PCR fragments obtained in a family-specific PCR reaction have distinctly different sizes from the fragments obtained for other families (even though the CDR3 regions of all families are in the range of –1 to 22 amino acids). Thus, the fragment lengths of certain families migrate at distinctly different rates in a polyacrylamide gel, and can be resolved separately even when loaded in a single lane. Preferred multi-family gel loading combinations for the family-specific primers described herein are set forth in Table III.

TABLE VIII

Lane Combinations of TCR Alpha and Beta Chain PCR Reactions for Multiple Family Gel Loading

| Gel Lane | Vβ Family | Range of Fragment Lengths* (nucleotides) | Vβ Family | Range of Fragment Lengths* | Vβ Family | Range of Fragment Lengths* |
|---|---|---|---|---|---|---|
| 1 | Vα26 | 125–194 | Vα1 | 195–264 | Vα25 | 270–339 |
| 2 | Vα3 | 127–196 | Vβ12 | 198–267 | Vα5 | 314–383 |
| 3 | Vβ21 | 135–204 | Vβ18 | 204–273 | Vα18 | 316–385 |
| 4 | Vα10 | 136–205 | Vβ4 | 207–276 | Vβ22 | 316–385 |
| 5 | Vα15 | 137–206 | Vβ13.2 | 216–285 | Vβ24 | 329–398 |
| 6 | Vα11 | 146–215 | Vβ16 | 219–288 | Vα2 | 331–400 |
| 7 | Vα6 | 153–222 | Vβ5.1 | 223–292 | Vα28 | 332–401 |
| 8 | Vα27 | 161–230 | Vβ8 | 231–300 | Vα16 | 338–407 |
| 9 | Vβ5.2 | 162–231 | Vα9 | 247–316 | Vα21 | 353–422 |
| 10 | Vβ10 | 163–232 | Vα17 | 247–316 | | |
| 11 | Vβ6 | 165–234 | Vα14 | 252–321 | | |
| 12 | Vβ1 | 171–240 | Vα7 | 253–322 | | |
| 13 | Vβ3 | 171–240 | Vα13 | 254–323 | | |
| 14 | Vβ7 | 171–240 | Vβ23 | 258–327 | | |
| 15 | Vβ9 | 171–240 | Vα4 | 259–328 | | |
| 16 | Vβ14 | 171–240 | Vα19 | 262–331 | | |
| 17 | Vα24 | 172–241 | | | | |
| 18 | Vβ2 | 173–242 | | | | |
| 19 | Vβ15 | 174–243 | | | | |
| 20 | Vβ11 | 177–246 | | | | |
| 21 | Vα23 | 178–247 | | | | |
| 22 | Vα20 | 180–249 | | | | |
| 23 | Vβ13.1 | 198–267 | | | | |
| 24 | Vβ20 | 198–267 | | | | |
| 25 | Vα29 | 214–283 | | | | |
| 26 | Vβ17 | 219–288 | | | | |
| 27 | Vα8 | 220–289 | | | | |

TABLE VIII-continued

Lane Combinations of TCR Alpha and Beta Chain PCR Reactions for Multiple Family Gel Loading

| Gel Lane | Vβ Family | Range of Fragment Lengths* (nucleotides) | Vβ Family | Range of Fragment Lengths* | Vβ Family | Range of Fragment Lengths* |
|---|---|---|---|---|---|---|
| 28 | Vα12 | 226–295 | | | | |
| 29 | Vα22 | 226–295 | | | | |

*Range of fragment lengths is theoretical range if CDR3 lengths of –1 to 22 amino acids were all present in the Vβ profile.

The time and cost savings attributable to being able to determine intrafamily gene fragment analysis profiles for substantially all (i.e., greater than 95%) Vα and Vβ gene families for an individual on a single gel is a tremendous economic advantage of the present method of TCR repetoire analysis. This savings facilitates the adaptation of the present method to clinical settings.

EXAMPLE 7

Intrafamily Gene Fragment Analysis in a Patient Suffering from an Immune Disorder The intrafamily gene fragment analysis procedures of the present invention were performed using cell samples derived from a human patient (the cirrhosis patient) suffering from primary biliary cirrhosis, an autoimmune disorder of the liver. More particularly, RNA was purified from peripheral blood lymphocytes as described in the preceding examples and also from a liver tissue sample (approx. 30–100 mg of cells) obtained from the cirrhosis patient by ordinary liver biopsy procedures. Each RNA preparation was used to synthesize cDNA as described in the preceding examples.

Aliquots from each cDNA reaction (peripheral blood and liver) were used as template to perform family-specific PCR expansions for twenty-nine Vα and twenty-five Vβ gene families essentially as described in the preceding examples. The PCR reaction products were analyzed by polyacrylamide gel electrophoresis essentially as described in the preceding examples. It will be understood that the number of T lymphocytes present in other tissues (or in the liver tissue from patients suffering from different disorders) will vary, and the amount of RNA used to synthesize cDNA and the amount of cDNA template to use for PCR should be varied accordingly.

Figure 11A:
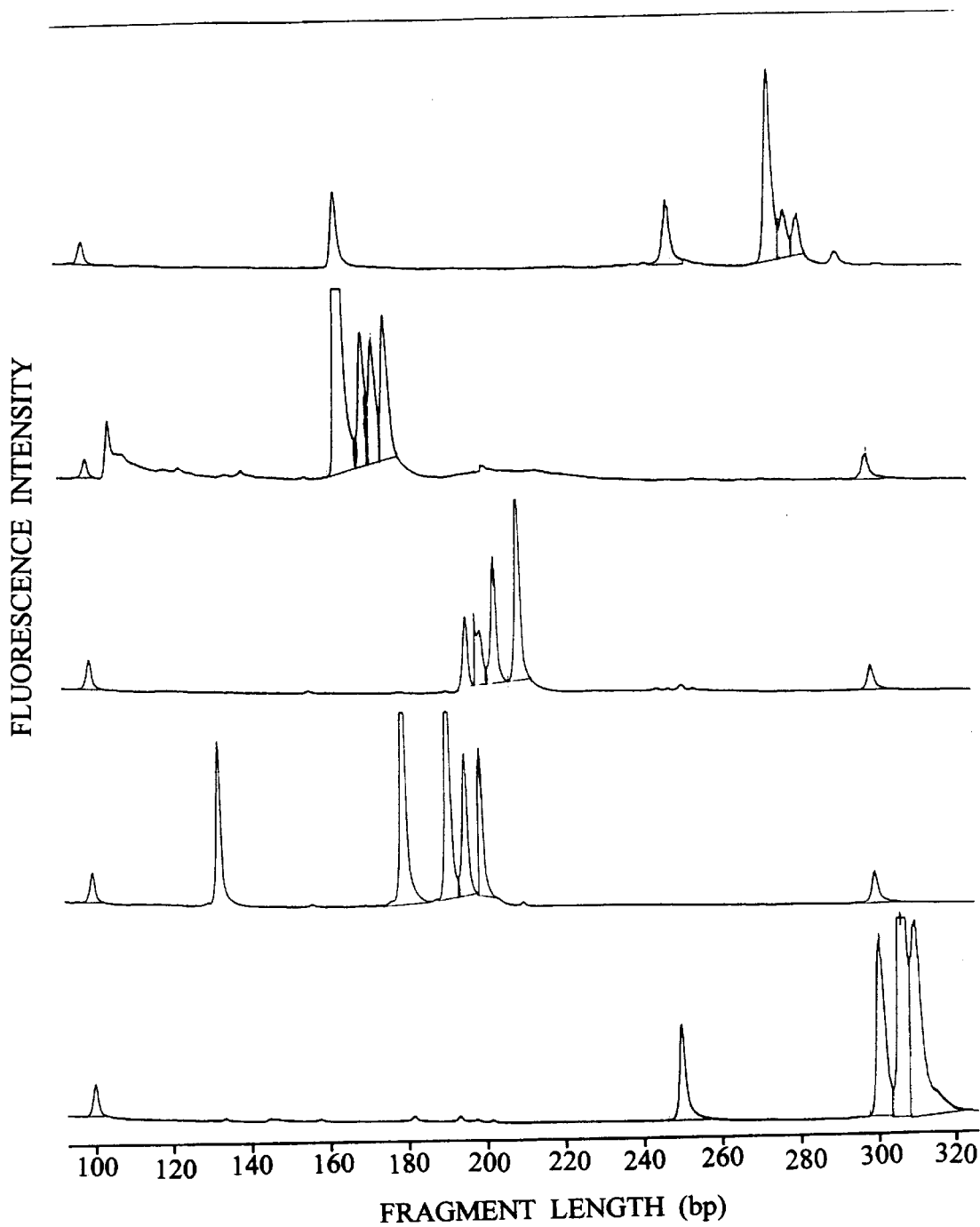
FIG. 11A depicts intrafamily gene fragment length profiles for (from top to bottom) the Vα9, Vα11, Vα23, Vα24, and Vα25 gene families, derived from a liver biopsy tissue sample of a patient suffering from primary biliary cirrhosis. Peaks corresponding to size standards (100 bp and 250 bp or 300 bp) are visible in each profile.
Figure 11B:
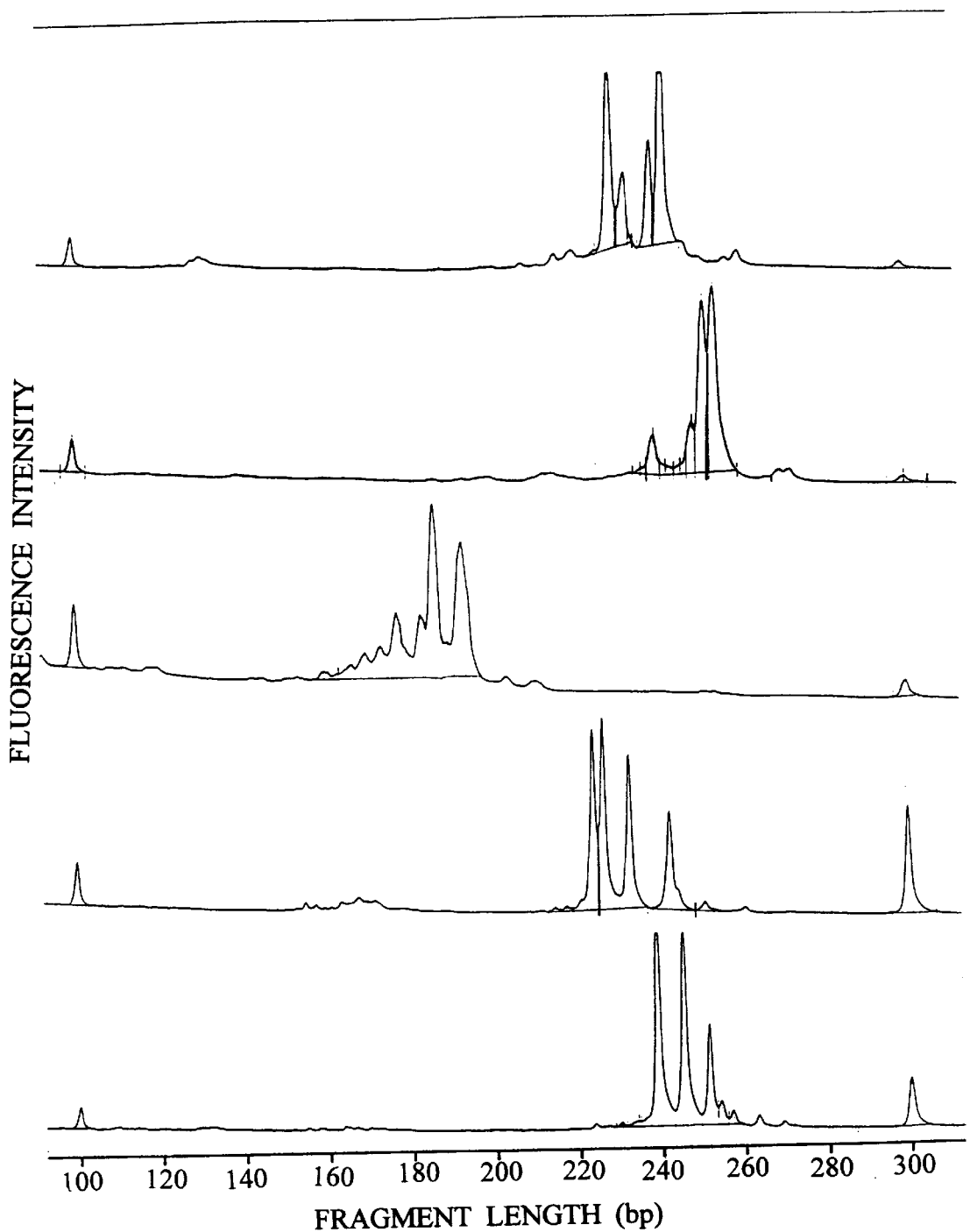
FIG. 11B depicts intrafamily gene fragment length profiles for (from top to bottom) the Vα4, V5.1, Vβ5.2, Vβ12, and Vβ13.2 gene families, derived from a liver biopsy tissue sample of a patient suffering from primary biliary cirrhosis. Peaks corresponding to 100 and 300 base pair size standards are visible in each profile.

FIGS. 11A and 11B depict exemplary intrafamily gene fragment length profiles for selected Vα and Vβ gene families derived from the cirrhosis patient's diseased liver tissue, infiltrated by auto-reactive T lymphocytes. These fragment profiles are highly distorted compared to the gaussian-like profiles derived from peripheral blood of healthy human subjects. They contain gaps where fragments observed in the healthy profiles are absent. Moreover, large fragment peaks are observed on the outside of the distributions (large and small CDR3 lengths) as opposed to only in the central areas of the distributions.

The complete intrafamily Vα and Vβ gene fragment length profiles from the cirrhosis patient's peripheral blood and liver are set forth in Tables IX and X, respectively, and compared to the corresponding healthy profiles derived from the peripheral blood of the eight healthy donors. More particularly, the first three columns of Tables IX and X (from left to right) identify the variable-region gene family being assayed, the PCR fragment lengths observed in that gene family in intrafamily gene fragment length profiles of healthy human subjects, and the corresponding deduced CDR3 lengths for those fragments. The fourth column ("Control Mean") depicts the prevalence of each particular fragment in the averaged intrafamily gene fragment length profiles derived from eight healthy individuals as described in Examples 1 and 4 and depicted in FIGS. 3A, 3B, 9A and 9B. Column 5 ("Control SD") depicts the standard deviation with respect to each mean fragment prevalence depicted in column 4.

Columns 6 and 7 in Tables IX and X depict the intrafamily gene fragment length profiles derived from peripheral blood mononuclear cells and liver biopsy tissue, respectively, from the cirrhosis patient. The prevalence of each fragment length observed is expressed as a percentage of the total of all fragment lengths in the profile. Finally, columns 8 and 9 in the tables present a statistical comparison of fragment prevalences in the cirrhosis patient profiles depicted in columns 6 and 7 with the average profiles of healthy human subjects depicted in columns 4 and 5. More particularly, each deviation between the cirrhosis patient profiles and the average profiles is presented as a multiple of the standard deviation observed in the average control profiles for each fragment.

TABLE IX

Intrafamily Fragment Analysis of V Alpha Gene CDR3 Regions from a Patient with Primary Biliary Cirrhosis

| Families | Fragment Length (nt) | CDR3 Length (aa) | Control Mean | Control SD | Patient PBMC | Patient Liver | X/SD* PBMC | X/SD* Liver |
|---|---|---|---|---|---|---|---|---|
| V Alpha 1 | 195 | 0 | | | | | | |
| V Alpha 1 | 198 | 1 | | | | | | |
| V Alpha 1 | 201 | 2 | 0.20% | | 0.04% | | | |
| V Alpha 1 | 204 | 3 | 0.37% | 0.26% | 0.34% | | −0.12 | |
| V Alpha 1 | 207 | 4 | 0.64% | 0.68% | 0.36% | | −0.42 | |
| V Alpha 1 | 210 | 5 | 1.28% | 0.54% | 2.19% | 2.14% | 1.68 | 1.59 |
| V Alpha 1 | 213 | 6 | 4.04% | 1.89% | 5.69% | 9.67% | 0.87 | 2.98 |
| V Alpha 1 | 216 | 7 | 9.95% | 1.66% | 12.14% | | 1.32 | |
| V Alpha 1 | 219 | 8 | 19.35% | 2.70% | 24.78% | 31.60% | 2.01 | 4.54 |
| V Alpha 1 | 222 | 9 | 26.12% | 4.37% | 25.70% | 28.00% | −0.10 | 0.43 |
| V Alpha 1 | 225 | 10 | 21.50% | 3.04% | 15.70% | 18.52% | −1.91 | −0.98 |
| V Alpha 1 | 228 | 11 | 10.82% | 3.58% | 9.64% | | −0.33 | |
| V Alpha 1 | 231 | 12 | 4.34% | 2.17% | 2.18% | 5.71% | −0.99 | 0.63 |
| V Alpha 1 | 234 | 13 | 1.73% | 1.22% | 1.23% | 4.36% | −0.41 | 2.17 |
| V Alpha 1 | 237 | 14 | 0.54% | 0.40% | | | | |
| V Alpha 1 | 240 | 15 | 0.16% | | | | | |
| V Alpha 1 | 243 | 16 | | | | | | |
| V Alpha 1 | 246 | 17 | | | | | | |
| V Alpha 1 | 249 | 18 | | | | | | |
| V Alpha 2 | 331 | 0 | | | | | | |
| V Alpha 2 | 334 | 1 | 0.06% | 0.02% | | | | |
| V Alpha 2 | 337 | 2 | 0.09% | 0.06% | | | | |
| V Alpha 2 | 340 | 3 | 0.39% | 0.10% | 0.24% | | −1.41 | |
| V Alpha 2 | 343 | 4 | 0.86% | 0.44% | 0.97% | | 0.26 | |
| V Alpha 2 | 346 | 5 | 1.92% | 1.24% | 1.13% | | −0.63 | |
| V Alpha 2 | 349 | 6 | 4.69% | 1.31% | 4.19% | | −0.38 | |
| V Alpha 2 | 352 | 7 | 9.96% | 2.31% | 9.37% | 19.90% | −0.25 | 4.30 |
| V Alpha 2 | 355 | 8 | 18.69% | 1.90% | 20.10% | 29.34% | 0.74 | 5.61 |
| V Alpha 2 | 358 | 9 | 24.41% | 3.56% | 26.36% | 23.77% | 0.55 | −0.18 |
| V Alpha 2 | 361 | 10 | 19.67% | 2.41% | 15.18% | 20.18% | −1.86 | 0.21 |
| V Alpha 2 | 364 | 11 | 11.36% | 2.53% | 12.09% | | 0.29 | |
| V Alpha 2 | 367 | 12 | 6.05% | 1.99% | 5.90% | 6.81% | −0.08 | 0.38 |
| V Alpha 2 | 370 | 13 | 1.97% | 0.76% | 3.76% | | 2.34 | |
| V Alpha 2 | 373 | 14 | 0.73% | 0.50% | 0.72% | | −0.01 | |
| V Alpha 2 | 376 | 15 | 0.31% | 0.23% | | | | |
| V Alpha 2 | 379 | 16 | | | | | | |
| V Alpha 2 | 382 | 17 | | | | | | |
| V Alpha 2 | 385 | 18 | | | | | | |
| V Alpha 3 | 127 | 0 | | | 0.18% | | | |
| V Alpha 3 | 130 | 1 | | | 0.27% | | | |
| V Alpha 3 | 133 | 2 | 0.34% | 0.45% | 0.25% | | −0.19 | |
| V Alpha 3 | 136 | 3 | 0.54% | 0.53% | 0.39% | | −0.28 | |
| V Alpha 3 | 139 | 4 | 1.07% | 1.25% | 1.39% | | 0.25 | |
| V Alpha 3 | 142 | 5 | 2.92% | 1.39% | 3.21% | | 0.21 | |
| V Alpha 3 | 145 | 6 | 9.02% | 6.10% | 7.31% | 40.36% | −0.28 | 5.14 |
| V Alpha 3 | 148 | 7 | 14.98% | 3.13% | 17.36% | | 0.76 | |
| V Alpha 3 | 151 | 8 | 21.31% | 3.43% | 21.74% | 32.08% | 0.12 | 3.14 |
| V Alpha 3 | 154 | 9 | 20.93% | 4.04% | 23.29% | | 0.58 | |
| V Alpha 3 | 157 | 10 | 15.60% | 3.22% | 15.16% | 27.56% | −0.14 | 3.71 |
| V Alpha 3 | 160 | 11 | 9.43% | 4.03% | 6.07% | | −0.83 | |
| V Alpha 3 | 163 | 12 | 2.82% | 2.13% | 2.52% | | −0.14 | |
| V Alpha 3 | 166 | 13 | 0.68% | 0.58% | 0.77% | | 0.17 | |
| V Alpha 3 | 169 | 14 | 0.06% | 0.11% | 0.08% | | 0.14 | |
| V Alpha 3 | 172 | 15 | 0.02% | 0.04% | | | | |
| V Alpha 3 | 175 | 16 | | | | | | |
| V Alpha 3 | 178 | 17 | | | | | | |
| V Alpha 3 | 181 | 18 | | | | | | |

TABLE IX-continued

Intrafamily Fragment Analysis of V Alpha Gene CDR3 Regions from a Patient with Primary Biliary Cirrhosis

| Families | Fragment Length (nt) | CDR3 Length (aa) | Control Mean | Control SD | Patient PBMC | Patient Liver | X/SD* PBMC | X/SD* Liver |
|---|---|---|---|---|---|---|---|---|
| V Alpha 4 | 259 | 0 | | | | | | |
| V Alpha 4 | 262 | 1 | | | | | | |
| V Alpha 4 | 265 | 2 | | | | | | |
| V Alpha 4 | 268 | 3 | | | | | | |
| V Alpha 4 | 271 | 4 | | | | | | |
| V Alpha 4 | 274 | 5 | 0.04% | 0.12% | | | | |
| V Alpha 4 | 277 | 6 | 0.68% | 0.63% | | | | |
| V Alpha 4 | 280 | 7 | 1.81% | 1.12% | 2.69% | 5.12% | 0.79 | 2.96 |
| V Alpha 4 | 283 | 8 | 5.70% | 4.11% | 5.15% | 17.95% | −0.13 | 2.98 |
| V Alpha 4 | 286 | 9 | 10.68% | 2.85% | 12.77% | 7.78% | 0.73 | −1.02 |
| V Alpha 4 | 289 | 10 | 14.80% | 2.00% | 16.94% | 12.66% | 1.07 | −1.07 |
| V Alpha 4 | 292 | 11 | 22.16% | 4.29% | 21.17% | 19.22% | −0.23 | −0.68 |
| V Alpha 4 | 295 | 12 | 19.68% | 1.73% | 23.83% | 37.26% | 2.40 | 10.17 |
| V Alpha 4 | 298 | 13 | 13.44% | 1.91% | 17.45% | | 2.11 | |
| V Alpha 4 | 301 | 14 | 8.05% | 1.80% | | | | |
| V Alpha 4 | 304 | 15 | 2.70% | 1.33% | | | | |
| V Alpha 4 | 307 | 16 | 0.49% | 0.40% | | | | |
| V Alpha 4 | 310 | 17 | 0.14% | 0.18% | | | | |
| V Alpha 4 | 313 | 18 | | | | | | |
| V Alpha 5 | 314 | 0 | | | | | | |
| V Alpha 5 | 317 | 1 | | | | | | |
| V Alpha 5 | 320 | 2 | | | | | | |
| V Alpha 5 | 323 | 3 | 0.05% | 0.15% | | | | |
| V Alpha 5 | 326 | 4 | 0.03% | 0.08% | | | | |
| V Alpha 5 | 329 | 5 | 0.09% | 0.18% | | | | |
| V Alpha 5 | 332 | 6 | 0.90% | 1.54% | | | | |
| V Alpha 5 | 335 | 7 | 4.55% | 3.44% | 21.52% | | 4.94 | |
| V Alpha 5 | 338 | 8 | 12.50% | 9.00% | 37.60% | 5.98% | 2.79 | −0.72 |
| V Alpha 5 | 341 | 9 | 22.45% | 2.86% | 25.13% | 50.09% | 0.94 | 9.67 |
| V Alpha 5 | 344 | 10 | 26.40% | 3.10% | 15.72% | 18.88% | −3.44 | −2.42 |
| V Alpha 5 | 347 | 11 | 17.16% | 4.71% | | 9.25% | | −1.68 |
| V Alpha 5 | 350 | 12 | 10.24% | 5.95% | | 9.87% | | −0.06 |
| V Alpha 5 | 353 | 13 | 4.66% | 2.96% | | | | |
| V Alpha 5 | 356 | 14 | 0.89% | 1.56% | | 5.93% | | 3.22 |
| V Alpha 5 | 359 | 15 | 0.07% | 0.20% | | | | |
| V Alpha 5 | 362 | 16 | | | | | | |
| V Alpha 5 | 365 | 17 | | | | | | |
| V Alpha 5 | 368 | 18 | | | | | | |
| V Alpha 6 | 153 | 0 | | | 0.23% | | | |
| V Alpha 6 | 156 | 1 | | | 0.55% | | | |
| V Alpha 6 | 159 | 2 | | | 1.12% | | | |
| V Alpha 6 | 162 | 3 | 0.13% | 0.26% | 0.94% | | 3.05 | |
| V Alpha 6 | 165 | 4 | 0.36% | 0.40% | 0.79% | 9.62% | 1.06 | 23.06 |
| V Alpha 6 | 168 | 5 | 0.65% | 0.57% | 1.75% | | 1.93 | |
| V Alpha 6 | 171 | 6 | 1.26% | 0.94% | 0.53% | | −0.78 | |
| V Alpha 6 | 174 | 7 | 5.39% | 2.08% | 4.86% | 6.41% | −0.25 | 0.49 |
| V Alpha 6 | 177 | 8 | 11.11% | 2.49% | 12.16% | | 0.42 | |
| V Alpha 6 | 180 | 9 | 17.79% | 4.37% | 14.91% | | −0.66 | |
| V Alpha 6 | 183 | 10 | 22.44% | 3.14% | 25.67% | 15.18% | 1.03 | −2.31 |
| V Alpha 6 | 186 | 11 | 17.81% | 3.40% | 19.49% | 38.41% | 0.49 | 6.06 |
| V Alpha 6 | 189 | 12 | 13.08% | 4.22% | 8.89% | 6.33% | −0.99 | −1.60 |
| V Alpha 6 | 192 | 13 | 6.87% | 3.03% | 4.90% | 9.05% | −0.65 | 0.72 |
| V Alpha 6 | 195 | 14 | 2.59% | 1.43% | 3.19% | 6.84% | 0.42 | 2.96 |
| V Alpha 6 | 198 | 15 | 0.36% | 0.48% | | 8.17% | | 16.25 |
| V Alpha 6 | 201 | 16 | 0.04% | 0.13% | | | | |
| V Alpha 6 | 204 | 17 | | | | | | |
| V Alpha 6 | 207 | 18 | | | | | | |
| V Alpha 7 | 253 | 0 | | | | | | |
| V Alpha 7 | 256 | 1 | | | | | | |
| V Alpha 7 | 259 | 2 | | | | | | |
| V Alpha 7 | 262 | 3 | 0.02% | 0.06% | | | | |
| V Alpha 7 | 265 | 4 | 0.51% | 0.69% | 0.18% | | −0.48 | |
| V Alpha 7 | 268 | 5 | 0.80% | 0.94% | 0.45% | | −0.36 | |
| V Alpha 7 | 271 | 6 | 1.80% | 1.00% | 1.18% | | −0.62 | |
| V Alpha 7 | 274 | 7 | 9.87% | 2.39% | 6.33% | | −1.48 | |
| V Alpha 7 | 277 | 8 | 37.00% | 7.32% | 36.54% | 66.09% | −0.08 | 3.97 |
| V Alpha 7 | 280 | 9 | 17.97% | 2.28% | 22.43% | | 1.96 | |
| V Alpha 7 | 283 | 10 | 15.09% | 3.87% | 23.99% | 15.28% | 2.30 | 0.05 |
| V Alpha 7 | 286 | 11 | 10.04% | 2.35% | 8.89% | 18.62% | −0.49 | 3.65 |
| V Alpha 7 | 289 | 12 | 5.03% | 2.62% | | | | |
| V Alpha 7 | 292 | 13 | 1.39% | 0.88% | | | | |
| V Alpha 7 | 295 | 14 | 0.42% | 0.45% | | | | |
| V Alpha 7 | 298 | 15 | 0.05% | 0.10% | | | | |

TABLE IX-continued

Intrafamily Fragment Analysis of V Alpha Gene CDR3 Regions
from a Patient with Primary Biliary Cirrhosis

| Families | Fragment Length (nt) | CDR3 Length (aa) | Control Mean | Control SD | Patient PBMC | Patient Liver | X/SD* PBMC | X/SD* Liver |
|---|---|---|---|---|---|---|---|---|
| V Alpha 7 | 301 | 16 | | | | | | |
| V Alpha 7 | 304 | 17 | | | | | | |
| V Alpha 7 | 307 | 18 | | | | | | |
| V Alpha 8 | 220 | 0 | | | | | | |
| V Alpha 8 | 223 | 1 | | | | | | |
| V Alpha 8 | 226 | 2 | 0.01% | 0.03% | | | | |
| V Alpha 8 | 229 | 3 | 0.05% | 0.14% | | | | |
| V Alpha 8 | 232 | 4 | 0.43% | 0.44% | | 1.50% | | 2.42 |
| V Alpha 8 | 235 | 5 | 1.01% | 0.82% | 0.59% | 5.52% | −0.51 | 5.48 |
| V Alpha 8 | 238 | 6 | 3.69% | 1.18% | 2.99% | 12.73% | −0.59 | 7.64 |
| V Alpha 8 | 241 | 7 | 8.45% | 3.66% | 9.02% | 17.12% | 0.15 | 2.37 |
| V Alpha 8 | 244 | 8 | 16.92% | 4.62% | 15.47% | 16.33% | −0.31 | −0.13 |
| V Alpha 8 | 247 | 9 | 25.74% | 8.58% | 23.34% | 19.56% | −0.28 | −0.72 |
| V Alpha 8 | 250 | 10 | 21.25% | 4.93% | 23.39% | 27.25% | 0.43 | 1.22 |
| V Alpha 8 | 253 | 11 | 13.55% | 5.04% | 15.67% | | 0.42 | |
| V Alpha 8 | 256 | 12 | 6.42% | 2.80% | 6.23% | | −0.07 | |
| V Alpha 8 | 259 | 13 | 1.81% | 1.43% | 2.56% | | 0.52 | |
| V Alpha 8 | 262 | 14 | 0.55% | 0.67% | 0.43% | | −0.19 | |
| V Alpha 8 | 265 | 15 | 0.11% | 0.22% | | | | |
| V Alpha 8 | 266 | 16 | 0.00% | 0.01% | | | | |
| V Alpha 8 | 271 | 17 | | | | | | |
| V Alpha 8 | 274 | 18 | | | | | | |
| V Alpha 9 | 247 | 0 | | | | | | |
| V Alpha 9 | 250 | 1 | | | | | | |
| V Alpha 9 | 253 | 2 | | | | | | |
| V Alpha 9 | 256 | 3 | 0.13% | 0.29% | 0.17% | | 0.12 | |
| V Alpha 9 | 259 | 4 | 0.34% | 0.46% | 0.98% | | 1.39 | |
| V Alpha 9 | 262 | 5 | 0.60% | 0.56% | 0.42% | | −0.33 | |
| V Alpha 9 | 265 | 6 | 0.70% | 0.76% | 0.27% | | −0.57 | |
| V Alpha 9 | 268 | 7 | 5.01% | 2.96% | 4.07% | | −0.32 | |
| V Alpha 9 | 271 | 8 | 12.63% | 5.21% | 17.29% | | 0.89 | |
| V Alpha 9 | 274 | 9 | 21.61% | 7.10% | 26.89% | | 0.74 | |
| V Alpha 9 | 277 | 10 | 24.28% | 2.16% | 30.15% | 70.66% | 2.72 | 21.52 |
| V Alpha 9 | 280 | 11 | 17.71% | 4.49% | 7.53% | 16.18% | −2.26 | −0.34 |
| V Alpha 9 | 283 | 12 | 9.73% | 4.49% | 10.09% | 13.17% | 0.06 | 0.77 |
| V Alpha 9 | 286 | 13 | 4.38% | 2.85% | 2.17% | | −0.78 | |
| V Alpha 9 | 289 | 14 | 1.86% | 2.20% | | | | |
| V Alpha 9 | 292 | 15 | 0.90% | 0.99% | | | | |
| V Alpha 9 | 295 | 16 | 0.12% | 0.23% | | | | |
| V Alpha 9 | 298 | 17 | | | | | | |
| V Alpha 9 | 301 | 18 | | | | | | |
| V Alpha 9 | 136 | 0 | 0.04% | 0.10% | | | | |
| V Alpha 10 | 139 | 1 | 0.16% | 0.29% | | | | |
| V Alpha 10 | 142 | 2 | 0.27% | 0.43% | | | | |
| V Alpha 10 | 145 | 3 | 1.05% | 1.17% | | | | |
| V Alpha 10 | 148 | 4 | 1.64% | 1.25% | 1.35% | 12.48% | −0.23 | 8.64 |
| V Alpha 10 | 151 | 5 | 5.95% | 3.31% | 5.17% | | −0.24 | |
| V Alpha 10 | 154 | 6 | 11.04% | 2.45% | 7.98% | | −1.25 | |
| V Alpha 10 | 157 | 7 | 15.14% | 3.29% | 15.46% | | 0.10 | |
| V Alpha 10 | 160 | 8 | 19.26% | 3.51% | 23.45% | 63.75% | 1.20 | 12.67 |
| V Alpha 10 | 163 | 9 | 17.12% | 2.77% | 25.14% | 23.78% | 2.90 | 2.41 |
| V Alpha 10 | 166 | 10 | 15.69% | 2.91% | 11.35% | | −1.49 | |
| V Alpha 10 | 169 | 11 | 8.89% | 3.42% | 7.26% | | −0.48 | |
| V Alpha 10 | 172 | 12 | 2.86% | 1.99% | 2.83% | | −0.01 | |
| V Alpha 10 | 175 | 13 | 0.67% | 0.68% | | | | |
| V Alpha 10 | 178 | 14 | 0.20% | 0.28% | | | | |
| V Alpha 10 | 181 | 15 | 0.03% | 0.09% | | | | |
| V Alpha 10 | 184 | 16 | | | | | | |
| V Alpha 10 | 187 | 17 | | | | | | |
| V Alpha 10 | 190 | 18 | | | | | | |
| V Alpha 11 | 146 | 0 | | | | | | |
| V Alpha 11 | 149 | 1 | | | | | | |
| V Alpha 11 | 152 | 2 | 0.03% | 0.09% | | | | |
| V Alpha 11 | 155 | 3 | 0.17% | 0.25% | | | | |
| V Alpha 11 | 158 | 4 | 0.86% | 0.69% | | | | |
| V Alpha 11 | 161 | 5 | 2.20% | 1.15% | 1.03% | | −1.01 | |
| V Alpha 11 | 164 | 6 | 8.17% | 1.68% | 8.51% | 57.17% | 0.20 | 29.13 |
| V Alpha 11 | 167 | 7 | 13.36% | 4.07% | 15.69% | | 0.57 | |
| V Alpha 11 | 170 | 8 | 21.84% | 4.13% | 30.79% | 14.07% | 2.17 | −1.88 |
| V Alpha 11 | 173 | 9 | 23.77% | 3.63% | 25.05% | 13.05% | 0.35 | −2.95 |
| V Alpha 11 | 176 | 10 | 18.87% | 7.01% | 13.45% | 15.70% | −0.77 | −0.45 |
| V Alpha 11 | 179 | 11 | 7.49% | 2.50% | 4.38% | | −1.25 | |
| V Alpha 11 | 182 | 12 | 2.74% | 1.38% | 1.10% | | −1.19 | |

TABLE IX-continued

Intrafamily Fragment Analysis of V Alpha Gene CDR3 Regions
from a Patient with Primary Biliary Cirrhosis

| Families | Fragment Length (nt) | CDR3 Length (aa) | Control Mean | Control SD | Patient PBMC | Patient Liver | X/SD* PBMC | X/SD* Liver |
|---|---|---|---|---|---|---|---|---|
| V Alpha 11 | 185 | 13 | 0.46% | 0.32% | | | | |
| V Alpha 11 | 188 | 14 | | | | | | |
| V Alpha 11 | 191 | 15 | | | | | | |
| V Alpha 11 | 194 | 16 | | | | | | |
| V Alpha 11 | 197 | 17 | | | | | | |
| V Alpha 11 | 200 | 18 | | | | | | |
| V Alpha 12 | 226 | 0 | | | | | | |
| V Alpha 12 | 229 | 1 | | | | | | |
| V Alpha 12 | 232 | 2 | | | | | | |
| V Alpha 12 | 235 | 3 | 0.04% | 0.11% | | | | |
| V Alpha 12 | 238 | 4 | 0.05% | 0.10% | | | | |
| V Alpha 12 | 241 | 5 | 0.22% | 0.31% | | | | |
| V Alpha 12 | 244 | 6 | 1.21% | 0.70% | 0.35% | | −1.22 | |
| V Alpha 12 | 247 | 7 | 6.01% | 2.03% | 4.48% | | −0.75 | |
| V Alpha 12 | 250 | 8 | 14.57% | 3.84% | 15.31% | 18.99% | 0.19 | 1.15 |
| V Alpha 12 | 253 | 9 | 21.31% | 4.76% | 27.56% | 5.11% | 1.31 | −3.40 |
| V Alpha 12 | 256 | 10 | 24.47% | 5.85% | 22.32% | 31.34% | −0.37 | 1.17 |
| V Alpha 12 | 259 | 11 | 16.93% | 4.42% | 14.42% | 19.04% | −0.57 | 0.48 |
| V Alpha 12 | 262 | 12 | 9.41% | 3.18% | 8.25% | 14.64% | −0.36 | 1.65 |
| V Alpha 12 | 265 | 13 | 4.47% | 1.94% | 5.53% | | 0.55 | |
| V Alpha 12 | 268 | 14 | 1.09% | 0.77% | 1.79% | 10.88% | 0.91 | 12.79 |
| V Alpha 12 | 271 | 15 | 0.23% | 0.45% | | | | |
| V Alpha 12 | 274 | 16 | | | | | | |
| V Alpha 12 | 277 | 17 | | | | | | |
| V Alpha 12 | 280 | 18 | | | | | | |
| V Alpha 13 | 254 | 0 | | | | | | |
| V Alpha 13 | 257 | 1 | | | | | | |
| V Alpha 13 | 260 | 2 | | | | | | |
| V Alpha 13 | 263 | 3 | 0.13% | 0.24% | | | | |
| V Alpha 13 | 266 | 4 | 0.35% | 0.48% | 1.51% | | 2.43 | |
| V Alpha 13 | 269 | 5 | 1.12% | 1.15% | 2.93% | | 1.57 | |
| V Alpha 13 | 272 | 6 | 3.56% | 2.55% | 5.36% | | 0.71 | |
| V Alpha 13 | 275 | 7 | 6.42% | 2.55% | 7.83% | | 0.55 | |
| V Alpha 13 | 278 | 8 | 15.19% | 3.06% | 15.86% | 42.56% | 0.22 | 8.94 |
| V Alpha 13 | 281 | 9 | 22.03% | 5.13% | 21.57% | 22.61% | −0.09 | 0.11 |
| V Alpha 13 | 284 | 10 | 23.34% | 4.88% | 20.91% | 23.26% | −0.50 | −0.02 |
| V Alpha 13 | 287 | 11 | 16.85% | 6.80% | 11.27% | | −0.82 | |
| V Alpha 13 | 290 | 12 | 6.95% | 3.71% | 10.07% | 11.55% | 0.84 | 1.24 |
| V Alpha 13 | 293 | 13 | 2.53% | 2.02% | 2.06% | | −0.23 | |
| V Alpha 13 | 296 | 14 | 1.23% | 1.88% | 0.61% | | −0.33 | |
| V Alpha 13 | 299 | 15 | 0.26% | 0.56% | | | | |
| V Alpha 13 | 302 | 16 | 0.04% | 0.12% | | | | |
| V Alpha 13 | 305 | 17 | | | | | | |
| V Alpha 13 | 308 | 18 | | | | | | |
| V Alpha 14 | 252 | 0 | | | | | | |
| V Alpha 14 | 255 | 1 | | | | | | |
| V Alpha 14 | 258 | 2 | | | | | | |
| V Alpha 14 | 261 | 3 | 0.04% | 0.07% | | | | |
| V Alpha 14 | 264 | 4 | 0.14% | 0.20% | 0.33% | | 0.98 | |
| V Alpha 14 | 267 | 5 | 0.18% | 0.34% | 0.20% | | 0.07 | |
| V Alpha 14 | 270 | 6 | 2.42% | 1.07% | 0.96% | | −1.37 | |
| V Alpha 14 | 273 | 7 | 7.50% | 6.26% | 3.80% | 17.48% | −0.59 | 1.59 |
| V Alpha 14 | 276 | 8 | 11.06% | 2.36% | 13.11% | | 0.87 | |
| V Alpha 14 | 279 | 9 | 14.26% | 3.52% | 16.23% | 5.45% | 0.56 | −2.51 |
| V Alpha 14 | 282 | 10 | 19.89% | 4.93% | 20.36% | 48.15% | 0.10 | 5.73 |
| V Alpha 14 | 285 | 11 | 18.48% | 3.40% | 18.97% | 18.68% | 0.14 | 0.06 |
| V Alpha 14 | 288 | 12 | 13.73% | 3.28% | 12.91% | 10.27% | −0.25 | −1.06 |
| V Alpha 14 | 291 | 13 | 7.89% | 2.91% | 9.03% | | 0.39 | |
| V Alpha 14 | 294 | 14 | 3.50% | 2.05% | 3.27% | | −0.11 | |
| V Alpha 14 | 297 | 15 | 0.70% | 0.85% | 0.77% | | 0.08 | |
| V Alpha 14 | 300 | 16 | 0.19% | 0.37% | 0.05% | | −0.38 | |
| V Alpha 14 | 303 | 17 | | | | | | |
| V Alpha 14 | 306 | 18 | | | | | | |
| V Alpha 15 | 137 | 0 | | | | | | |
| V Alpha 15 | 140 | 1 | | | | | | |
| V Alpha 15 | 143 | 2 | 0.03% | 0.08% | | | | |
| V Alpha 15 | 146 | 3 | 0.63% | 1.66% | | | | |
| V Alpha 15 | 149 | 4 | 1.20% | 1.35% | | | | |
| V Alpha 15 | 152 | 5 | 3.68% | 3.47% | 3.16% | | −0.15 | |
| V Alpha 15 | 155 | 6 | 8.38% | 2.84% | 9.56% | | 0.42 | |
| V Alpha 15 | 158 | 7 | 16.90% | 4.06% | 17.12% | 49.29% | 0.05 | 7.98 |
| V Alpha 15 | 161 | 8 | 25.53% | 2.61% | 22.34% | 16.59% | −1.22 | −3.43 |
| V Alpha 15 | 164 | 9 | 22.53% | 3.55% | 29.63% | 14.51% | 2.00 | −2.26 |

TABLE IX-continued

Intrafamily Fragment Analysis of V Alpha Gene CDR3 Regions
from a Patient with Primary Biliary Cirrhosis

| Families | Fragment Length (nt) | CDR3 Length (aa) | Control Mean | Control SD | Patient PBMC | Patient Liver | X/SD* PBMC | X/SD* Liver |
|---|---|---|---|---|---|---|---|---|
| V Alpha 15 | 167 | 10 | 14.31% | 5.24% | 14.28% | 3.02% | 0.00 | −2.15 |
| V Alpha 15 | 170 | 11 | 5.06% | 2.50% | 3.94% | | −0.45 | |
| V Alpha 15 | 173 | 12 | 1.31% | 0.81% | | 16.60% | | 18.96 |
| V Alpha 15 | 176 | 13 | 0.39% | 0.48% | | | | |
| V Alpha 15 | 179 | 14 | 0.05% | 0.13% | | | | |
| V Alpha 15 | 182 | 15 | | | | | | |
| V Alpha 15 | 185 | 16 | | | | | | |
| V Alpha 15 | 188 | 17 | | | | | | |
| V Alpha 15 | 191 | 18 | | | | | | |
| V Alpha 16 | 338 | 0 | | | | | | |
| V Alpha 16 | 341 | 1 | | | | | | |
| V Alpha 16 | 344 | 2 | | | | | | |
| V Alpha 16 | 347 | 3 | | | | | | |
| V Alpha 16 | 350 | 4 | | | | | | |
| V Alpha 16 | 353 | 5 | 0.13% | 0.24% | | | | |
| V Alpha 16 | 356 | 6 | 1.30% | 1.30% | | | | |
| V Alpha 16 | 359 | 7 | 2.94% | 2.56% | | | | |
| V Alpha 16 | 362 | 8 | 7.55% | 6.32% | 4.16% | 3.47% | −0.54 | −0.65 |
| V Alpha 16 | 365 | 9 | 16.29% | 6.39% | 7.67% | | −1.35 | |
| V Alpha 16 | 368 | 10 | 25.15% | 7.53% | 36.77% | 45.31% | 1.54 | 2.68 |
| V Alpha 16 | 371 | 11 | 23.93% | 8.36% | 31.29% | | 0.88 | |
| V Alpha 16 | 374 | 12 | 13.84% | 4.87% | 14.22% | 3.36% | 0.08 | −2.15 |
| V Alpha 16 | 377 | 13 | 6.64% | 5.33% | 5.90% | 47.87% | −0.14 | 7.74 |
| V Alpha 16 | 380 | 14 | 1.77% | 1.35% | | | | |
| V Alpha 16 | 383 | 15 | 0.42% | 0.63% | | | | |
| V Alpha 16 | 386 | 16 | 0.03% | 0.08% | | | | |
| V Alpha 16 | 369 | 17 | | | | | | |
| V Alpha 16 | 392 | 18 | | | | | | |
| V Alpha 17 | 247 | 0 | | | | | | |
| V Alpha 17 | 250 | 1 | | | | | | |
| V Alpha 17 | 253 | 2 | | | | | | |
| V Alpha 17 | 256 | 3 | | | | | | |
| V Alpha 17 | 259 | 4 | | | 0.37% | | | |
| V Alpha 17 | 262 | 5 | 0.24% | 0.34% | 1.19% | | 2.85 | |
| V Alpha 17 | 265 | 6 | 1.91% | 1.17% | 2.13% | 7.94% | 0.19 | 5.16 |
| V Alpha 17 | 268 | 7 | 4.54% | 1.65% | 12.04% | 13.51% | 4.54 | 5.43 |
| V Alpha 17 | 271 | 8 | 12.93% | 3.13% | 9.25% | 24.00% | −1.18 | 3.54 |
| V Alpha 17 | 274 | 9 | 21.73% | 4.68% | 19.31% | 19.80% | −0.52 | −0.41 |
| V Alpha 17 | 277 | 10 | 27.32% | 4.12% | 26.64% | 6.10% | −0.16 | −5.15 |
| V Alpha 17 | 280 | 11 | 17.23% | 3.30% | 17.12% | 28.65% | −0.03 | 3.46 |
| V Alpha 17 | 283 | 12 | 9.18% | 4.21% | 8.05% | | −0.27 | |
| V Alpha 17 | 286 | 13 | 3.68% | 2.85% | 3.88% | | 0.07 | |
| V Alpha 17 | 289 | 14 | 0.97% | 1.41% | | | | |
| V Alpha 17 | 292 | 15 | 0.24% | 0.68% | | | | |
| V Alpha 17 | 295 | 16 | | | | | | |
| V Alpha 17 | 298 | 17 | | | | | | |
| V Alpha 17 | 301 | 18 | | | | | | |
| V Alpha 18 | 316 | 0 | | | | | | |
| V Alpha 18 | 319 | 1 | | | | | | |
| V Alpha 18 | 322 | 2 | | | | | | |
| V Alpha 18 | 325 | 3 | | | | | | |
| V Alpha 18 | 328 | 4 | 0.02% | 0.05% | | | | |
| V Alpha 18 | 331 | 5 | 0.19% | 0.37% | 0.89% | | 1.86 | |
| V Alpha 18 | 334 | 6 | 4.68% | 5.15% | 2.55% | | −0.41 | |
| V Alpha 18 | 337 | 7 | 7.48% | 4.24% | 9.71% | | 0.53 | |
| V Alpha 18 | 340 | 8 | 18.94% | 8.20% | 26.61% | | 0.94 | |
| V Alpha 18 | 343 | 9 | 24.70% | 3.56% | 20.03% | 64.03% | −1.31 | 11.05 |
| V Alpha 18 | 346 | 10 | 21.04% | 5.87% | 15.54% | 35.97% | −0.94 | 2.54 |
| V Alpha 18 | 349 | 11 | 13.75% | 5.03% | 10.04% | | −0.74 | |
| V Alpha 18 | 352 | 12 | 6.64% | 3.48% | 7.72% | | 0.31 | |
| V Alpha 18 | 355 | 13 | 2.92% | 2.07% | 4.44% | | 0.73 | |
| V Alpha 18 | 358 | 14 | 0.57% | 0.65% | 1.77% | | 1.85 | |
| V Alpha 18 | 361 | 15 | | | 0.70% | | | |
| V Alpha 18 | 364 | 16 | | | | | | |
| V Alpha 18 | 367 | 17 | | | | | | |
| V Alpha 18 | 370 | 18 | | | | | | |
| V Alpha 19 | 262 | 0 | | | | | | |
| V Alpha 19 | 265 | 1 | | | | | | |
| V Alpha 19 | 268 | 2 | | | | | | |
| V Alpha 19 | 271 | 3 | | | | | | |
| V Alpha 19 | 274 | 4 | 0.07% | 0.19% | | | | |
| V Alpha 19 | 277 | 5 | 0.15% | 0.23% | 0.93% | | 3.34 | |
| V Alpha 19 | 280 | 6 | 0.54% | 0.49% | 4.45% | | 8.01 | |

TABLE IX-continued

Intrafamily Fragment Analysis of V Alpha Gene CDR3 Regions from a Patient with Primary Biliary Cirrhosis

| Families | Fragment Length (nt) | CDR3 Length (aa) | Control Mean | Control SD | Patient PBMC | Patient Liver | X/SD* PBMC | X/SD* Liver |
|---|---|---|---|---|---|---|---|---|
| V Alpha 19 | 283 | 7 | 3.01% | 1.90% | 6.08% | | 1.61 | |
| V Alpha 19 | 286 | 8 | 8.65% | 3.59% | 8.88% | | 0.06 | |
| V Alpha 19 | 289 | 9 | 13.82% | 2.18% | 16.88% | | 1.41 | |
| V Alpha 19 | 292 | 10 | 22.14% | 3.29% | 21.30% | 29.15% | −0.25 | 2.13 |
| V Alpha 19 | 295 | 11 | 20.49% | 3.48% | 18.10% | 70.86% | −0.69 | 14.46 |
| V Alpha 19 | 298 | 12 | 13.09% | 2.44% | 11.08% | | −0.68 | |
| V Alpha 19 | 301 | 13 | 11.04% | 3.68% | 7.28% | | −1.02 | |
| V Alpha 19 | 304 | 14 | 4.94% | 1.60% | 2.40% | | −1.59 | |
| V Alpha 19 | 307 | 15 | 1.58% | 0.82% | 2.63% | | 1.27 | |
| V Alpha 19 | 310 | 16 | 0.41% | 0.71% | | | | |
| V Alpha 19 | 313 | 17 | 0.06% | 0.17% | | | | |
| V Alpha 19 | 316 | 18 | | | | | | |
| V Alpha 20 | 180 | 0 | | | | | | |
| V Alpha 20 | 183 | 1 | | | | | | |
| V Alpha 20 | 186 | 2 | | | | | | |
| V Alpha 20 | 189 | 3 | 0.06% | 0.12% | | | | |
| V Alpha 20 | 192 | 4 | 0.28% | 0.38% | | | | |
| V Alpha 20 | 195 | 5 | 1.55% | 1.38% | | | | |
| V Alpha 20 | 198 | 6 | 3.58% | 2.42% | 5.72% | | 0.88 | |
| V Alpha 20 | 201 | 7 | 10.69% | 6.01% | 14.57% | | 0.65 | |
| V Alpha 20 | 204 | 8 | 19.57% | 5.53% | 14.80% | 73.80% | −0.86 | 9.80 |
| V Alpha 20 | 207 | 9 | 23.59% | 4.47% | 21.05% | | −0.57 | |
| V Alpha 20 | 210 | 10 | 20.87% | 3.02% | 16.20% | 10.08% | −1.55 | −3.57 |
| V Alpha 20 | 213 | 11 | 13.34% | 4.58% | 13.70% | | 0.08 | |
| V Alpha 20 | 216 | 12 | 5.03% | 1.66% | 4.79% | | −0.14 | |
| V Alpha 20 | 219 | 13 | 1.24% | 1.18% | 6.20% | 16.11% | 4.22 | 12.64 |
| V Alpha 20 | 222 | 14 | 0.18% | 0.33% | 2.97% | | 8.44 | |
| V Alpha 20 | 225 | 15 | 0.02% | 0.05% | | | | |
| V Alpha 20 | 228 | 16 | | | | | | |
| V Alpha 20 | 231 | 17 | | | | | | |
| V Alpha 20 | 234 | 18 | | | | | | |
| V Alpha 21 | 353 | 0 | | | | | | |
| V Alpha 21 | 356 | 1 | | | | | | |
| V Alpha 21 | 359 | 2 | | | | | | |
| V Alpha 21 | 362 | 3 | | | | | | |
| V Alpha 21 | 365 | 4 | 0.37% | 0.39% | | | | |
| V Alpha 21 | 368 | 5 | 1.96% | 1.30% | | | | |
| V Alpha 21 | 371 | 6 | 6.42% | 5.35% | 3.86% | | −0.48 | |
| V Alpha 21 | 374 | 7 | 11.44% | 2.69% | 5.54% | 4.62% | −2.19 | −2.53 |
| V Alpha 21 | 377 | 8 | 18.22% | 3.97% | 7.32% | 24.75% | −2.75 | 1.65 |
| V Alpha 21 | 380 | 9 | 22.61% | 2.79% | 26.60% | 26.44% | 1.43 | 1.37 |
| V Alpha 21 | 383 | 10 | 17.89% | 3.65% | 23.51% | 7.22% | 1.54 | −2.92 |
| V Alpha 21 | 386 | 11 | 10.13% | 4.63% | 19.27% | 18.24% | 1.97 | 1.75 |
| V Alpha 21 | 389 | 12 | 7.05% | 2.26% | 12.37% | 12.59% | 2.35 | 2.45 |
| V Alpha 21 | 392 | 13 | 3.08% | 1.24% | 1.54% | 6.14% | −1.24 | 2.47 |
| V Alpha 21 | 395 | 14 | 0.69% | 0.85% | | | | |
| V Alpha 21 | 398 | 15 | 0.03% | 0.09% | | | | |
| V Alpha 21 | 401 | 16 | | | | | | |
| V Alpha 21 | 0 | 17 | | | | | | |
| V Alpha 21 | 0 | 18 | | | | | | |
| V Alpha 22 | 226 | 0 | | | | | | |
| V Alpha 22 | 229 | 1 | | | | | | |
| V Alpha 22 | 232 | 2 | | | | | | |
| V Alpha 22 | 235 | 3 | | | | | | |
| V Alpha 22 | 238 | 4 | 0.07% | 0.13% | | 0.57% | | 3.94 |
| V Alpha 22 | 241 | 5 | 0.50% | 0.74% | | 1.05% | | 0.74 |
| V Alpha 22 | 244 | 6 | 2.30% | 2.24% | 1.93% | 1.13% | −0.16 | −0.52 |
| V Alpha 22 | 247 | 7 | 6.34% | 4.54% | 3.82% | 18.48% | −0.55 | 2.67 |
| V Alpha 22 | 250 | 8 | 13.26% | 5.84% | 17.58% | 16.07% | 0.74 | 0.48 |
| V Alpha 22 | 253 | 9 | 22.44% | 3.73% | 17.44% | 36.74% | −1.34 | 3.83 |
| V Alpha 22 | 256 | 10 | 25.48% | 4.36% | 22.63% | 20.55% | −0.65 | −1.13 |
| V Alpha 22 | 259 | 11 | 16.18% | 6.63% | 19.91% | 5.42% | 0.56 | −1.62 |
| V Alpha 22 | 262 | 12 | 8.62% | 2.98% | 9.71% | | 0.37 | |
| V Alpha 22 | 265 | 13 | 3.65% | 2.00% | 4.15% | | 0.25 | |
| V Alpha 22 | 268 | 14 | 1.00% | 0.87% | 2.82% | | 2.09 | |
| V Alpha 22 | 271 | 15 | 0.16% | 0.29% | | | | |
| V Alpha 22 | 274 | 16 | | | | | | |
| V Alpha 22 | 277 | 17 | | | | | | |
| V Alpha 22 | 280 | 18 | | | | | | |
| V Alpha 23 | 178 | 0 | | | | | | |
| V Alpha 23 | 181 | 1 | | | | | | |
| V Alpha 23 | 184 | 2 | 0.16% | 0.32% | | | | |
| V Alpha 23 | 187 | 3 | 0.19% | 0.21% | | | | |

TABLE IX-continued

Intrafamily Fragment Analysis of V Alpha Gene CDR3 Regions from a Patient with Primary Biliary Cirrhosis

| Families | Fragment Length (nt) | CDR3 Length (aa) | Control Mean | Control SD | Patient PBMC | Patient Liver | X/SD* PBMC | X/SD* Liver |
|---|---|---|---|---|---|---|---|---|
| V Alpha 23 | 190 | 4 | 0.59% | 0.47% | 0.23% | | −0.78 | |
| V Alpha 23 | 193 | 5 | 3.36% | 0.96% | 1.58% | | −1.86 | |
| V Alpha 23 | 196 | 6 | 13.00% | 6.68% | 8.72% | 14.03% | −0.64 | 0.15 |
| V Alpha 23 | 199 | 7 | 16.40% | 4.20% | 19.02% | 16.73% | 0.63 | 0.08 |
| V Alpha 23 | 202 | 8 | 22.81% | 6.11% | 22.22% | 28.50% | −0.10 | 0.93 |
| V Alpha 23 | 205 | 9 | 20.17% | 1.83% | 25.72% | | 3.03 | |
| V Alpha 23 | 208 | 10 | 12.96% | 2.58% | 11.22% | 40.74% | −0.67 | 10.76 |
| V Alpha 23 | 211 | 11 | 7.20% | 2.62% | 8.69% | | 0.57 | |
| V Alpha 23 | 214 | 12 | 2.67% | 1.35% | 2.03% | | −0.48 | |
| V Alpha 23 | 217 | 13 | 0.47% | 0.44% | 0.56% | | 0.22 | |
| V Alpha 23 | 220 | 14 | 0.02% | 0.03% | | | | |
| V Alpha 23 | 223 | 15 | | | | | | |
| V Alpha 23 | 226 | 16 | | | | | | |
| V Alpha 23 | 229 | 17 | | | | | | |
| V Alpha 23 | 232 | 18 | | | | | | |
| V Alpha 24 | 172 | 0 | | | | | | |
| V Alpha 24 | 175 | 1 | | | | | | |
| V Alpha 24 | 178 | 2 | | | | 35.18% | | |
| V Alpha 24 | 181 | 3 | | | | | | |
| V Alpha 24 | 184 | 4 | 0.27% | 0.30% | | | | |
| V Alpha 24 | 187 | 5 | 1.62% | 1.28% | | | | |
| V Alpha 24 | 190 | 6 | 3.46% | 1.52% | 8.92% | | 3.60 | |
| V Alpha 24 | 193 | 7 | 8.78% | 3.46% | 11.80% | 30.19% | 0.87 | 6.19 |
| V Alpha 24 | 196 | 8 | 17.08% | 5.75% | 19.90% | 18.86% | 0.49 | 0.31 |
| V Alpha 24 | 199 | 9 | 24.78% | 5.35% | 23.49% | 15.78% | −0.24 | −1.68 |
| V Alpha 24 | 202 | 10 | 25.67% | 7.24% | 19.71% | | −0.82 | |
| V Alpha 24 | 205 | 11 | 12.11% | 6.53% | 10.41% | | −0.26 | |
| V Alpha 24 | 208 | 12 | 4.68% | 4.00% | 4.04% | | −0.16 | |
| V Alpha 24 | 211 | 13 | 1.44% | 1.22% | 1.73% | | 0.23 | |
| V Alpha 24 | 214 | 14 | 0.11% | 0.31% | | | | |
| V Alpha 24 | 217 | 15 | | | | | | |
| V Alpha 24 | 220 | 16 | | | | | | |
| V Alpha 24 | 223 | 17 | | | | | | |
| V Alpha 24 | 226 | 18 | | | | | | |
| V Alpha 25 | 270 | 0 | | | | | | |
| V Alpha 25 | 273 | 1 | | | | | | |
| V Alpha 25 | 276 | 2 | | | | | | |
| V Alpha 25 | 279 | 3 | | | 0.89% | | | |
| V Alpha 25 | 282 | 4 | | | 1.19% | | | |
| V Alpha 25 | 285 | 5 | 0.18% | 0.51% | 3.76% | | 6.96 | |
| V Alpha 25 | 288 | 6 | 5.08% | 6.43% | 0.80% | | −0.66 | |
| V Alpha 25 | 291 | 7 | 6.51% | 5.57% | 6.05% | | −0.08 | |
| V Alpha 25 | 294 | 8 | 10.38% | 6.61% | 7.50% | | −0.44 | |
| V Alpha 25 | 297 | 9 | 16.19% | 6.74% | 17.58% | | 0.21 | |
| V Alpha 25 | 300 | 10 | 20.94% | 5.78% | 16.20% | 28.25% | −0.82 | 1.27 |
| V Alpha 25 | 303 | 11 | 17.13% | 6.58% | 20.32% | | 0.48 | |
| V Alpha 25 | 306 | 12 | 10.55% | 6.58% | 12.52% | 40.29% | 0.30 | 4.52 |
| V Alpha 25 | 309 | 13 | 6.80% | 7.57% | 11.22% | 31.46% | 0.58 | 3.26 |
| V Alpha 25 | 312 | 14 | 4.14% | 5.20% | 1.98% | | −0.42 | |
| V Alpha 25 | 315 | 15 | 1.68% | 2.55% | | | | |
| V Alpha 25 | 318 | 16 | 0.48% | 1.17% | | | | |
| V Alpha 25 | 321 | 17 | | | | | | |
| V Alpha 25 | 324 | 18 | | | | | | |
| V Alpha 26 | 125 | 0 | | | | | | |
| V Alpha 26 | 128 | 1 | | | | | | |
| V Alpha 26 | 131 | 2 | | | | | | |
| V Alpha 26 | 134 | 3 | | | | | | |
| V Alpha 26 | 137 | 4 | 1.38% | 2.51% | | | | |
| V Alpha 26 | 140 | 5 | 2.73% | 2.77% | 2.33% | | −0.15 | |
| V Alpha 26 | 143 | 6 | 4.19% | 3.50% | 9.19% | | 1.43 | |
| V Alpha 26 | 146 | 7 | 12.45% | 5.19% | 17.81% | | 1.03 | |
| V Alpha 26 | 149 | 8 | 22.00% | 8.32% | 13.72% | | −0.99 | |
| V Alpha 26 | 152 | 9 | 21.93% | 4.09% | 26.36% | | 1.08 | |
| V Alpha 26 | 155 | 10 | 14.89% | 4.68% | 8.83% | 100.00% | −1.29 | 18.18 |
| V Alpha 26 | 158 | 11 | 9.84% | 4.95% | 11.60% | | 0.36 | |
| V Alpha 26 | 161 | 12 | 8.99% | 7.35% | 5.62% | | −0.46 | |
| V Alpha 26 | 164 | 13 | 1.38% | 1.76% | 1.74% | | 0.21 | |
| V Alpha 26 | 167 | 14 | 0.22% | 0.42% | 2.80% | | 6.12 | |
| V Alpha 26 | 170 | 15 | | | | | | |
| V Alpha 26 | 173 | 16 | | | | | | |
| V Alpha 26 | 176 | 17 | | | | | | |
| V Alpha 26 | 179 | 18 | | | | | | |
| V Alpha 27 | 161 | 0 | | | | | | |

TABLE IX-continued

Intrafamily Fragment Analysis of V Alpha Gene CDR3 Regions from a Patient with Primary Biliary Cirrhosis

| Families | Fragment Length (nt) | CDR3 Length (aa) | Control Mean | Control SD | Patient PBMC | Patient Liver | X/SD* PBMC | X/SD* Liver |
|---|---|---|---|---|---|---|---|---|
| V Alpha 27 | 164 | 1 | | | | | | |
| V Alpha 27 | 167 | 2 | | | | | | |
| V Alpha 27 | 170 | 3 | 0.33% | 0.46% | | | | |
| V Alpha 27 | 173 | 4 | 1.02% | 1.46% | 0.08% | | −0.64 | |
| V Alpha 27 | 176 | 5 | 6.03% | 8.71% | 2.68% | | −0.39 | |
| V Alpha 27 | 179 | 6 | 6.70% | 4.32% | 10.12% | | 0.79 | |
| V Alpha 27 | 182 | 7 | 14.02% | 5.36% | 16.03% | | 0.38 | |
| V Alpha 27 | 185 | 8 | 15.69% | 4.65% | 18.86% | | 0.68 | |
| V Alpha 27 | 188 | 9 | 20.54% | 6.24% | 20.98% | | 0.07 | |
| V Alpha 27 | 191 | 10 | 19.55% | 4.46% | 17.04% | 100.00% | −0.56 | 18.03 |
| V Alpha 27 | 194 | 11 | 9.01% | 4.64% | 8.62% | | −0.08 | |
| V Alpha 27 | 197 | 12 | 5.32% | 5.54% | 4.61% | | −0.13 | |
| V Alpha 27 | 200 | 13 | 1.15% | 1.95% | 0.98% | | −0.09 | |
| V Alpha 27 | 203 | 14 | 0.46% | 1.05% | | | | |
| V Alpha 27 | 206 | 15 | 0.19% | 0.53% | | | | |
| V Alpha 27 | 209 | 16 | | | | | | |
| V Alpha 27 | 212 | 17 | | | | | | |
| V Alpha 27 | 215 | 18 | | | | | | |
| V Alpha 28 | 332 | 0 | | | | | | |
| V Alpha 28 | 335 | 1 | 0.02% | 0.06% | | | | |
| V Alpha 28 | 338 | 2 | 0.12% | 0.34% | | | | |
| V Alpha 28 | 341 | 3 | 0.34% | 0.84% | | | | |
| V Alpha 28 | 344 | 4 | 0.66% | 1.50% | | | | |
| V Alpha 28 | 347 | 5 | 1.82% | 2.33% | | | | |
| V Alpha 28 | 350 | 6 | 3.71% | 5.15% | | | | |
| V Alpha 28 | 353 | 7 | 11.41% | 6.23% | 10.14% | | −0.20 | |
| V Alpha 28 | 356 | 8 | 14.21% | 1.67% | 8.64% | 34.86% | −3.35 | 12.39 |
| V Alpha 28 | 359 | 9 | 23.09% | 4.96% | 29.80% | | 1.35 | |
| V Alpha 28 | 362 | 10 | 19.11% | 4.17% | 29.41% | | 2.47 | |
| V Alpha 28 | 365 | 11 | 15.23% | 4.71% | 19.76% | 44.84% | 0.96 | 6.26 |
| V Alpha 28 | 368 | 12 | 6.97% | 3.52% | | | | |
| V Alpha 28 | 371 | 13 | 2.57% | 1.66% | 2.26% | 20.30% | −0.19 | 10.68 |
| V Alpha 28 | 374 | 14 | 0.61% | 0.60% | | | | |
| V Alpha 28 | 377 | 15 | 0.12% | 0.27% | | | | |
| V Alpha 28 | 380 | 16 | | | | | | |
| V Alpha 28 | 383 | 17 | | | | | | |
| V Alpha 28 | 386 | 18 | | | | | | |
| V Alpha 29 | 214 | 0 | 7.81% | 17.18% | | | | |
| V Alpha 29 | 217 | 1 | 4.10% | 7.09% | | | | |
| V Alpha 29 | 220 | 2 | 12.96% | 13.20% | | | | |
| V Alpha 29 | 223 | 3 | 12.98% | 13.14% | | | | |
| V Alpha 29 | 226 | 4 | 3.82% | 4.39% | | | | |
| V Alpha 29 | 229 | 5 | 2.67% | 5.31% | 81.74% | | 14.90 | |
| V Alpha 29 | 232 | 6 | 10.17% | 16.33% | | | | |
| V Alpha 29 | 235 | 7 | 2.19% | 6.19% | | | | |
| V Alpha 29 | 238 | 8 | 15.30% | 19.74% | | | | |
| V Alpha 29 | 241 | 9 | 8.09% | 13.15% | 18.26% | | 0.77 | |
| V Alpha 29 | 244 | 10 | 8.83% | 17.10% | | | | |
| V Alpha 29 | 247 | 11 | 0.95% | 1.08% | | | | |
| V Alpha 29 | 250 | 12 | 8.54% | 16.54% | | | | |
| V Alpha 29 | 253 | 13 | 1.30% | 2.27% | | | | |
| V Alpha 29 | 256 | 14 | 0.30% | 0.85% | | | | |
| V Alpha 29 | 259 | 15 | | | | | | |
| V Alpha 29 | 262 | 16 | | | | | | |
| V Alpha 29 | 265 | 17 | | | | | | |
| V Alpha 29 | 268 | 18 | | | | | | |

*X/SD = (% of patient peak area - % of control peak area)/control SD

TABLE X

Intrafamily Fragment Analysis of V Beta Gene CDR3 Regions from a Patient with Primary Biliary Cirrhosis

| Families | Fragment Length (nt) | CDR3 Length (aa) | Control Mean | Control SD | Patient PBMC | Patient Liver | X/SD* PBMC | X/SD* Liver |
|---|---|---|---|---|---|---|---|---|
| V Beta 1 | 171 | 0 | | | | | | |
| V Beta 1 | 174 | 1 | | | | | | |
| V Beta 1 | 177 | 2 | | | | | | |
| V Beta 1 | 180 | 3 | 0.1% | | | 3.2% | | |

TABLE X-continued

Intrafamily Fragment Analysis of V Beta Gene CDR3 Regions
from a Patient with Primary Biliary Cirrhosis

| Families | Fragment Length (nt) | CDR3 Length (aa) | Control Mean | Control SD | Patient PBMC | Patient Liver | X/SD* PBMC | X/SD* Liver |
|---|---|---|---|---|---|---|---|---|
| V Beta 1 | 183 | 4 | 0.1% | 0.1% | | 4.7% | −0.49 | 33.47 |
| V Beta 1 | 186 | 5 | 0.5% | 0.6% | | | | |
| V Beta 1 | 189 | 6 | 2.8% | 1.4% | 6.7% | 29.6% | 2.71 | 18.64 |
| V Beta 1 | 192 | 7 | 10.2% | 8.7% | 5.5% | 3.0% | −0.54 | −0.83 |
| V Beta 1 | 195 | 8 | 14.3% | 3.6% | 17.0% | | 0.74 | |
| V Beta 1 | 198 | 9 | 19.6% | 4.1% | 22.6% | 24.2% | 0.72 | 1.11 |
| V Beta 1 | 201 | 10 | 20.5% | 7.2% | 32.3% | 24.0% | 1.64 | 0.48 |
| V Beta 1 | 204 | 11 | 14.9% | 4.4% | 7.9% | | −1.60 | |
| V Beta 1 | 207 | 12 | 6.3% | 2.7% | 4.4% | 5.0% | −0.70 | −0.48 |
| V Beta 1 | 210 | 13 | 3.1% | 0.7% | 1.7% | | −2.19 | |
| V Beta 1 | 213 | 14 | 2.1% | 1.1% | 0.4% | | −1.59 | |
| V Beta 1 | 216 | 15 | 1.6% | 0.7% | 0.6% | | −1.41 | |
| V Beta 1 | 219 | 16 | 1.5% | 1.1% | 1.0% | | −0.50 | |
| V.Beta 1 | 222 | 17 | 1.2% | 1.3% | | | | |
| V Beta 1 | 225 | 18 | 0.9% | 1.5% | | | | |
| V Beta 1 | 228 | 19 | 0.3% | | | | | |
| V Beta 1 | 231 | 20 | | | | | | |
| V Beta 1 | 234 | 21 | | | | | | |
| V Beta 2 | 173 | 0 | | | | | | |
| V Bete 2 | 176 | 1 | | | | | | |
| V Beta 2 | 179 | 2 | | | 1.2% | | | |
| V Beta 2 | 182 | 3 | | | 1.8% | | | |
| V Beta 2 | 185 | 4 | 0.6% | 0.5% | 3.3% | | 5.18 | |
| V Beta 2 | 188 | 5 | 2.6% | 1.7% | 5.5% | | 1.73 | |
| V Beta 2 | 191 | 6 | 7.2% | 2.5% | 11.1% | 33.3% | 1.58 | 10.57 |
| V Beta 2 | 194 | 7 | 13.6% | 4.2% | 18.7% | 10.6% | 1.21 | −0.72 |
| V Beta 2 | 197 | 8 | 20.8% | 4.6% | 26.0% | 16.9% | 1.13 | −0.83 |
| V Beta 2 | 200 | 9 | 21.4% | 2.9% | 19.0% | 30.1% | −0.84 | 3.05 |
| V Beta 2 | 203 | 10 | 14.8% | 3.7% | 5.9% | 9.1% | −2.39 | −1.53 |
| V Beta 2 | 206 | 11 | 8.4% | 2.6% | 7.5% | | −0.36 | |
| V Beta 2 | 209 | 12 | 4.5% | 3.0% | | | | |
| V Beta 2 | 212 | 13 | 1.8% | 0.8% | | | | |
| V Beta 2 | 215 | 14 | 1.7% | 0.5% | | | | |
| V Beta 2 | 218 | 15 | 1.5% | 0.6% | | | | |
| V Beta 2 | 221 | 16 | 0.7% | 0.6% | | | | |
| V Bete 2 | 224 | 17 | 0.3% | 0.3% | | | | |
| V Bete 2 | 227 | 18 | 0.1% | 0.2% | | | | |
| V Beta 2 | 230 | 19 | | | | | | |
| V Beta 2 | 233 | 20 | | | | | | |
| V Beta 2 | 236 | 21 | | | | | | |
| V Beta 3 | 171 | 0 | | | 0.6% | | 8.06 | |
| V Beta 3 | 174 | 1 | | | 1.7% | | 2.31 | |
| V Beta 3 | 177 | 2 | 0.9% | 0.9% | 3.8% | | 3.15 | |
| V Beta 3 | 180 | 3 | 1.4% | 1.1% | 5.1% | | 3.25 | |
| V Beta 3 | 183 | 4 | 1.9% | 1.6% | 7.4% | | 3.42 | |
| V Beta 3 | 186 | 5 | 4.7% | 3.5% | 8.0% | | 0.93 | |
| V Beta 3 | 189 | 6 | 6.9% | 1.8% | 6.4% | | −0.23 | |
| V Beta 3 | 192 | 7 | 10.4% | 2.2% | 8.5% | | −0.86 | |
| V Beta 3 | 195 | 8 | 13.4% | 2.1% | 10.8% | | −1.24 | |
| V Beta 3 | 198 | 9 | 17.9% | 2.9% | 12.6% | | −1.85 | |
| V Beta 3 | 201 | 10 | 16.0% | 3.3% | 17.8% | | 0.56 | |
| V Beta 3 | 204 | 11 | 9.7% | 2.8% | 10.9% | | 0.43 | |
| V Beta 3 | 207 | 12 | 8.2% | 5.7% | 4.0% | | −0.74 | |
| V Beta 3 | 210 | 13 | 2.3% | 0.9% | 2.2% | | −0.19 | |
| V Beta 3 | 213 | 14 | 2.0% | 0.6% | 0.2% | | −2.95 | |
| V Beta 3 | 216 | 15 | 1.7% | 0.4% | | | | |
| V Beta 3 | 219 | 16 | 0.9% | 0.7% | | | | |
| V Beta 3 | 222 | 17 | 0.5% | 0.4% | | | | |
| V Beta.3 | 225 | 18 | 0.5% | 0.4% | | | | |
| V Beta 3 | 228 | 19 | 0.2% | 0.3% | | | | |
| V Beta 3 | 231 | 20 | 0.1% | 0.2% | | | | |
| V Beta 3 | 234 | 21 | 0.1% | 0.1% | | | | |
| V Beta 4 | 207 | 0 | | | | | | |
| V Beta 4 | 210 | 1 | | | | | | |
| V Beta 4 | 213 | 2 | 0.1% | 0.1% | | | | |
| V Beta 4 | 216 | 3 | 0.4% | 0.3% | | | | |
| V Beta 4 | 219 | 4 | 1.0% | 0.6% | | | | |
| V Beta 4 | 222 | 5 | 3.3% | 0.7% | | | | |
| V Beta 4 | 225 | 6 | 9.5% | 1.6% | 10.3% | 0.8% | 0.51 | −5.46 |
| V Beta 4 | 228 | 7 | 16.2% | 1.7% | 10.6% | 33.1% | −3.30 | 9.90 |
| V Beta 4 | 231 | 8 | 18.2% | 2.3% | 29.7% | 12.8% | 4.87 | −2.29 |
| V Beta 4 | 234 | 9 | 17.6% | 1.7% | 24.4% | 1.6% | 4.02 | −9.50 |
| V Beta 4 | 237 | 10 | 12.6% | 1.4% | 9.6% | 15.9% | −2.15 | 2.35 |

TABLE X-continued

Intrafamily Fragment Analysis of V Beta Gene CDR3 Regions from a Patient with Primary Biliary Cirrhosis

| Families | Fragment Length (nt) | CDR3 Length (aa) | Control Mean | Control SD | Patient PBMC | Patient Liver | X/SD* PBMC | X/SD* Liver |
|---|---|---|---|---|---|---|---|---|
| V Beta 4 | 240 | 11 | 6.7% | 1.3% | 5.4% | 35.7% | −0.94 | 21.52 |
| V Beta 4 | 243 | 12 | 3.5% | 0.7% | 4.5% | | 1.42 | |
| V Beta 4 | 246 | 13 | 3.2% | 0.7% | 2.2% | | −1.45 | |
| V Beta 4 | 249 | 14 | 2.8% | 1.0% | 1.8% | | −0.99 | |
| V Beta 4 | 252 | 15 | 2.3% | 0.9% | 1.3% | | −1.06 | |
| V Beta 4 | 255 | 16 | 1.3% | 0.7% | 0.2% | | −1.55 | |
| V Beta 4 | 256 | 17 | 0.6% | 0.4% | | | | |
| V Beta 4 | 261 | 18 | 0.2% | 0.4% | | | | |
| V Beta 4 | 264 | 19 | 0.3% | 0.6% | | | | |
| V Beta 4 | 267 | 20 | | | | | | |
| V Beta 4 | 270 | 21 | | | | | | |
| V Beta 5.1 | 223 | 0 | | | | | | |
| V Beta 5.1 | 226 | 1 | | | | | | |
| V Beta 5.1 | 229 | 2 | 0.4% | 0.5% | | | | |
| V Beta 5.1 | 232 | 3 | 0.5% | 0.5% | | | | |
| V Beta 5.1 | 235 | 4 | 0.6% | 0.5% | | | | |
| V Beta 5.1 | 238 | 5 | 0.7% | 0.6% | | 1.0% | | 0.57 |
| V Beta 5.1 | 241 | 6 | 2.2% | 1.2% | 9.1% | 8.3% | 5.96 | 5.30 |
| V Beta 5.1 | 244 | 7 | 5.5% | 3.2% | | 0.2% | | −1.67 |
| V Beta 5.1 | 247 | 8 | 14.1% | 7.2% | 14.6% | 1.0% | 0.07 | −1.83 |
| V Beta 5.1 | 250 | 9 | 19.7% | 4.4% | 33.0% | 10.1% | 3.00 | −2.19 |
| V Beta 5.1 | 253 | 10 | 21.4% | 4.2% | 22.7% | 37.1% | 0.29 | 3.77 |
| V Beta 5.1 | 256 | 11 | 14.9% | 4.8% | 12.0% | 42.2% | −0.59 | 5.69 |
| V Beta 5.1 | 259 | 12 | 8.3% | 4.7% | 5.2% | | −0.66 | |
| V Beta 5.1 | 262 | 13 | 4.2% | 2.9% | 1.2% | | −1.03 | |
| V Beta 5.1 | 265 | 14 | 2.5% | 0.4% | | | | |
| V Beta 5.1 | 268 | 15 | 2.0% | 0.4% | 1.2% | | −1.80 | |
| V Beta 5.1 | 271 | 16 | 1.8% | 0.5% | 0.7% | | −1.91 | |
| V Beta 5.1 | 274 | 17 | 1.0% | 0.4% | 0.3% | | −1.63 | |
| V Beta 5.1 | 277 | 18 | 0.2% | 0.3% | | | | |
| V Beta 5.1 | 280 | 19 | | | | | | |
| V Beta 5.1 | 283 | 20 | | | | | | |
| V Beta 5.1 | 286 | 21 | | | | | | |
| V Beta 5.2 | 162 | 0 | | | | | | |
| V Beta 5.2 | 165 | 1 | | | | | | |
| V Beta 5.2 | 168 | 2 | | | | | | |
| V Beta 5.2 | 171 | 3 | 0.1% | 0.2% | | | | |
| V Beta 5.2 | 174 | 4 | 0.3% | 0.4% | | 5.9% | | 13.00 |
| V Beta 5.2 | 177 | 5 | 1.6% | 1.4% | 1.8% | 10.8% | 0.09 | 6.49 |
| V Beta 5.2 | 180 | 6 | 4.5% | 2.6% | 9.0% | 3.7% | 1.75 | −0.31 |
| V Beta 5.2 | 183 | 7 | 10.7% | 4.3% | 14.8% | 9.3% | 0.98 | −0.33 |
| V Beta 5.2 | 186 | 8 | 16.7% | 4.1% | 26.8% | 27.7% | 2.46 | 2.68 |
| V Beta 5.2 | 189 | 9 | 20.5% | 1.5% | 8.2% | 4.5% | −8.49 | −11.04 |
| V Beta 5.2 | 192 | 10 | 19.7% | 6.4% | 29.1% | 29.2% | 1.47 | 1.49 |
| V Beta 5.2 | 195 | 11 | 11.0% | 4.1% | 7.3% | | −0.90 | |
| V Beta 5.2 | 198 | 12 | 6.0% | 2.0% | 3.1% | | −1.43 | |
| V Beta 5.2 | 201 | 13 | 3.1% | 1.1% | | | | |
| V Beta 5.2 | 204 | 14 | 2.0% | 0.6% | | | | |
| V Beta 5.2 | 207 | 15 | 1.9% | 0.6% | | | | |
| V Beta 5.2 | 210 | 16 | 1.4% | 0.8% | | | | |
| V Beta 5.2 | 213 | 17 | 0.5% | 0.3% | | | | |
| V Beta 5.2 | 216 | 18 | 0.1% | 0.1% | | | | |
| V Beta 5.2 | 219 | 19 | | | | | | |
| V Bete 5.2 | 222 | 20 | | | | | | |
| V Beta 5.2 | 225 | 21 | | | | | | |
| V Beta 6 | 165 | 0 | | | | | | |
| V Beta 6 | 168 | 1 | | | | | | |
| V Beta 6 | 171 | 2 | | | | | | |
| V Beta 6 | 174 | 3 | | | | | | |
| V Beta 6 | 177 | 4 | | | 1.7% | 1.1% | | |
| V Beta 6 | 180 | 5 | 1.0% | 1.1% | 3.8% | 2.1% | 2.59 | 0.99 |
| V Beta 6 | 183 | 6 | 2.6% | 1.9% | 8.3% | 7.9% | 2.98 | 2.78 |
| V Beta 6 | 186 | 7 | 8.5% | 5.7% | 20.8% | 18.4% | 2.16 | 1.74 |
| V Beta 6 | 189 | 8 | 13.7% | 5.7% | 28.7% | 19.7% | 2.64 | 1.04 |
| V Beta 6 | 192 | 9 | 20.6% | 6.2% | 24.9% | 28.3% | 0.69 | 1.24 |
| V Beta 6 | 195 | 10 | 17.1% | 4.6% | 7.2% | 12.5% | −2.15 | −1.00 |
| V Beta 6 | 198 | 11 | 12.8% | 3.8% | 3.1% | 5.9% | −2.56 | −1.81 |
| V Beta 6 | 201 | 12 | 11.0% | 9.4% | 1.6% | 2.0% | −1.01 | −0.96 |
| V Beta 6 | 204 | 13 | 5.2% | 3.3% | | 0.7% | | −1.37 |
| V Bete 6 | 207 | 14 | 3.2% | 2.4% | | 0.4% | | −1.17 |
| V Beta 6 | 210 | 15 | 2.0% | 1.2% | | 1.0% | | −0.86 |
| V Beta 6 | 213 | 16 | 1.1% | 0.6% | | | | |
| V Beta 6 | 216 | 17 | 0.6% | 0.5% | | | | |

TABLE X-continued

Intrafamily Fragment Analysis of V Beta Gene CDR3 Regions from a Patient with Primary Biliary Cirrhosis

| Families | Fragment Length (nt) | CDR3 Length (aa) | Control Mean | Control SD | Patient PBMC | Patient Liver | X/SD* PBMC | X/SD* Liver |
|---|---|---|---|---|---|---|---|---|
| V Beta 6 | 219 | 18 | 0.3% | 0.6% | | | | |
| V Beta 6 | 222 | 19 | 0.1% | | | | | |
| V Beta 6 | 225 | 20 | | | | | | |
| V Beta 6 | 228 | 21 | | | | | | |
| V Beta 7 | 171 | 0 | | | | | | |
| V Beta 7 | 174 | 1 | 0.1% | 0.1% | | | | |
| V Beta 7 | 177 | 2 | 0.1% | 0.2% | | | | |
| V Beta 7 | 180 | 3 | 0.1% | 0.2% | | | | |
| V Beta 7 | 183 | 4 | 0.1% | 0.1% | | | | |
| V Beta 7 | 186 | 5 | 0.2% | 0.3% | | | | |
| V Beta 7 | 189 | 6 | 1.7% | 1.3% | 6.0% | | 3.26 | |
| V Beta 7 | 192 | 7 | 4.2% | 3.1% | 15.0% | | 3.51 | |
| V Beta 7 | 195 | 8 | 11.3% | 3.5% | 10.0% | 16.9% | −0.36 | 1.62 |
| V Beta 7 | 198 | 9 | 17.2% | 5.1% | 33.7% | 12.2% | 3.23 | −0.99 |
| V Beta 7 | 201 | 10 | 23.0% | 3.9% | 14.0% | 15.8% | −2.30 | −1.83 |
| V Beta 7 | 204 | 11 | 18.2% | 4.3% | 10.8% | 5.7% | −1.73 | −2.89 |
| V Beta 7 | 207 | 12 | 12.6% | 6.9% | 4.2% | | −1.22 | |
| V Beta 7 | 210 | 13 | 5.3% | 2.5% | 5.0% | 32.7% | −0.13 | 10.97 |
| V Beta 7 | 213 | 14 | 2.3% | 1.3% | 1.4% | 13.3% | −0.69 | 8.25 |
| V Beta 7 | 216 | 15 | 1.4% | 0.7% | | 2.9% | | 2.11 |
| V Beta 7 | 219 | 16 | 1.2% | 0.5% | | 0.4% | | −1.65 |
| V Beta 7 | 222 | 17 | 0.7% | 0.4% | | | | |
| V Beta 7 | 225 | 18 | 0.3% | 0.4% | | | | |
| V Beta 7 | 228 | 19 | 0.1% | 0.1% | | | | |
| V Beta 7 | 231 | 20 | | | | | | |
| V Beta 7 | 234 | 21 | | | | | | |
| V Beta 8 | 231 | 0 | | | 0.9% | | | |
| V Beta 8 | 234 | 1 | | | 2.2% | 0.4% | | |
| V Beta 8 | 237 | 2 | 0.1% | 0.1% | 1.8% | 0.5% | 13.42 | 3.11 |
| V Beta 8 | 240 | 3 | 0.2% | 0.3% | 2.8% | 0.6% | 10.05 | 1.49 |
| V Beta 8 | 243 | 4 | 0.4% | 0.5% | 3.2% | 3.5% | 5.82 | 6.41 |
| V Beta 8 | 246 | 5 | 0.7 | 0.4% | | 2.1% | | 3.61 |
| V Beta 8 | 249 | 6 | 5.2% | 2.2% | 14.7% | 3.1% | 4.29 | −0.91 |
| V Beta 8 | 252 | 7 | 8.4% | 1.5% | 7.7% | 13.2% | −0.48 | 3.16 |
| V Beta 8 | 255 | 8 | 15.9% | 1.7% | 17.0% | | 0.60 | |
| V Beta 8 | 258 | 9 | 20.0% | 4.9% | 12.5% | 69.8% | −1.54 | 10.12 |
| V Beta 8 | 261 | 10 | 18.8% | 2.4% | 16.7% | | −0.87 | |
| V Beta 8 | 264 | 11 | 11.8% | 1.4% | 13.1% | 0.6% | 0.92 | −7.92 |
| V Beta 8 | 267 | 12 | 6.8% | 1.7% | 7.4% | | 0.36 | |
| V Beta 8 | 270 | 13 | 3.3% | 1.2% | | | | |
| V Beta 8 | 273 | 14 | 2.8% | 1.7% | | | | |
| V Beta 8 | 276 | 15 | 2.3% | 0.6% | | 5.3% | | 4.53 |
| V Beta 8 | 279 | 16 | 1.9% | 0.5% | | | | |
| V Beta 8 | 282 | 17 | 0.9% | 0.5% | | | | |
| V Beta 8 | 285 | 18 | 0.4% | 0.3% | | | | |
| V Beta 8 | 288 | 19 | 0.1% | 0.1% | | | | |
| V Beta 8 | 291 | 20 | | | | | | |
| V Beta 8 | 294 | 21 | | | | | | |
| V Beta 9 | 171 | 0 | | | | | | |
| V Beta 9 | 174 | 1 | | | | | | |
| V Beta 9 | 177 | 2 | | | | 0.9% | | |
| V Beta 9 | 180 | 3 | | | 0.3% | 1.7% | | |
| V Beta 9 | 183 | 4 | 0.3% | 0.8% | 0.7% | 3.0% | 0.50 | 3.21 |
| V Beta 9 | 186 | 5 | 1.7% | 2.6% | 2.6% | 18.6% | 0.32 | 6.48 |
| V Beta 9 | 189 | 6 | 5.7% | 4.3% | 18.2% | 12.7% | 2.92 | 1.64 |
| V Beta 9 | 192 | 7 | 10.8% | 5.3% | 13.0% | 11.1% | 0.42 | 0.07 |
| V Beta 9 | 195 | 8 | 15.5% | 5.0% | 27.1% | 1.7% | 2.33 | −2.77 |
| V Beta 9 | 198 | 9 | 20.5% | 3.5% | 22.4% | 18.1% | 0.54 | −0.68 |
| V Beta 9 | 201 | 10 | 18.9% | 5.9% | 8.5% | 12.9% | −1.76 | −1.02 |
| V Beta 9 | 204 | 11 | 14.2% | 6.9% | 5.2% | 19.2% | −1.28 | 0.73 |
| V Beta 9 | 207 | 12 | 5.5% | 2.9% | 1.9% | | −1.28 | |
| V Beta 9 | 210 | 13 | 2.9% | 2.0% | | | | |
| V Beta 9 | 213 | 14 | 1.5% | 0.9% | | | | |
| V Beta 9 | 216 | 15 | 1.2% | 0.8% | | | | |
| V Beta 9 | 219 | 16 | 0.8% | 0.6% | | | | |
| V Beta 9 | 222 | 17 | 0.5% | 0.2% | | | | |
| V Beta 9 | 225 | 18 | | | | | | |
| V Beta 9 | 228 | 19 | | | | | | |
| V Beta 9 | 231 | 20 | | | | | | |
| V Beta 9 | 234 | 21 | | | | | | |
| V Beta 10 | 163 | 0 | | | | | | |
| V Beta 10 | 166 | 1 | | | | 4.3% | | |
| V Beta 10 | 169 | 2 | | | | 6.8% | | |

TABLE X-continued

Intrafamily Fragment Analysis of V Beta Gene CDR3 Regions from a Patient with Primary Biliary Cirrhosis

| Families | Fragment Length (nt) | CDR3 Length (aa) | Control Mean | Control SD | Patient PBMC | Patient Liver | X/SD* PBMC | X/SD* Liver |
|---|---|---|---|---|---|---|---|---|
| V Beta 10 | 172 | 3 | 0.1% | | | 5.3% | | |
| V Beta 10 | 175 | 4 | 0.4% | 0.6% | | 4.7% | | 7.16 |
| V Beta 10 | 178 | 5 | 0.9% | 1.0% | | | | |
| V Beta 10 | 181 | 6 | 1.9% | 1.6% | 3.9% | | 1.28 | |
| V Beta 10 | 184 | 7 | 4.1% | 2.3% | 9.0% | | 2.11 | |
| V Beta 10 | 187 | 8 | 7.6% | 3.5% | 4.2% | 35.8% | −0.97 | 8.17 |
| V Beta 10 | 190 | 9 | 11.4% | 5.7% | 10.3% | 7.7% | −0.20 | −0.65 |
| V Beta 10 | 193 | 10 | 20.1% | 8.6% | 33.1% | | 1.52 | |
| V Beta 10 | 196 | 11 | 14.6% | 4.2% | 13.4% | | −0.29 | |
| V Beta 10 | 199 | 12 | 12.8% | 5.7% | 7.3% | | −0.99 | |
| V Beta 10 | 202 | 13 | 9.3% | 4.7% | 9.0% | | −0.05 | |
| V Beta 10 | 205 | 14 | 7.0% | 6.0% | 5.4% | 2.7% | −0.27 | −0.72 |
| V Beta 10 | 208 | 15 | 4.8% | 4.0% | 2.5% | | −0.58 | |
| V Beta 10 | 211 | 16 | 2.4% | 2.2% | 1.4% | | −0.45 | |
| V Beta 10 | 214 | 17 | 1.4% | 1.2% | 0.5% | | −0.70 | |
| V Beta 10 | 217 | 18 | 0.9% | 1.8% | | | | |
| V Beta 10 | 220 | 19 | | | | | | |
| V Beta 10 | 223 | 20 | | | | | | |
| V Beta 10 | 226 | 21 | | | | | | |
| V Beta 11 | 177 | 0 | | | | 0.9% | | |
| V Beta 11 | 180 | 1 | 0.1% | 0.2% | | | | |
| V Beta 11 | 183 | 2 | 0.2% | 0.4% | | 0.3% | | 0.04 |
| V Beta 11 | 186 | 3 | 0.4% | 0.5% | | 2.9% | | 4.76 |
| V Beta 11 | 189 | 4 | 0.7% | 0.8% | | 3.9% | | 3.96 |
| V Beta 11 | 192 | 5 | 3.5% | 3.9% | | 0.4% | | −0.79 |
| V Beta 11 | 195 | 6 | 6.2% | 2.0% | | 0.3% | | −2.86 |
| V Beta 11 | 198 | 7 | 11.0% | 4.6% | 20.1% | | 1.99 | |
| V Beta 11 | 201 | 8 | 14.5% | 4.4% | 18.3% | | 0.85 | |
| V Beta 11 | 204 | 9 | 19.0% | 3.3% | 51.0% | 6.9% | 9.82 | −3.72 |
| V Beta 11 | 207 | 10 | 19.8% | 8.4% | | 27.2% | | 0.89 |
| V Beta 11 | 210 | 11 | 13.1% | 8.1% | 5.6% | 31.0% | −0.93 | 2.21 |
| V Beta 11 | 213 | 12 | 5.9% | 3.8% | 5.0% | | −0.22 | |
| V Beta 11 | 216 | 13 | 2.5% | 1.6% | | 0.3% | −1.60 | −1.40 |
| V Beta 11 | 219 | 14 | 1.1% | 1.4% | | | | |
| V Beta 11 | 222 | 15 | 0.9% | 0.7% | | | | |
| V Beta 11 | 225 | 16 | 0.7% | 0.8% | | | | |
| V Beta 11 | 228 | 17 | 0.2% | 0.4% | | | | |
| V Beta 11 | 231 | 18 | 0.1% | | | | | |
| V Beta 11 | 234 | 19 | | | | | | |
| V Beta 11 | 237 | 20 | | | | | | |
| V Beta 11 | 240 | 21 | | | | | | |
| V Beta 12 | 198 | 0 | | | | | | |
| V Beta 12 | 201 | 1 | | | | | | |
| V Beta 12 | 204 | 2 | | | | | | |
| V Beta 12 | 207 | 3 | 0.1% | 0.1% | | | | |
| V Beta 12 | 210 | 4 | 0.1% | 0.2% | 7.0% | | 32.23 | |
| V Beta 12 | 213 | 5 | 1.6% | 1.3% | 0.7% | | −0.69 | |
| V Beta 12 | 216 | 6 | 4.3% | 2.8% | 9.1% | | 1.71 | |
| V Beta 12 | 219 | 7 | 10.2% | 4.7% | 14.9% | | 0.99 | |
| V Beta 12 | 222 | 8 | 18.1% | 1.6% | 11.6% | 2.6% | −4.08 | −9.67 |
| V Beta 12 | 225 | 9 | 19.4% | 1.8% | 26.2% | 30.3% | 3.73 | 5.94 |
| V Beta 12 | 228 | 10 | 18.8% | 2.9% | 27.1% | 37.1% | 2.88 | 6.40 |
| V Beta 12 | 231 | 11 | 11.6% | 4.0% | 3.5% | 29.9% | −2.04 | 4.62 |
| V Beta 12 | 234 | 12 | 6.0% | 2.0% | | | | |
| V Beta 12 | 237 | 13 | 2.9% | 1.0% | | | | |
| V Beta 12 | 240 | 14 | 2.5% | 0.8% | | | | |
| V Beta 12 | 243 | 15 | 1.9% | 0.4% | | | | |
| V Beta 12 | 246 | 16 | 1.5% | 0.6% | | | | |
| V Beta 12 | 249 | 17 | 0.6% | 0.5% | | | | |
| V Beta 12 | 252 | 18 | 0.2% | 0.3% | | | | |
| V Beta 12 | 255 | 19 | | | | | | |
| V Beta 12 | 258 | 20 | | | | | | |
| V Beta 12 | 261 | 21 | | | | | | |
| V Beta 13.1 | 198 | 0 | | | | | | |
| V Beta 13.1 | 201 | 1 | | | | | | |
| V Beta 13.1 | 204 | 2 | | | | | | |
| V Beta 13.1 | 207 | 3 | | | | | | |
| V Beta 13.1 | 210 | 4 | 0.1% | 0.2% | | 0.6% | | 3.23 |
| V Beta 13.1 | 213 | 5 | 1.5% | 1.5% | | 1.1% | | −0.29 |
| V Beta 13.1 | 216 | 6 | 3.9% | 2.7% | 8.7% | 0.9% | 1.78 | −1.13 |
| V Beta 13.1 | 219 | 7 | 10.1% | 5.9% | 29.6% | 5.7% | 3.32 | −0.74 |
| V Beta 13.1 | 222 | 8 | 18.3% | 3.1% | 15.4% | 28.9% | −0.95 | 3.41 |
| V Beta 13.1 | 225 | 9 | 21.4% | 2.4% | 19.8% | 35.3% | −0.66 | 5.82 |

TABLE X-continued

Intrafamily Fragment Analysis of V Beta Gene CDR3 Regions
from a Patient with Primary Biliary Cirrhosis

| Families | Fragment Length (nt) | CDR3 Length (aa) | Control Mean | Control SD | Patient PBMC | Patient Liver | X/SD* PBMC | X/SD* Liver |
|---|---|---|---|---|---|---|---|---|
| V Beta 13.1 | 228 | 10 | 21.1% | 5.9% | 13.3% | 14.9% | −1.32 | −1.03 |
| V Beta 13.1 | 231 | 11 | 11.4% | 4.5% | 5.2% | 7.8% | −1.37 | −0.79 |
| V Beta 13.1 | 234 | 12 | 4.6% | 2.0% | | 4.8% | | 0.10 |
| V Beta 13.1 | 237 | 13 | 2.6% | 1.3% | 5.4% | | 2.17 | |
| V Beta 13.1 | 240 | 14 | 2.0% | 1.0% | 2.2% | | 0.23 | |
| V Beta 13.1 | 243 | 15 | 1.6% | 0.8% | 0.4% | | −1.41 | |
| V Beta 13.1 | 246 | 16 | 1.2% | 0.5% | | | | |
| V Beta 13.1 | 249 | 17 | 0.3% | 0.3% | | | | |
| V Beta 13.1 | 252 | 18 | | | | | | |
| V Beta 13.1 | 255 | 19 | | | | | | |
| V Beta 13.1 | 258 | 20 | | | | | | |
| V Beta 13.1 | 261 | 21 | | | | | | |
| V Beta 13.2 | 216 | 0 | | | | | | |
| V Beta 13.2 | 219 | 1 | | | | | | |
| V Beta 13.2 | 222 | 2 | 0.1% | | | | | |
| V Beta 13.2 | 225 | 3 | 0.1% | 0.2% | | | | |
| V Beta 13.2 | 228 | 4 | 0.6% | 0.7% | | | | |
| V Beta 13.2 | 231 | 5 | 0.4% | 0.5% | | 0.5% | | 0.12 |
| V Beta 13.2 | 234 | 6 | 4.1% | 0.5% | | 1.1% | | −5.49 |
| V Beta 13.2 | 237 | 7 | 7.3% | 1.2% | 3.9% | 2.5% | −2.92 | −4.12 |
| V Beta 13.2 | 240 | 8 | 14.4% | 1.7% | 15.7% | 37.2% | 0.77 | 13.63 |
| V Beta 13.2 | 243 | 9 | 18.3% | 2.2% | 20.0% | | | 0.78 |
| V Beta 13.2 | 246 | 10 | 21.3% | 3.2% | 24.6% | 36.9% | 1.05 | 4.87 |
| V Beta 13.2 | 249 | 11 | 13.4% | 1.6% | 25.1% | | 7.40 | |
| V Beta 13.2 | 252 | 12 | 7.5% | 1.0% | 2.6% | 16.2% | −4.99 | 8.64 |
| V Beta 13.2 | 255 | 13 | 4.6% | 1.4% | 4.9% | 3.7% | 0.20 | −0.68 |
| V Beta 13.2 | 258 | 14 | 2.6% | 0.7% | 3.2% | 2.0% | 0.96 | −0.84 |
| V Beta 13.2 | 261 | 15 | 2.1% | 0.7% | | | | |
| V Beta 13.2 | 264 | 16 | 1.9% | 0.2% | | | | |
| V Beta 13.2 | 267 | 17 | 0.9% | 0.5% | | | | |
| V Beta 13.2 | 270 | 18 | 0.4% | 0.3% | | | | |
| V Beta 13.2 | 273 | 19 | 0.1% | 0.1% | | | | |
| V Beta 13.2 | 276 | 20 | | | | | | |
| V Beta 13.2 | 279 | 21 | | | | | | |
| V Beta 14 | 171 | 0 | | | | 2.5% | | |
| V Beta 14 | 174 | 1 | 0.1% | | | 3.7% | | |
| V Beta 14 | 177 | 2 | 0.1% | | | | | |
| V Beta 14 | 180 | 3 | 0.2% | 0.5% | | 3.5% | | 7.08 |
| V Beta 14 | 183 | 4 | 0.5% | 0.6% | | 0.5% | | −0.05 |
| V Beta 14 | 186 | 5 | 2.0% | 1.1% | | | | |
| V Beta 14 | 189 | 6 | 4.7% | 2.1% | 4.7% | | 0.02 | |
| V Beta 14 | 192 | 7 | 12.8% | 6.1% | 26.1% | 13.0% | 2.17 | 0.03 |
| V Beta 14 | 195 | 8 | 18.2% | 4.2% | 23.1% | | 1.15 | |
| V Beta 14 | 198 | 9 | 20.2% | 2.6% | 31.0% | 26.2% | 4.19 | 2.32 |
| V Beta 14 | 201 | 10 | 17.0% | 3.5% | 5.9% | 17.0% | −3.18 | −0.01 |
| V Beta 14 | 204 | 11 | 10.5% | 6.0% | 4.1% | | −1.08 | |
| V Beta 14 | 207 | 12 | 4.8% | 2.7% | 1.3% | | −1.31 | |
| V Beta 14 | 210 | 13 | 3.0% | 1.2% | 1.4% | 0.6% | −1.27 | −1.92 |
| V Beta 14 | 213 | 14 | 2.1% | 0.8% | 0.9% | | 1.40 | |
| V Beta 14 | 216 | 15 | 1.6% | 0.7% | 1.5% | 2.7% | −0.25 | 1.46 |
| V Beta 14 | 219 | 16 | 1.2% | 0.8% | | 1.6% | | 0.44 |
| V Beta 14 | 222 | 17 | 0.6% | 0.7% | | 1.8% | | 1.76 |
| V Beta 14 | 225 | 18 | 0.3% | 0.3% | | 0.8% | | 1.64 |
| V Beta 14 | 228 | 19 | 0.1% | 0.1% | | | | |
| V Beta 14 | 231 | 20 | | | | | | |
| V Beta 14 | 234 | 21 | | | | | | |
| V Beta 15 | 174 | 0 | | | | | | |
| V Beta 15 | 177 | 1 | | | | | | |
| V Beta 15 | 180 | 2 | | | | | | |
| V Beta 15 | 183 | 3 | | | | | | |
| V Beta 15 | 186 | 4 | 0.1% | 0.1% | | | | |
| V Beta 15 | 189 | 5 | 0.3% | 0.3% | | | | |
| V Beta 15 | 192 | 6 | 2.6% | 1.0% | | 11.8% | | 9.54 |
| V Beta 15 | 195 | 7 | 7.8% | 2.0% | 24.0% | | 8.11 | |
| V Beta 15 | 198 | 8 | 14.6% | 2.4% | 15.5% | 8.5% | 0.36 | −2.60 |
| V Beta 15 | 201 | 9 | 16.1% | 2.4% | 17.8% | 18.7% | 0.68 | 1.06 |
| V Beta 15 | 204 | 10 | 18.2% | 3.4% | 28.7% | 51.8% | 3.14 | 10.00 |
| V Beta 15 | 207 | 11 | 16.1% | 1.3% | 6.8% | | −7.16 | |
| V Beta 15 | 210 | 12 | 9.9% | 1.1% | 2.5% | 9.3% | −6.62 | −0.56 |
| V Beta 15 | 213 | 13 | 4.9% | 1.9% | 2.9% | | −1.04 | |
| V Beta 15 | 216 | 14 | 2.2% | 0.9% | 0.4% | | −1.98 | |
| V Beta 15 | 219 | 15 | 2.3% | 1.2% | 0.4% | | −1.54 | |
| V Beta 15 | 222 | 16 | 2.0% | 0.9% | 1.0% | | −1.06 | |

TABLE X-continued

Intrafamily Fragment Analysis of V Beta Gene CDR3 Regions from a Patient with Primary Biliary Cirrhosis

| Families | Fragment Length (nt) | CDR3 Length (aa) | Control Mean | Control SD | Patient PBMC | Patient Liver | X/SD* PBMC | X/SD* Liver |
|---|---|---|---|---|---|---|---|---|
| V Beta 15 | 225 | 17 | 1.5% | 0.8% | | | | |
| V Beta 15 | 228 | 18 | 0.9% | 1.0% | | | | |
| V Beta 15 | 231 | 19 | 0.3% | 0.5% | | | | |
| V Beta 15 | 234 | 20 | 0.1% | 0.2% | | | | |
| V Beta 15 | 237 | 21 | 0.1% | 0.2% | | | | |
| V Beta 16 | 216 | 0 | | | | | | |
| V Beta 16 | 219 | 1 | | | | | | |
| V Beta 16 | 222 | 2 | | | | | | |
| V Beta 16 | 225 | 3 | | | | 0.5% | | |
| V Beta 16 | 228 | 4 | 0.2% | 0.2% | | 0.5% | | 1.27 |
| V Beta 16 | 231 | 5 | 0.8% | 1.3% | | 0.7% | | −0.15 |
| V Beta 16 | 234 | 6 | 3.2% | 1.8% | | 0.9% | | −1.33 |
| V Beta 16 | 237 | 7 | 8.3% | 3.8% | 7.2% | 2.5% | −0.29 | −1.53 |
| V Beta 16 | 240 | 8 | 15.1% | 2.3% | 15.8% | 1.1% | 0.34 | −6.14 |
| V Beta 16 | 243 | 9 | 17.3% | 4.8% | 17.8% | | 0.11 | |
| V Beta 16 | 246 | 10 | 19.6% | 3.5% | 16.5% | | −0.87 | |
| V Beta 16 | 249 | 11 | 15.3% | 3.4% | 15.6% | 37.5% | 0.08 | 6.55 |
| V Beta 16 | 252 | 12 | 9.0% | 4.7% | 27.0% | 1.1% | 3.84 | −1.71 |
| V Beta 16 | 255 | 13 | 6.4% | 7.5% | | | | −0.85 |
| V Beta 16 | 258 | 14 | 2.0% | 1.2% | | 2.3% | −1.63 | −0.28 |
| V Beta 16 | 261 | 15 | 1.0% | 0.5% | | | | −2.25 |
| V Beta 16 | 264 | 16 | 0.8% | 0.6% | | | | −1.26 |
| V Beta 16 | 267 | 17 | 0.5% | 0.3% | | 2.9% | −1.70 | 8.00 |
| V Beta 16 | 270 | 18 | 0.2% | 0.2% | | 29.1% | −0.85 | 129.21 |
| V Beta 16 | 273 | 19 | 0.1% | | | | | |
| V Beta 16 | 276 | 20 | | | | | | |
| V Beta 16 | 279 | 21 | | | | | | |
| V Beta 17 | 216 | 0 | | | | | | |
| V Beta 17 | 219 | 1 | | | 0.5% | 0.5% | | |
| V Beta 17 | 222 | 2 | | | 0.7% | 1.9% | | |
| V Beta 17 | 225 | 3 | 0.1% | 0.2% | 1.1% | | 4.89 | |
| V Beta 17 | 228 | 4 | 0.4% | 0.5% | 1.7% | 2.5% | 2.46 | 4.04 |
| V Beta 17 | 231 | 5 | 1.0% | 1.1% | 2.0% | 2.2% | 0.94 | 1.15 |
| V Beta 17 | 234 | 6 | 3.4% | 2.1% | 2.5% | | −0.46 | |
| V Beta 17 | 237 | 7 | 11.0% | 7.8% | 4.2% | 15.8% | −0.86 | 0.61 |
| V Beta 17 | 240 | 8 | 17.8% | 4.3% | 5.1% | | −2.95 | |
| V Beta 17 | 243 | 9 | 24.4% | 3.4% | 11.1% | 15.0% | −3.87 | −2.72 |
| V Beta 17 | 246 | 10 | 22.7% | 7.7% | 17.5% | 29.9% | −0.68 | 0.93 |
| V Beta 17 | 249 | 11 | 9.6% | 3.9% | 17.8% | 24.3% | 2.13 | 3.82 |
| V Beta 17 | 252 | 12 | 4.1% | 1.5% | 18.6% | 7.8% | 9.53 | 2.44 |
| V Beta 17 | 255 | 13 | 2.0% | 1.3% | 6.4% | | 3.31 | |
| V Beta 17 | 258 | 14 | 1.4% | 1.0% | 5.4% | | 4.07 | |
| V Beta 17 | 261 | 15 | 1.1% | 0.4% | 2.8% | | 4.35 | |
| V Beta 17 | 264 | 16 | 0.7% | 0.7% | 0.8% | | 0.15 | |
| V Beta 17 | 267 | 17 | 0.2% | 0.2% | 1.2% | | 5.83 | |
| V Beta 17 | 270 | 18 | | | 0.4% | | | |
| V Beta 17 | 273 | 19 | | | | | | |
| V Beta 17 | 276 | 20 | | | | | | |
| V Beta 17 | 279 | 21 | | | | | | |
| V Beta 18 | 201 | 0 | | | | | | |
| V Beta 18 | 204 | 1 | | | | | | |
| V Beta 18 | 207 | 2 | | | | | | |
| V Beta 18 | 210 | 3 | | | | | | |
| V Beta 18 | 213 | 4 | 0.2% | 0.3% | | | | |
| V Beta 18 | 216 | 5 | 0.5% | 0.8% | 1.7% | | 1.47 | |
| V Beta 18 | 219 | 6 | 2.4% | 1.6% | 6.1% | | 2.30 | |
| V Beta 18 | 222 | 7 | 8.3% | 4.2% | 13.5% | | 1.23 | |
| V Beta 18 | 225 | 8 | 16.1% | 3.8% | | 9.8% | | −1.67 |
| V Beta 18 | 228 | 9 | 19.6% | 2.5% | 24.3% | 52.5% | 1.86 | 13.09 |
| V Beta 18 | 231 | 10 | 19.2% | 4.0% | 22.4% | 37.7% | 0.82 | 4.64 |
| V Beta 18 | 234 | 11 | 15.0% | 3.1% | 19.1% | | 1.32 | |
| V Beta 18 | 237 | 12 | 6.6% | 1.4% | 3.4% | | −2.22 | |
| V Beta 18 | 240 | 13 | 3.9% | 1.6% | 6.3% | | 1.46 | |
| V Beta 18 | 243 | 14 | 2.9% | 1.8% | | | | |
| V Beta 18 | 246 | 15 | 2.5% | 2.7% | 1.1% | | −0.52 | |
| V Beta 18 | 249 | 16 | 1.6% | 1.3% | 1.2% | | −0.26 | |
| V Beta 18 | 252 | 17 | 1.0% | 0.7% | 0.7% | | −0.35 | |
| V Beta 18 | 255 | 18 | 0.3% | 0.2% | | | | |
| V Beta 18 | 258 | 19 | | | | | | |
| V Beta 18 | 261 | 20 | | | | | | |
| V Beta 18 | 264 | 21 | | | | | | |
| V Beta 20 | 198 | 0 | | | | | | |
| V Beta 20 | 201 | 1 | | | | 0.3% | | |

TABLE X-continued

Intrafamily Fragment Analysis of V Beta Gene CDR3 Regions
from a Patient with Primary Biliary Cirrhosis

| Families | Fragment Length (nt) | CDR3 Length (aa) | Control Mean | Control SD | Patient PBMC | Patient Liver | X/SD* PBMC | X/SD* Liver |
|---|---|---|---|---|---|---|---|---|
| V Beta 20 | 204 | 2 | | | | | | |
| V Beta 20 | 207 | 3 | | | | 3.5% | | |
| V Beta 20 | 210 | 4 | 0.4% | 0.6% | | 1.9% | | 2.65 |
| V Beta 20 | 213 | 5 | 3.5% | 3.7% | 14.1% | 1.8% | 2.88 | −0.47 |
| V Beta 20 | 216 | 6 | 7.9% | 4.0% | 11.2% | 1.3% | 0.82 | −1.64 |
| V Beta 20 | 219 | 7 | 14.8% | 5.1% | 31.9% | 4.1% | 3.33 | −2.10 |
| V Beta 20 | 222 | 8 | 22.9% | 6.0% | 33.5% | 2.1% | 1.77 | −3.46 |
| V Beta 20 | 225 | 9 | 21.7% | 6.4% | 5.0% | 62.5% | −2.60 | 6.37 |
| V Beta 20 | 228 | 10 | 12.5% | 5.2% | 4.3% | | −1.57 | |
| V Beta 20 | 231 | 11 | 5.9% | 2.5% | | | | |
| V Beta 20 | 234 | 12 | 4.7% | 3.3% | | | | |
| V Beta 20 | 237 | 13 | 1.9% | 0.8% | | | | |
| V Beta 20 | 240 | 14 | 1.8% | 1.0% | | 7.1% | | 5.35 |
| V Beta 20 | 243 | 15 | 1.4% | 1.0% | | | | |
| V Beta 20 | 246 | 16 | 0.5% | 0.7% | | | | |
| V Beta 20 | 249 | 17 | 0.1% | 0.3% | | | | |
| V Beta 20 | 252 | 18 | 0.1% | 0.2% | | | | |
| V Beta 20 | 255 | 19 | | | | | | |
| V Beta 20 | 258 | 20 | | | | | | |
| V Beta 20 | 261 | 21 | | | | | | |
| V Beta 21 | 135 | 0 | | | | | | |
| V Beta 21 | 138 | 1 | | | | | | |
| V Beta 21 | 141 | 2 | | | | | | |
| V Beta 21 | 143 | 3 | | | | | | |
| V Beta 21 | 146 | 4 | 0.1% | 0.1% | | | | |
| V Beta 21 | 149 | 5 | 1.9% | 1.3% | | | | |
| V Beta 21 | 152 | 6 | 6.0% | 2.9% | 22.2% | | 5.57 | |
| V Beta 21 | 155 | 7 | 11.3% | 5.4% | 9.2% | | −0.39 | |
| V Beta 21 | 158 | 8 | 19.0% | 5.5% | 16.8% | | −0.40 | |
| V Beta 21 | 161 | 9 | 23.4% | 4.7% | | 4.7% | | −3.97 |
| V Beta 21 | 164 | 10 | 18.6% | 5.6% | 31.7% | 58.0% | 2.33 | 7.05 |
| V Beta 21 | 167 | 11 | 8.7% | 5.5% | 14.5% | 37.3% | 1.05 | 5.19 |
| V Beta 21 | 170 | 12 | 4.5% | 2.7% | 2.5% | | −0.74 | |
| V Beta 21 | 173 | 13 | 2.0% | 1.4% | 1.6% | | −0.28 | |
| V Beta 21 | 176 | 14 | 1.2% | 0.6% | 1.4% | | 0.19 | |
| V Beta 21 | 179 | 15 | 1.7% | 1.5% | | | | |
| V Beta 21 | 182 | 16 | 0.8% | 0.8% | | | | |
| V Beta 21 | 185 | 17 | 0.3% | 0.5% | | | | |
| V Beta 21 | 188 | 18 | 0.2% | 0.3% | | | | |
| V Beta 21 | 191 | 19 | 0.1% | 0.2% | | | | |
| V Beta 21 | 194 | 20 | | | | | | |
| V Beta 21 | 197 | 21 | | | | | | |
| V Beta 22 | 316 | 0 | | | | | | |
| V Beta 22 | 319 | 1 | | | 1.0% | | | |
| V Beta 22 | 322 | 2 | | | 1.6% | | | |
| V Beta 22 | 325 | 3 | | | 1.2% | | | |
| V Beta 22 | 328 | 4 | | | 1.8% | | | |
| V Beta 22 | 331 | 5 | | | 3.3% | | | |
| V Beta 22 | 334 | 6 | 0.7% | 1.1% | 2.8% | | 1.86 | |
| V Beta 22 | 337 | 7 | 3.5% | 2.7% | 4.4% | 4.9% | 0.34 | 0.52 |
| V Beta 22 | 340 | 8 | 9.5% | 8.9% | 20.3% | | 1.22 | |
| V Beta 22 | 343 | 9 | 17.7% | 9.4% | 10.1% | 47.1% | −0.81 | 3.14 |
| V Beta 22 | 346 | 10 | 20.8% | 6.3% | 8.4% | | −1.98 | |
| V Beta 22 | 349 | 11 | 19.9% | 5.9% | 11.1% | 47.9% | −1.47 | 4.73 |
| V Beta 22 | 352 | 12 | 13.7% | 8.2% | 13.6% | | −0.01 | |
| V Beta 22 | 355 | 13 | 8.3% | 9.2% | | | | |
| V Beta 22 | 358 | 14 | 3.4% | 2.9% | 14.7% | | 3.93 | |
| V Beta 22 | 361 | 15 | 1.3% | 1.0% | 2.8% | | 1.55 | |
| V Beta 22 | 364 | 16 | 0.7% | 0.6% | 1.2% | | 0.78 | |
| V Beta 22 | 367 | 17 | 0.4% | 0.4% | 0.9% | | 1.50 | |
| V Beta 22 | 370 | 18 | 0.1% | | 0.7% | | | |
| V Beta 22 | 373 | 19 | | | | | | |
| V Beta 22 | 376 | 20 | | | | | | |
| V Beta 22 | 379 | 21 | | | | | | |
| V Beta 23 | 259 | 0 | | | | | | |
| V Beta 23 | 262 | 1 | 0.1% | | | | | |
| V Beta 23 | 265 | 2 | 0.1% | | | | | |
| V Beta 23 | 268 | 3 | 0.2% | | | | | |
| V Beta 23 | 271 | 4 | 0.6% | 0.7% | 1.0% | | 0.72 | |
| V Beta 23 | 274 | 5 | 0.8% | 0.7% | 0.3% | | −0.65 | |
| V Beta 23 | 277 | 6 | 1.6% | 1.6% | 0.9% | | −0.42 | |
| V Beta 23 | 280 | 7 | 5.5% | 4.4% | 32.8% | | 6.20 | |
| V Beta 23 | 283 | 8 | 10.9% | 10.6% | 30.3% | | 1.83 | |

TABLE X-continued

Intrafamily Fragment Analysis of V Beta Gene CDR3 Regions from a Patient with Primary Biliary Cirrhosis

| Families | Fragment Length (nt) | CDR3 Length (aa) | Control Mean | Control SD | Patient PBMC | Patient Liver | X/SD* PBMC | X/SD* Liver |
|---|---|---|---|---|---|---|---|---|
| V Beta 23 | 286 | 9 | 13.6% | 7.0% | 25.2% | 3.1% | 1.66 | −1.49 |
| V Beta 23 | 289 | 10 | 23.6% | 10.3% | 5.3% | 88.1% | −1.78 | 6.25 |
| V Beta 23 | 292 | 11 | 15.0% | 7.0% | 1.3% | 8.8% | −1.97 | −0.89 |
| V Beta 23 | 295 | 12 | 11.3% | 6.4% | | | | |
| V Beta 23 | 298 | 13 | 6.1% | 3.7% | | | | |
| V Beta 23 | 301 | 14 | 3.5% | 2.1% | 1.2% | | −1.12 | |
| V Beta 23 | 304 | 15 | 2.4% | 2.2% | 1.0% | | −0.66 | |
| V Beta 23 | 307 | 16 | 2.4% | 1.5% | 0.5% | | −1.23 | |
| V Beta 23 | 310 | 17 | 1.2% | 1.3% | | | | |
| V Beta 23 | 313 | 18 | 0.6% | 0.6% | | | | |
| V Beta 23 | 316 | 19 | 0.4% | 0.5% | | | | |
| V Beta 23 | 319 | 20 | | | | | | |
| V Beta 23 | 322 | 21 | | | | | | |
| V Beta 24 | 329 | 0 | | | | | | |
| V Beta 24 | 332 | 1 | | | | | | |
| V Beta 24 | 335 | 2 | | | 0.7% | | | |
| V Beta 24 | 338 | 3 | | | 2.0% | | | |
| V Beta 24 | 341 | 4 | | | 2.6% | | | |
| V Beta 24 | 344 | 5 | | | 5.7% | | | |
| V Beta 24 | 347 | 6 | 1.6% | 1.8% | 25.8% | 23.3% | 13.69 | 12.32 |
| V Beta 24 | 350 | 7 | 4.4% | 2.9% | | | | |
| V Beta 24 | 353 | 8 | 9.1% | 5.7% | 3.0% | | −1.07 | |
| V Beta 24 | 356 | 9 | 16.1% | 7.0% | 3.0% | | −1.88 | |
| V Beta 24 | 359 | 10 | 22.4% | 11.3% | 46.4% | 76.6% | 2.14 | 4.82 |
| V Beta 24 | 362 | 11 | 21.2% | 8.3% | | | | |
| V Beta 24 | 365 | 12 | 11.8% | 5.8% | 7.1% | | −0.83 | |
| V Beta 24 | 368 | 13 | 6.2% | 6.2% | 3.8% | | −0.39 | |
| V Beta 24 | 371 | 14 | 2.9% | 2.6% | | | | |
| V Beta 24 | 374 | 15 | 1.3% | 1.0% | | | | |
| V Beta 24 | 377 | 16 | | | | | | |
| V Beta 24 | 380 | 17 | | | | | | |
| V Beta 24 | 383 | 18 | | | | | | |
| V Beta 24 | 386 | 19 | | | | | | |
| V Beta 24 | 389 | 20 | | | | | | |
| V Beta 24 | 392 | 21 | | | | | | |

X/SD = (% of patient peak area − % of control peak area)/control SD

The foregoing intrafamily gene fragment length profiles identify a number of potential T cell clonal expansion events (e.g., monoclonal or oligoclonal T cell expansions) in the liver and peripheral blood of the cirrhosis patient that may have clinical significance with respect to the patient's primary biliary cirrhosis autoimmune disease state. More particularly, intrafamily gene fragment analysis as described herein detects a T cell clonal expansion as a fragment peak that is significantly more prevalent in a patient's intrafamily gene fragment length profile than in the corresponding control profile derived from healthy human subjects for the same variable region gene family.

A fragment peak in a patient's intrafamily gene fragment length profile is significantly more prevalent than the corresponding peak in a control profile (for that particular variable region gene family) if it is significantly more prevalent in a statistical sense, e.g., more prevalent by two or more standard deviations, and preferably by three or more standard deviations, than the corresponding peak in the control profile. For example, in the Vα2 control profile in Table IX, the CDR3-8 peak (355 nucleotides) has a prevalence of 18.69% with a standard deviation of 1.90%. In the cirrhosis patient's liver profile, the same fragment has a prevalence of 29.34%, which is significantly more prevalent (by 5.61 standard deviations) than the prevalence of the CDR3-8 peak in the Vα2 control profile. The cirrhosis patient's Vα2 CDR3-7 peak also is significantly more prevalent than the corresponding CDR#-7 control peak (4.30 standard deviations), whereas the patient's Vα2 CDR3-10 and Vα2 CDR3-12 peaks are not significantly more prevalent than their corresponding control peaks (0.21 and 0.38 standard deviations, respectively). Using the three standard deviation criteria, peaks in both the cirrhosis patient's PBMC and liver intrafamily gene fragment length profiles are identified as potential T cell clonal expansion events in this patient, as set forth in greater detail below. The determination of control profiles from healthy individuals was a necessary prerequisite to performing such statistical analyses.

Other investigators performing intrafamily T cell repertoire analysis methods have diagnosed putative clonal expansions where a single, predominant Vβ fragment peak is identified in an intrafamily analysis. See, e.g., Puisieux et al., J. Immunol., 153: 2807 (1994) (identifying an oligoclonal expansion only in Vβ families containing dominating peaks representing 40% or more of the total fluorescence intensity detected within the subfamily). The present method certainly identifies such clonal expansions as well. However, the method of the invention also is capable of identifying many additional clonal expansions. First, the present method provides Vβ intrafamily gene fragment length profiles wherein far greater numbers of fragment peaks are identified than by prior art methods, each such newly discovered peak potentially identifying a clonal expansion.

Moreover, the present invention provides Vα intrafamily fragment analysis procedures and profiles for substantially every Vα family, which approximately doubles the T cell receptor attributes that are analyzed in a method capable of providing only Vβ profiles. Since every αβ T cell has a receptor comprising an α-chain and a β-chain, each T cell clonal expansion should be manifested by the presence of a fragment peak that is more prevalent in one of a patient's intrafamily Vex gene fragment length profiles than in the corresponding Vα control profile and also by the presence of a fragment peak that is more prevalent in one of a patient's intrafamily Vβ gene fragment length profiles than in the corresponding Vβ control profile.

Additionally, the discovery that intrafamily gene fragment length profiles from different healthy individuals are substantially similar for each Vα and Vβ family permits the identification of putative monoclonal/oligoclonal expansion events that prior art methods fail to identify. For example, in addition to identifying a single, "predominant" peak as a putative clonal expansion, the present method identifies peaks as putative clonal expansions based upon the peaks being significantly more prevalent than a corresponding peak in a healthy control, as described above.

Referring to Table IX, the present method identified 49 fragments in the intrafamily Vα gene fragment length profiles derived from the liver that were significantly more prevalent (by three or more standard deviations) than the prevalence of the corresponding fragment in the control intrafamily gene fragment length profiles. Only eighteen of these identified fragments were equal to or greater than 40% of their total family peak area. Conversely, one Vα fragment of equal to or greater than 40% of total family peak area was not identified as a putative clonal expansion because it was not significantly more prevalent (by three or more standard deviations) than the prevalence of its corresponding control peak.

Referring to Table X, the present method identified 64 fragments in the intrafamily Vβ gene fragment length profiles derived from the liver that were significantly more prevalent (by three or more standard deviations) than the prevalence of the corresponding fragment in the control intrafamily gene fragment length profiles. Only eight of these 64 fragments were equal to or greater than 40% of the total family peak area in their particular intrafamily profile. Conversely, two Vβ fragments of equal to or greater than 40% of their total family peak area were not identified as a putative clonal expansion because they were not significantly more prevalent (by three or more standard deviations) than the prevalence of their corresponding control peaks.

With respect to intrafamily gene fragment length profiles derived from the cirrhosis patient's peripheral blood, only two fragments were identified that represented greater than 40% of the total peak area of their respective intrafamily profile. The first, in the Vα29 profile, was more prevalent than the corresponding fragment in the Vα29 control profile by ≧3 standard deviations. The second, in the Vβ24 profile, was more prevalent than the corresponding fragment in the control Vβ24 control profile by less than three standard deviations but more than two standard deviations. Multiple fragments were identified in the patient's peripheral blood profiles that were more prevalent than the corresponding fragment in the control profile by at least two standard deviations. Some of these fragments also were identified as being significantly more prevalent in the liver profiles by ≧ three standard deviations, but most were not. One interpretation of this data is that those T cells which actively mediate an immune response may leave the blood quickly to enter and concentrate in the target organ, in this case the liver.

It will be understood by those skilled in the art that the putative identification of a clonal expansion event by the intrafamily gene fragment analysis method of the invention can be further verified using techniques known in the art. For example, appropriate Jβ "run-off" reactions may be conducted to further characterize the gene segments which encode the TCR of a putative proliferating T cell clone.

More preferably, DNA fragments from the profile peak of interest (or from a subsequent Jβ "run-off" reaction) are sequenced to confirm the presence of a T cell clonal expansion. Single predominant peaks may be directly sequenceable. Otherwise, in a preferred procedure, DNA fragments from the profile peak of interest are isolated (e.g., via eletroelution from the polyacrylamide gel), cloned into a suitable vector, and transformed or transfected into a suitable host. Thereafter, the fragment insert in a number of the transformants (e.g., 20 to 40 clones) is sequenced. The high prevalence of the profile peak of interest is attributed to a T cell clonal expansion where multiple copies of the same CDR3 gene sequence are found among the transformants.

Alternatively, the total DNA amplified by the putative clonal fragment's family specific primer using PCR is cloned and the insert lengths of individual clones are determined by well-known electrophoresis procedures. Clones having an insert corresponding to the same length as the putative clonal fragment are sequenced. If the observed expansion of the fragment length in question were truly largely monoclonal, then the majority of clone fragments of that length are observed to share an identical sequence.

The determination of a CDR3 nucleic acid sequence of autoreactive T cells identified by intrafamily gene fragment analysis and sequencing as described herein provides useful information for vaccine development to treat the autoimmune disorder. For example, the CDR3 nucleic acid sequence is translated into a peptide sequence, and polypeptides having the sequence are synthesized recombinantly or synthetically. The CDR3 polypeptides synthesized in this manner are used as a vaccine (directly, in combination with an adjuvant, and/or in covalent linkage to an immunogenic moiety, etc.). The vaccination stimulates production of anti-idiotypic T cells or anti-idiotypic antibodies, to down-regulate or eliminate the autoimmune T cell populations expressing the CDR3 sequences.

EXAMPLE 8

Correlating a Particular Disorder to a Characteristic Intrafamily Gene Fragment Length Profile As described above, T cell immunoproliferative conditions correlate with detectable changes (e.g., increases in the prevalence of one or more particular gene fragment lengths) in one or more of an individual's intrafamily gene fragment length profiles. The procedure described below enables one to correlate a particular disorder to a characteristic intrafamily gene fragment length profile.

Bulk lymphocytes are isolated from a blood sample obtained from an individual. A first sample of the bulk lymphocytes is employed to generate a first intrafamily gene fragment length profile for the individual for one or more Vα and Vβ gene families (and preferably for substantially all Vα and Vβ gene families), using the procedures described in preceding examples.

A second sample of the bulk lymphocytes (approx. $10^3$–$10^6$ cells) is cultured in the presence of one or more specific antigens associated with a disorder of interest. For example, if the disorder of interest is hepatitis, then T lymphocytes are cultured in the presence of hepatitis viral antigenic determinants. Standard T cell culture conditions are employed to culture the cells, and those T cells that are specifically immunoreactive with the antigen(s) are stimulated and proliferate in the culture by clonal expansion. As a control, a third sample of the bulk lymphocytes is cultured under identical conditions without the antigen(s).

After culturing the T cells for one to six weeks, samples from each culture are withdrawn and used to generate intrafamily gene fragment length profiles for the same Vα and Vβ gene families that were assayed initially (preferably substantially all Vα and Vβ gene families). The profiles derived from the T cells cultured with the antigen are compared to the corresponding profiles derived from the control culture and from the uncultured T cells, to detect the presence of discrete fragment lengths that are more prevalent in the antigen culture profiles than in the other profiles. The fragment peaks of increased prevalence are correlated to an immunoproliferative response to the antigen of interest.

The correlation of particular fragment peaks to particular antigens increases the rapidity and decreases the cost of clinical applications of intrafamily gene fragment analysis methods described herein, because such a correlation obviates the need to continually monitor all variable region gene families when monitoring an individual with respect to a particular disorder (e.g., when continually monitoring an individual for a particular disease state because the individual is subjected to a high-risk environment for the particular disease state).

The correlation of particular fragment peaks to particular antigens also facilitates the identification of clonal T cell populations that are specifically immunoreactive with pathogens responsible for persistent infections (e.g., *M. leprae*, HIV). Such T cell populations can be expanded in vitro and reinfused into a patient as therapeutic agents.

Also, culture of peripheral blood lymphocytes provides a source of cells for identification of antigen-reactive CDR3 regions by the methods described herein when the antigen may be known and available (e.g., the HLA haplotype of an allogaft donor), but the affected target tissue itself is not amenable to sampling.

While the present invention has been described in terms of specific embodiments, it is understood that variations and modifications will occur to those skilled in the art. Accordingly, only such limitations as appear in the appended claims should be placed on the invention.

What is claimed is:

1. A method of assaying for a T cell immunoproliferative condition in a human individual comprising the steps of:
  (a) obtaining cells from said individual, said cells including T lymphocytes (T cells);
  (b) generating an assay intrafamily gene fragment length profile from said cells for T cell receptor (TCR) third-complementarity-determining regions (CDR3) of an α-chain variable region gene family (Vα) by:
    (i) isolating RNA from said cells;
    (ii) synthesizing cDNA from said RNA;
    (iii) performing a first polymerase chain reaction (PCR) with a reaction mixture that includes cDNA from step (ii) as a template; a family-specific TCR α-chain variable region oligonucleotide primer; and a TCR α-chain constant region oligonucleotide primer; wherein said first PCR amplifies DNA encoding TCR-CDR3 of an αβ T cell receptor α-chain variable region gene family;
    (iv) performing a second PCR with a reaction mixture that includes amplified DNA from step (iii) as a template; the family-specific TCR α-chain variable region oligonucleotide primer; and a nested TCR α-chain constant region oligonucleotide primer; wherein said second polymerase chain reaction provides amplified DNA fragments encoding TCR-CDR3 of said αβ T cell receptor α-chain variable region gene family;
    (v) separating DNA fragments from the second polymerase chain reaction by length; and
    (vi) determining a prevalence of DNA fragments separated according to step (v), to provide an intrafamily gene fragment length profile for said αβ T cell receptor α-chain variable region gene family; and
  (c) comparing the assay profile of step (b) to a control intrafamily gene fragment length profile derived from blood cells of a healthy human subject, to determine a presence or an absence of at least one gene fragment length that is more prevalent in the assay profile than the control profile, wherein said control profile is for the same TCR-CDR3 α-chain variable region gene family as the assay profile, and wherein the presence of at least one gene fragment length that is more prevalent in the assay profile than the control profile is correlated to a T cell immunoproliferative condition.

2. The method of claim 1 wherein, in step (ii), random primers are used to synthesize the cDNA.

3. The method of claim 1 wherein the cells are derived from peripheral blood from the individual.

4. A method according to claim 1 wherein, in the separating step (b)(v), at least two DNA size standards are included with the DNA fragments from the second polymerase chain reaction.

5. The method of claim 1 comprising performing steps (b) and (c) for 28 TCR α-chain variable region gene families, wherein the presence of a T cell immunoproliferative condition is correlated to at least one gene fragment length that is more prevalent in at least one of the assay profiles than the corresponding control profile.

6. The method of claim 5 wherein each of the 28 control profiles contains at least 8 fragment lengths.

7. The method of claim 1 wherein the control profile contains at least 8 fragment lengths.

8. The method of claim 7 wherein the control profile is an averaged profile derived from a plurality of single TCR-CDR3 intrafamily gene fragment length profiles, and wherein each of said single profiles is derived from blood cells of a healthy human subject.

9. The method of claim 8 wherein the presence of at least one gene fragment length that is more prevalent by at least two standard deviations in the assay profile than the control profile is correlated to a T cell immunoproliferative condition.

10. The method of claim 7 wherein the control profile contains at least 10 fragment lengths.

11. The method of claim 7 wherein the assay profile contains at least 8 fragment lengths.

12. A method of assaying for a T cell immunoproliferative condition in a human individual comprising the steps of:
  (a) obtaining cells from said individual, said cells including T lymphocytes (T cells);
  (b) generating an assay intrafamily gene fragment length profile from said cells for T cell receptor (TCR) third-complementarity-determining-regions (CDR3) of a β-chain variable region gene family (Vβ); and
  (c) comparing the assay profile of step (b) to a control intrafamily gene fragment length profile of at least 12 fragment lengths, to determine a presence or an absence of at least one gene fragment length that is more prevalent in the assay profile than the control profile, wherein said control profile is an averaged profile for the same variable region gene family as the assay profile, wherein the control profile has been derived from a plurality of single intrafamily gene fragment length profiles, each of said single profiles having been derived from blood cells of a healthy human subject, and wherein the presence of at least one gene fragment length that is more prevalent in the assay profile than the control profile is correlated to a T cell immunoproliferative condition.

13. The method of claim 12 wherein the cells are derived from peripheral blood from the individual.

14. The method of claim 11 comprising performing steps (b) and (c) for 25 TCR β-chain variable region gene families, wherein the presence of a T cell immunoproliferative condition is correlated to at least one gene fragment length that is more prevalent in at least one of the assay profiles than the corresponding control profile.

15. The method of claim 12 wherein the assay profile contains at least 12 fragment lengths.

16. The method of claim 12 wherein the presence of at least one gene fragment length that is more prevalent by at least two standard deviations in the assay profile than the control profile is correlated to a T cell immunoproliferative condition.

17. The method of claim 12 further comprising the steps of:

(d) generating an assay intrafamily gene fragment length profile from said cells for TCR-CDR3 of an α-chain variable region gene family (Vα);

(e) comparing the assay profile of step (d) to a control intrafamily Vα gene fragment length profile derived from blood cells of a healthy human subject, to determine a presence or an absence of at least one gene fragment length that is more prevalent in the assay profile of step (d) than the control Vα profile, wherein said control Vα profile is for the same variable region gene family as the assay profile of step (d), and wherein a T cell immunoproliferative condition is correlated to:

(i) the presence of at least one gene fragment length that is more prevalent in the assay profile of step (b) than the control profile of step (c), and (ii) the presence of at least one gene fragment length that is more prevalent in the assay profile of step (d) than the control Vα profile.

18. The method of claim 17 comprising:

performing steps (b) and (c) for 25 TCR β-chain variable region gene families and performing steps (d) and (e) for 28 TCR α-chain variable region gene families, wherein a T cell immunoproliferative condition is correlated to:

(i) the presence of at least one gene fragment length that is more prevalent in at least one of the assay profiles of step (b) than the corresponding control profile of step (c), and (ii) the presence of at least one gene fragment length that is more prevalent in at least one of the assay profiles of step (d) than the corresponding control Vα profile.

19. The method of claim 18 wherein the 25 Vβ assay intrafamily gene fragment length profiles and and the 28 Vα assay intrafamily gene fragment length profiles are generated in one electrophoresis on a single polyacrylamide gel.

20. The method of claim 12 wherein step (b) comprises the steps of:

(i) isolating RNA from said cells;

(ii) synthesizing cDNA from said RNA;

(iii) subjecting the cDNA to a polymerase chain reaction using a family-specific Vβ oligonucleotide primer to amplify DNA encoding T cell receptor third-complimentarity-determining regions (TCR-CDR3) of a single Vβ gene family;

(iv) separating DNA fragments from the polymerase chain reaction by length; and (v) determining a prevalence of each fragment length to provide an assay intrafamily gene fragment length profile.

21. The method of claim 20 wherein, in step (ii), random primers are used to synthesize the cDNA.

22. A method according to claim 20 wherein, in the separating step (iv), at least two DNA size standards are included with the DNA fragments from the polymerase chain reaction.

23. A method of assaying for a T cell immunoproliferative condition in a human individual comprising the steps of:

(a) obtaining cells from said individual, said cells including T lymphocytes (T cells);

(b) generating an assay intrafamily gene fragment length profile from said cells for T cell receptor (TCR) third-complementarity-determining-regions (CDR3) of a β-chain variable region gene family (Vβ); and (c) comparing the assay profile of step (b) to a control intrafamily gene fragment length profile of at least 14 fragment lengths derived from blood cells of a healthy human subject, to determine a presence or an absence of at least one gene fragment length that is more prevalent in the assay profile than the control profile, wherein said control profile is for the same variable region gene family as the assay profile, and wherein the presence of at least one gene fragment length that is more prevalent in the assay profile than the control profile is correlated to a T cell immunoproliferative condition.

24. The method of claim 23 wherein the control profile is an averaged profile derived from a plurality of single intrafamily gene fragment length profiles, and wherein each of said single profiles is derived from blood cells of a healthy human subject.

25. A kit for performing intrafamily T cell receptor (TCR) repertoire analysis comprising, in association:

a family-specific oligonucleotide primer for PCR amplification of third-complimentarity-determining-regions of a single TCR variable-region gene family; and an intrafamily gene fragment length profile for the TCR variable-region gene family, wherein the intrafamily gene fragment length profile is an averaged profile derived from a plurality of single intrafamily gene fragment length profiles, and wherein each of the single profiles is derived from blood cells of healthy human subjects.

26. The kit of claim 25 comprising: 25 family-specific oligonucleotide primers for PCR amplification of third-complimentarity-determining-regions of 25 TCR Vβ gene families; and intrafamily gene fragment length profiles of at least 12 fragment lengths for each of said TCR Vβ gene families, wherein each of the profiles is an averaged profile derived from a plurality of single intrafamily gene fragment length profiles, and wherein each of the single profiles is derived from blood cells of a healthy human subject.

27. The kit of claim 25 wherein the single TCR variable region gene family is a Vα gene family, and wherein the intrafamily gene fragment length profile contains at least 8 fragment lengths.

28. The kit of claim 27 wherein the intrafamily gene fragment length profile contains at least 10 fragment lengths.

29. The kit of claim 25 comprising: twenty-eight family-specific oligonucleotide primers for PCR amplification of third-complimentarity-determining-regions of twenty-eight TCR Vα gene families; and intrafamily gene fragment length profiles of at least 8 fragment lengths for each of said TCR Vα gene families, wherein each of said profiles is an averaged profile derived from a plurality of single intrafamily gene fragment length profiles, and wherein each of the single profiles is derived from blood cells of a healthy human subject.

30. The kit of claim 25 wherein the single TCR variable region gene family is a Vβ gene family, and wherein the intrafamily gene fragment length profile contains at least 13 fragment lengths.

31. A method for generating an intrafamily gene fragment length profile useful for analyzing the αβ T cell repertoire in a mammalian subject, comprising the steps of:

(a) providing a cell sample from a mammalian subject, said cell sample comprising αβ T cells;

(b) isolating RNA from said cell sample;

(c) synthesizing cDNA from said RNA;

(d) performing a first polymerase chain reaction with a reaction mixture comprising:
  (i) cDNA from step (c) as a template;
  (ii) a family-specific T cell receptor α-chain variable region oligonucleotide primer; and
  (iii) a first T cell receptor (TCR) α-chain constant region oligonucleotide primer,
wherein said first polymerase chain reaction amplifies DNA encoding T cell receptor third-complimentarity-determining-regions (TCR-CDR3) of an αβ T cell receptor α-chain variable region gene family;
(e) performing a second polymerase chain reaction with a reaction mixture comprising:
  (i) amplified DNA from step (d) as a template, (ii) the family-specific T cell receptor α-chain variable region oligonucleotide primer, and
  (iii) a second T cell receptor α-chain constant region oligonucleotide primer; wherein said second polymerase chain reaction provides amplified DNA fragments encoding TCR-CDR3 of said αβ T cell receptor α-chain variable region gene family;
(f) separating DNA fragments from the second polymerase chain reaction by length; and
(g) determining a prevalence of DNA fragments separated according to step (f), to provide an intrafamily gene fragment length profile for said αβ T cell receptor α-chain variable region gene family.

32. A method of assaying for a T cell immunoproliferative condition in a mammalian individual comprising the steps of:
(A) generating an assay intrafamily gene fragment length profile for a mammalian individual according to claim 31; and
(B) comparing the assay intrafamily gene fragment length profile of step (A) to a control intrafamily gene fragment length profile derived from blood cells of a healthy mammalian subject of the same species as said mammalian individual, to determine a presence or an absence of at least one gene fragment length that is more prevalent in the assay profile than the control profile, wherein said control profile is for the same variable region gene family as the assay profile, and wherein the presence of at least one gene fragment length that is more prevalent in the assay profile than the control profile is correlated to a T cell immunoproliferative condition.

33. A method according to claim 31 wherein, in the separating step (f), at least two DNA size standards are included with the DNA fragments from the second polymerase chain reaction.

34. The method of claim 31 wherein steps (a)–(g) are performed for 28 TCR α-chain variable region gene families.

35. The method of claim 31 wherein the mammalian subject is human; and
wherein in step (f) an aliquot from said second polymerase chain reaction is separated via polyacrylamide gel electrophoresis, said aliquot selected to permit detection of low-abundance fragment peaks without concomitant overloading of high-abundance fragment peaks, and wherein the intrafamily gene fragment length profile includes a prevalence for 8 to 16 different fragment lengths.

36. The method of claim 35 wherein in step (c), random primers are used to synthesize the cDNA.

37. A method for monitoring the therapeutic efficacy of an immunomodulatory treatment comprising the steps of:

(a) obtaining cells from a human subject in need of an immunomodulatory treatment for a disorder, said cells including T lymphocytes;
(b) generating a first intrafamily gene fragment length profile from the cells, according to the method of claim 35, for a T cell receptor (TCR) α-chain variable region gene family;
(c) correlating a discreet gene fragment length within said first intrafamily gene fragment length profile to a T cell proliferative response to said disorder;
(d) determining a pre-treatment gene fragment length prevalence for said discreet gene fragment length relative to the prevalence of all gene fragment lengths in said first intrafamily gene fragment length profile;
(e) treating said human subject with said immunomodulatory treatment for said disorder;
(f) obtaining a cell sample from said human subject after initiating treatment of said human subject according to step (e), said cell sample including T lymphocytes;
(g) generating a second intrafamily gene fragment length profile from the cell sample of step (f), according to the method of claim 35, for the TCR α-chain variable region gene family selected in step (b);
(h) determining a treatment gene fragment length prevalence for said discreet gene fragment relative to the prevalence of all gene fragment lengths in said second profile; and
(i) monitoring the therapeutic efficacy of said immunomodulatory treatment by comparing the treatment gene fragment length prevalence of step (h) with the pre-treatment gene fragment length prevalence of step (d), wherein:
  (1) a treatment gene fragment length prevalence greater than a pre-treatment prevalence is correlated to an immunoproliferative response to the treatment of step (e), and
  (2) a treatment gene fragment length prevalence less than a pre-treatment gene fragment length prevalence is correlated to an immunosuppressive response to the treatment of step (e).

38. The method of claim 37 wherein the immunomodulatory treatment is an immunoproliferative treatment for a disorder selected from the group consisting of neoplasia and infection.

39. The method of claim 37 wherein the immunomodulatory treatment is an immunosuppressive treatment for a disorder selected from the group consisting of an autoimmune disorder and an allograft rejection disorder.

40. The method of claim 37 wherein the immunomodulatory treatment is a vaccine for a prophylactic treatment of a disorder.

41. In a T cell repertoire analysis, the improvement wherein at least twenty-eight Vα intrafamily gene fragment length profiles generated according to the method of claim 31 and twenty-five Vβ intrafamily gene fragment length profiles are generated in one electrophoresis on a single polyacrylamide gel.

42. A T cell repertoire analysis according to claim 41, wherein at least two DNA size standards are included in each sample-containing lane in the polyacrylamide gel.

43. A method of generating an intrafamily gene fragment length profile from human T cells for a T cell receptor β-chain variable region gene family (Vβ), comprising the steps of:
(I) providing a cell sample from a human subject, said cell sample comprising αβ T cells;

(II) isolating RNA from human T cells;

(III) synthesizing cDNA from said RNA;

(IV) subjecting the cDNA to a polymerase chain reaction (PCR) using a family-specific Vβ oligonucleotide primer and a second primer, to amplify DNA encoding T cell receptor third-complimentarity-determining regions (TCR-CDR3) of said Vβ gene family, wherein one of the primers comprises a label;

(V) separating an aliquot of the amplified DNA from said PCR by DNA fragment length, using polyacrylamide gel electrophoresis; and (VI) generating an intrafamily gene fragment length profile by measuring peak areas from said polyacrylamide gel to determine DNA fragment length prevalences, wherein relative peak areas are indicative of fragment length prevalences; and wherein the aliquot of step (V) is selected to permit detection of low-abundance fragment peaks without concomitant overloading of high-abundance fragment peaks, and wherein the intrafamily gene fragment length profile includes a prevalence for 14 to 21 different fragment lengths.

44. The method of claim 43 wherein the aliquot of step (V) is about 50–75% of an aliquot that results in the maximum resolvable fragment peak for the most prevalent fragment length in a normal intrafamily gene fragment length profile for said Vβ gene family.

45. The method of claim 43 wherein, in step (III), random primers are used to synthesize the cDNA.

46. A method for monitoring the therapeutic efficacy of an immunomodulatory treatment comprising the steps of:

(a) obtaining cells from a human subject in need of an immunomodulatory treatment for a disorder, said cells including T lymphocytes;

(b) generating a first intrafamily gene fragment length profile from the cells, according to the method of claim 43, for a T cell receptor (TCR) β-chain variable region gene family;

(c) correlating a discreet gene fragment length within said first intrafamily gene fragment length profile to a T cell proliferative response to said disorder;

(d) determining a pre-treatment gene fragment length prevalence for said discreet gene fragment length relative to the prevalence of all gene fragment lengths in said first intrafamily gene fragment length profile;

(e) treating said human subject with said immunomodulatory treatment for said disorder;

(f) obtaining a cell sample from said human subject after initiating treatment of said human subject according to step (e), said cell sample including T lymphocytes;

(g) generating a second intrafamily gene fragment length profile from the cell sample of step (f), according to the method of claim 43, for the TCR β-chain variable region gene family selected in step (b);

(h) determining a treatment gene fragment length prevalence for said discreet gene fragment relative to the prevalence of all gene fragment lengths in said second profile; and (i) monitoring the therapeutic efficacy of said immunomodulatory treatment by comparing the treatment gene fragment length prevalence of step (h) with the pre-treatment gene fragment length prevalence of step (d), wherein:

(1) a treatment gene fragment length prevalence greater than a pre-treatment prevalence is correlated to an immunoproliferative response to the treatment of step (e), and (2) a treatment gene fragment length prevalence less than a pre-treatment gene fragment length prevalence is correlated to an immunosuppressive response to the treatment of step (e).

47. A method according to claim 43 wherein, in the separating step (V), at least two DNA size standards are included with the aliquot of the amplified DNA from said PCR.

* * * * *

SEQUENCE LISTING (1) GENERAL INFORMATION:

(iii) NUMBER OF SEQUENCES: 61

(2) INFORMATION FOR SEQ ID NO:1:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:1:

GCACAACAGT TCCCTGACTT GCAC                                              24

(2) INFORMATION FOR SEQ ID NO:2:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:2:

TCATCAACCA TGCAAGCCTG ACCT                                              24

(2) INFORMATION FOR SEQ ID NO:3:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:3:

GTCTCTAGAG AGAAGAAGGA GCGC                                              24

(2) INFORMATION FOR SEQ ID NO:4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

ACATATGAGA GTGGATTTGT CATT                                    24

(2) INFORMATION FOR SEQ ID NO:5:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

ATACTTCAGT GAGACACAGA GAAAC                                  25

(2) INFORMATION FOR SEQ ID NO:6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

TTCCCTAACT ATAGCTCTGA GCTG                                    24

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

AGGCCTGAGG GATCCGTCTC                                          20

(2) INFORMATION FOR SEQ ID NO:8:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

CCTGAATGCC CCAACAGCTC TC                                      22

(2) INFORMATION FOR SEQ ID NO:9:

(i) SEQUENCE CHARACTERISTICS:

(A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

ATTTACTTTA ACAACAACGT TCCG                                                  24

(2) INFORMATION FOR SEQ ID NO:10:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

CCTAAATCTC CAGACAAAGC TCAC                                                  24

(2) INFORMATION FOR SEQ ID NO:11:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

CTCCAAAAAC TCATCCTGTA CCTT                                                  24

(2) INFORMATION FOR SEQ ID NO:12:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

TCAACAGTCT CCAGAATAAG GACG                                                  24

(2) INFORMATION FOR SEQ ID NO:13:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

AAAGGAGAAG TCTCAGAT                                                         18

(2) INFORMATION FOR SEQ ID NO:14:

(i) SEQUENCE CHARACTERISTICS:
        (A) LENGTH: 18 base pairs
        (B) TYPE: nucleic acid
        (C) STRANDEDNESS: single
        (D) TOPOLOGY: linear

```
         (ii) MOLECULE TYPE: DNA (xi) SEQUENCE DESCRIPTION: SEQ ID NO:14:

CAAGGAGAAG TCCCCAAT                                                       18

(2) INFORMATION FOR SEQ ID NO:15:

(i) SEQUENCE CHARACTERISTICS:
              (A) LENGTH: 18 base pairs
              (B) TYPE: nucleic acid
              (C) STRANDEDNESS: single
              (D) TOPOLOGY: linear (ii) MOLECULE TYPE: DNA (xi) SEQUENCE DESCRIPTION: SEQ ID NO:15:

GGTGAGGGTA CAACTGCC                                                       18

(2) INFORMATION FOR SEQ ID NO:16:

(i) SEQUENCE CHARACTERISTICS:
              (A) LENGTH: 24 base pairs
              (B) TYPE: nucleic acid
              (C) STRANDEDNESS: single
              (D) TOPOLOGY: linear (ii) MOLECULE TYPE: DNA (xi) SEQUENCE DESCRIPTION: SEQ ID NO:16:

GTCTCTCGAA AAGAGAAGAG GAAT                                                24

(2) INFORMATION FOR SEQ ID NO:17:

(i) SEQUENCE CHARACTERISTICS:
              (A) LENGTH: 24 base pairs
              (B) TYPE: nucleic acid
              (C) STRANDEDNESS: single
              (D) TOPOLOGY: linear (ii) MOLECULE TYPE: DNA (xi) SEQUENCE DESCRIPTION: SEQ ID NO:17:

AGTGTCTCTC GACAGGCACA GGCT                                                24

(2) INFORMATION FOR SEQ ID NO:18:

(i) SEQUENCE CHARACTERISTICS:
              (A) LENGTH: 24 base pairs
              (B) TYPE: nucleic acid
              (C) STRANDEDNESS: single
              (D) TOPOLOGY: linear (ii) MOLECULE TYPE: DNA (xi) SEQUENCE DESCRIPTION: SEQ ID NO:18:

AAAGAGTCTA AACAGGATGA GTCC                                                24

(2) INFORMATION FOR SEQ ID NO:19:

(i) SEQUENCE CHARACTERISTICS:
              (A) LENGTH: 21 base pairs
              (B) TYPE: nucleic acid
              (C) STRANDEDNESS: single
              (D) TOPOLOGY: linear (ii) MOLECULE TYPE: DNA (xi) SEQUENCE DESCRIPTION: SEQ ID NO:19:
```

```
CAGATAGTAA ATGACTTTCA G                                                   21

(2) INFORMATION FOR SEQ ID NO:20:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:20:

GATGAGTCAG GAATGCCAAA GGAA                                                24

(2) INFORMATION FOR SEQ ID NO:21:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:21:

CAATGCCCCA AGAACGCACC CTGC                                                24

(2) INFORMATION FOR SEQ ID NO:22:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:22:

CTCAATGCCC CAAGAACGCA C                                                   21

(2) INFORMATION FOR SEQ ID NO:23:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:23:

AGCTCTGAGG TGCCCCAGAA TCTC                                                24

(2) INFORMATION FOR SEQ ID NO:24:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:24:

TCCAACCTGC AAGGCTTGAC GACT                                                24
```

(2) INFORMATION FOR SEQ ID NO:25:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:25:

AAGTGATCTT GCGCTGTGTC CCCA                                    24

(2) INFORMATION FOR SEQ ID NO:26:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:26:

GCAGGGTCCA GGTCAGGACC CCCA                                    24

(2) INFORMATION FOR SEQ ID NO:27:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:27:

CCCAGTTTGG AAAGCCAGTG ACCC                                    24

(2) INFORMATION FOR SEQ ID NO:28:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:28:

TTCTGATGGC TCAAACAC                                              18

(2) INFORMATION FOR SEQ ID NO:29:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:29:

GGCATTAACG GTTTTGAGGC TGGA                                    24

(2) INFORMATION FOR SEQ ID NO:30:

(i) SEQUENCE CHARACTERISTICS:
        (A) LENGTH: 24 base pairs

```
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:30:

CAGTGTTCCA GAGGGAGCCA TTGT                                          24

(2) INFORMATION FOR SEQ ID NO:31:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:31:

CCGGGCAGCA GACACTGCTT CTTA                                          24

(2) INFORMATION FOR SEQ ID NO:32:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:32:

TTGGTATCGA CAGCTTCACT CCCA                                          24

(2) INFORMATION FOR SEQ ID NO:33:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:33:

CGGCCACCCT GACCTGCAAC TATA                                          24

(2) INFORMATION FOR SEQ ID NO:34:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:34:

TCCGCCAACC TTGTCATCTC CGCT                                          24

(2) INFORMATION FOR SEQ ID NO:35:

(i) SEQUENCE CHARACTERISTICS:
            (A) LENGTH: 24 base pairs
            (B) TYPE: nucleic acid
            (C) STRANDEDNESS: single
            (D) TOPOLOGY: linear
```

-continued (ii) MOLECULE TYPE: DNA (xi) SEQUENCE DESCRIPTION: SEQ ID NO:35:

GCAACATGCT GGCGGAGCAC CCAC                                              24

(2) INFORMATION FOR SEQ ID NO:36:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:36:

CATTCGTTCA AATGTGGGCA AAAG                                              24

(2) INFORMATION FOR SEQ ID NO:37:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:37:

CCAGTACTCC AGACAACGCC TGCA                                              24

(2) INFORMATION FOR SEQ ID NO:38:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:38:

CACTGCGGCC CAGCCTGGTG ATAC                                              24

(2) INFORMATION FOR SEQ ID NO:39:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:39:

CGCTGCTCAT CCTCCAGGTG CGGG                                              24

(2) INFORMATION FOR SEQ ID NO:40:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:40:

```
TCGTCGGAAC TCTTTTGATG AGCA                                              24
```

(2) INFORMATION FOR SEQ ID NO:41:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:41:

```
TTCATCAAAA CCCTTGGGGA CAGC                                              24
```

(2) INFORMATION FOR SEQ ID NO:42:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:42:

```
CCCAGCAGGC AGATGATTCT CGTT                                              24
```

(2) INFORMATION FOR SEQ ID NO:43:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:43:

```
TTGCAGACAC CGAGACTGGG GACT                                              24
```

(2) INFORMATION FOR SEQ ID NO:44:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:44:

```
TCAACGTTGC TGAAGGGAAT CCTC                                              24
```

(2) INFORMATION FOR SEQ ID NO:45:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:45:

```
TGGGAAAGGC CGTGCATTAT TGAT                                              24
```

(2) INFORMATION FOR SEQ ID NO:46:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:46:

CAGCACCAAT TCACCTGCA GCTT                                                24

(2) INFORMATION FOR SEQ ID NO:47:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:47:

ACACTGGCTG CAACAGCATC CAGG                                               24

(2) INFORMATION FOR SEQ ID NO:48:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:48:

TCCCTGTTTA TCCCTGCCGA CAGA                                               24

(2) INFORMATION FOR SEQ ID NO:49:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:49:

AGCAAAATTC ACCATCCCTG AGCG                                               24

(2) INFORMATION FOR SEQ ID NO:50:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:50:

CCTGAAAGCC ACGAAGGCTG ATGA                                               24

(2) INFORMATION FOR SEQ ID NO:51:

(i) SEQUENCE CHARACTERISTICS:
        (A) LENGTH: 24 base pairs
        (B) TYPE: nucleic acid

```
        (C) STRANDEDNESS: single
        (D) TOPOLOGY: linear (ii) MOLECULE TYPE: DNA (xi) SEQUENCE DESCRIPTION: SEQ ID NO:51:

TGCCTCGCTG GATAAATCAT CAGG                                              24

(2) INFORMATION FOR SEQ ID NO:52:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:52:

CTGGATGCAG ACACAAAGCA GAGC                                              24

(2) INFORMATION FOR SEQ ID NO:53:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:53:

TGGCTACGGT ACAAGCCGGA CCCT                                              24

(2) INFORMATION FOR SEQ ID NO:54:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:54:

AGCGCAGCCA TGCAGGCATG TACC                                              24

(2) INFORMATION FOR SEQ ID NO:55:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:55:

AAGCCCGTCT CAGCACCCTC CACA                                              24

(2) INFORMATION FOR SEQ ID NO:56:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA
```

(xi) SEQUENCE DESCRIPTION: SEQ ID NO:56:

TGGTTGTGCA CGAGCGAGAC ACTG                                              24

(2) INFORMATION FOR SEQ ID NO:57:

(i) SEQUENCE CHARACTERISTICS:
              (A) LENGTH: 24 base pairs
              (B) TYPE: nucleic acid
              (C) STRANDEDNESS: single
              (D) TOPOLOGY: linear (ii) MOLECULE TYPE: DNA (xi) SEQUENCE DESCRIPTION: SEQ ID NO:57:

GAAGGGTGGA GAACAGATGC GTCG                                              24

(2) INFORMATION FOR SEQ ID NO:58:

(i) SEQUENCE CHARACTERISTICS:
              (A) LENGTH: 24 base pairs
              (B) TYPE: nucleic acid
              (C) STRANDEDNESS: single
              (D) TOPOLOGY: linear (ii) MOLECULE TYPE: DNA (xi) SEQUENCE DESCRIPTION: SEQ ID NO:58:

ATACACATCA GAATTCTTAC TTTG                                              24

(2) INFORMATION FOR SEQ ID NO:59:

(i) SEQUENCE CHARACTERISTICS:
              (A) LENGTH: 19 base pairs
              (B) TYPE: nucleic acid
              (C) STRANDEDNESS: single
              (D) TOPOLOGY: linear (ii) MOLECULE TYPE: DNA (xi) SEQUENCE DESCRIPTION: SEQ ID NO:59:

GTCACTGGAT TTAGAGTCT                                                    19

(2) INFORMATION FOR SEQ ID NO:60:

(i) SEQUENCE CHARACTERISTICS:
              (A) LENGTH: 24 base pairs
              (B) TYPE: nucleic acid
              (C) STRANDEDNESS: single
              (D) TOPOLOGY: linear (ii) MOLECULE TYPE: DNA (xi) SEQUENCE DESCRIPTION: SEQ ID NO:60:

TCCCACACCC AAAAGGCCAC ACTG                                              24

(2) INFORMATION FOR SEQ ID NO:61:

(i) SEQUENCE CHARACTERISTICS:
              (A) LENGTH: 29 base pairs
              (B) TYPE: nucleic acid
              (C) STRANDEDNESS: single
              (D) TOPOLOGY: linear -continued (ii) MOLECULE TYPE: DNA (xi) SEQUENCE DESCRIPTION: SEQ ID NO:61:

TCGTCGACCC CACTGTGCAC CTCCTTCCC 29